(12) United States Patent
Xiao et al.

(10) Patent No.: US 11,306,296 B2
(45) Date of Patent: Apr. 19, 2022

(54) MG53 MUTANTS, METHODS OF MAKING THE SAME, AND USES THEREOF

(71) Applicant: Hope Medicine (Nanjing) Co., Ltd., Nanjing (CN)

(72) Inventors: Rui-ping Xiao, Beijing (CN); Fengxiang Lu, Beijing (CN); Yan Zhang, Beijing (CN); Sile Guo, Beijing (CN)

(73) Assignee: Hope Medicine (Nanjing) Co., Ltd., Nanjing (CN)

( * ) Notice: Subject to any disclaimer, the term of this patent is extended or adjusted under 35 U.S.C. 154(b) by 110 days.

(21) Appl. No.: 16/262,833

(22) Filed: Jan. 30, 2019

(65) Prior Publication Data

US 2019/0153406 A1 May 23, 2019

Related U.S. Application Data

(63) Continuation-in-part of application No. PCT/CN2017/093640, filed on Jul. 20, 2017.

(30) Foreign Application Priority Data

| Aug. 1, 2016 | (CN) | 201610621989.7 |
| Sep. 23, 2016 | (CN) | 201610847346.4 |
| Jul. 11, 2017 | (CN) | 201710560975.3 |

(51) Int. Cl.
| C12N 9/10 | (2006.01) |
| C07K 14/47 | (2006.01) |
| A61P 13/12 | (2006.01) |
| A61K 38/17 | (2006.01) |
| A61P 9/00 | (2006.01) |
| A61P 9/10 | (2006.01) |
| A61K 38/00 | (2006.01) |

(52) U.S. Cl.
CPC .............. *C12N 9/104* (2013.01); *A61K 38/17* (2013.01); *A61P 9/00* (2018.01); *A61P 9/10* (2018.01); *A61P 13/12* (2018.01); *C07K 14/47* (2013.01); *A61K 38/00* (2013.01); *C12Y 203/02* (2013.01)

(58) Field of Classification Search
None
See application file for complete search history.

(56) References Cited

U.S. PATENT DOCUMENTS

| 6,703,219 B1 | 3/2004 | Potempa et al. |
| 2012/0309051 A1 | 12/2012 | Ma et al. |
| 2015/0361146 A1 | 12/2015 | Xiao et al. |

FOREIGN PATENT DOCUMENTS

| CN | 102143758 A | 8/2011 |
| CN | 1863552 B | 6/2012 |
| CN | 101912617 B | 9/2012 |
| CN | 101797375 B | 1/2013 |
| CN | 103430023 A | 12/2013 |
| CN | 103547281 A | 1/2014 |
| CN | 103966227 B | 5/2015 |
| CN | 103965342 B | 6/2015 |
| CN | 103275980 B | 9/2015 |
| CN | 101932609 B | 3/2016 |
| CN | 107 266 551 A | 10/2017 |
| CN | 107 987 147 A | 5/2018 |
| CN | 108721601 A | 11/2018 |
| CN | 109432404 A | 3/2019 |
| CN | 109528684 A | 3/2019 |
| EP | 3118317 A1 | 1/2017 |
| JP | 2009543551 A | 12/2009 |
| JP | 2016506919 A | 3/2016 |
| JP | 2017508445 A | 3/2017 |
| KR | 10-2010-0099249 A | 9/2010 |
| WO | 2009073808 A2 | 6/2009 |
| WO | 2013036610 A2 | 3/2013 |

(Continued)

OTHER PUBLICATIONS

XP002796574, Database UniProt [Online] Jul. 11, 2012, "SubName: Full=Uncharacterized protein {ECO:0000313I Ensembl:ENSSTOP00000012023};", retrieved from EBI accession No. UNIPROT:I3MKZ0 Database accession No. I3MKZ0, 2 pages https://www.uniprot.org/uniprot/I3MKZO.txt.

(Continued)

*Primary Examiner* — Kagnew H Gebreyesus

(74) *Attorney, Agent, or Firm* — Rimon, P.C.

(57) ABSTRACT

The present invention relates to an MG53 mutant, wherein the MG53 mutant is identical to the amino acid sequence of a wild-type MG53 except for at least one serine in the coiled-coil-SPRY region of the wild-type MG53, which is deleted and/or mutated into any other non-serine or non-threonine amino acid(s). The present invention also relates to a pharmaceutical composition comprising the MG53 mutant, a nucleic acid encoding the MG53 mutant, a method for preparing the MG53 mutant, use of the MG53 mutant in the manufacture of a medicament for treating heart diseases, diabetic cerebrovascular diseases, diabetic ocular complications, diabetic neuropathy, diabetic foot, kidney diseases, and diseases associated with cellular and/or tissue damage. In particular, the MG53 mutant of the present invention may avoid or reduce metabolic side effects, such as, insulin resistance, obesity, diabetes, hypertension, dyslipidemia, etc., brought by the wild-type MG53, while treating heart diseases, diabetic cerebrovascular diseases, diabetic ocular complications, diabetic neuropathy, diabetic foot, kidney diseases, and diseases associated with cellular and/or tissue damage.

20 Claims, 29 Drawing Sheets

Specification includes a Sequence Listing.

(56) References Cited

FOREIGN PATENT DOCUMENTS

WO 2013036610 A3 5/2013

OTHER PUBLICATIONS

XP002796575, Database Uni Prat [Online] Jul. 27, 2011, "SubName: Full= Tripartite motif containing 72 {ECO:0000313I Ensembl :ENSECAP00000006943};", retrieved from EBI accession No. UNIPROT:F6R6S6 Database accession No. F6R6S6, 2 pages https://www.uniprot.org/uniprot/F6R6S6.txt.

Song et al, "Central role of E3 ubiquitin ligase MG53 in insulin resistance and metabolic disorders," Nature, Feb. 1, 2013, vol. 494, No. 7437, p. 375-379 DOI: 10.1038/nature11834.

Zhang et al, "MG53 is a double-edged sword for human diseases," Acta Physiologica Sinica, Aug. 25, 2016, 68(4), p. 505-516.

European Extended Search Report for European patent application EP17836292.7, dated Jan. 23, 2020, 8 pages.

Ma et al., "MG53 Interacts with Cardiolipin to Protect Mitochondria from Ischemia-Reperfusion Induced Oxidative Stress," Biophysical Journal, 112(3): 102a, Feb. 2017.

Nagre et al., "TRIM72 modulates caveolar endocytosis in repair of lung cells," Am J Physiol Lung Cell Mol Physiol 310:L452-L464, 2016 doi:10.1152/ajplung.00089.2015.

Yao et al., "MG53 anchored by dysferlin to cell membrane reduces hepatocyte apoptosis which induced by ischaemia/reperfusion injury in vivo and in vitro," J. Cell. Mol. Med. vol. 21, No. 10, 2017 pp. 2503-2513 doi: 10.1111/jcmm.13171.

Verstraeten et al. "Antioxidant and Membrane Effects of Procyanidin Dimers and Trimers Isolated from Peanut and Cocoa," J. Agric. Food Chem. 2005, 53, 5041-5048 https://doi.org/10.1021/jf058018m.

Cai et al. "MG53 nucleates assembly of cell membrane repair machinery," Nature Cell Biology vol. 11, No. 1, Jan. 2009, pp. 56-64 and additional 9 pages of Supplementary Information published online Nov. 30, 2008, DOI: 10.1038/ncb1812.

Cai et al. "MG53 Regulates Membrane Budding and Exocytosis in Muscle Cells," The Journal of Biological Chemistry vol. 284, No. 5, pp. 3314-3322, Jan. 30, 2009 DOI 10.1074/jbc.M808866200.

Cai et al. "Membrane Repair Defects in Muscular Dystrophy Are Linked to Altered Interaction between MG53, Caveolin-3, and Dysferlin," The Journal of Biological Chemistry vol. 284, No. 23, pp. 15894-15902, Jun. 5, 2009 DOI 10.1074/jbc.M109.009589.

Weisleder et al. "Mitsugumin 53 (MG53) facilitates vesicle trafficking in striated muscle to contribute to cell membrane repair," Communicative & Integrative Biology 2:3, pp. 225-226; May/Jun. 2009 http://dx.doi.org/10.4161/cib.2.3.8077.

Paul McNeil, "Membrane repair redux: redox of MG53," Nature Cell Biology vol. 11, No. 1, Jan. 2009, pp. 7-9.

Jeong et al. "The PRY/SPRY/B30.2 Domain of Butyrophilin 1A1 (BTN1A1) Binds to Xanthine Oxidoreductase," The Journal of Biological Chemistry vol. 284, No. 33, pp. 22444-22456, Aug. 14, 2009 DOI 10.1074/jbc.M109.020446.

Lee et al. "TRIM72 negatively regulates myogenesis via targeting insulin receptor substrate-1," Cell Death and Differentiation (2010) 17, 1254-1265 doi:10.1038/cdd.2010.1.

Jung et al. "TRIM72, a novel negative feedback regulator of myogenesis, is transcriptionally activated by the synergism of MyoD (or myogenin) and MEF2," Biochemical and Biophysical Research Communications 396 (2010) 238-245 doi:10.1016/j.bbrc.2010.04.072.

Wang et al. "Cardioprotection of Ischemia/Reperfusion Injury by Cholesterol-Dependent MG53-Mediated Membrane Repair," Circulation Research, Jul. 9, 2010;107:76-83 DOI: 10.1161/CIRCRESAHA.109.215822.

Cao et al. "MG53 Constitutes a Primary Determinant of Cardiac Ischemic Preconditioning," Circulation. 2010;121:2565-2574 DOI: 10.1161/CIRCULATIONAHA.110.954628.

Park et al. "Crystal structure of PRY-SPRY domain of human TRIM72," Proteins, 2009, structure note, p. 790-795, Published online Oct. 30, 2009 in Wiley InterScience (www.interscience.wiley. com), DOI: 10.1002/prot.22647.

Swamy et al. "Stoichiometry and intracellular fate of TRIM-containing TCR complexes," Cell Communication and Signaling 2010, 8:5 http://www.biosignaling.com/content/8/1/5.

Zhang et al. "MG53 participates in ischaemic postconditioning through the RISK signalling pathway," Cardiovascular Research (2011) 91, 108-115 doi:10.1093/cvr/cvr029.

Zhu et al. "Polymerase Transcriptase Release Factor (PTRF) Anchors MG53 Protein to Cell Injury Site for Initiation of Membrane Repair," The Journal of Biological Chemistry vol. 286, No. 15, pp. 12820-12824, Apr. 15, 2011 DOI 10.1074/jbc.C111.221440.

Weisleder et al. "Visualization of MG53-mediated Cell Membrane Repair Using in vivo and in vitro Systems," J. Vis. Exp. Jun. 2011, (52), e2717 doi:10.3791/2717 (2011).

Li et al. "Determinants of the Higher Order Association of the Restriction Factor TRIM5 and Other Tripartite Motif (TRIM) Proteins," The Journal of Biological Chemistry vol. 286, No. 32, pp. 27959-27970, Aug. 12, 2011 DOI 10.1074/jbc.M111.260406.

Birtley et al. "The Crystal Structure of Human Endoplasmic Reticulum Aminopeptidase 2 Reveals the Atomic Basis for Distinct Roles in Antigen Processing," Biochemistry 2012, 51, 286-295 dx.doi.org/10.1021/bi201230p.

He et al. "Enhancing Muscle Membrane Repair by Gene Delivery of MG53 Ameliorates Muscular Dystrophy and Heart Failure in δ-Sarcoglycan-deficient Hamsters," Molecular Therapy vol. 20 No. 4, 727-735 Apr. 2012 doi:10.1038/mt.2012.5.

Hu et al. "A MID1 Gene Mutation in a Patient With Opitz G/BBB Syndrome That Altered the 3D Structure of SPRY Domain," Am J Med Genet Part A 158A:726-731 (Received Aug. 11, 2011; Accepted Dec. 5, 2011) Published online Mar. 9, 2012 in Wiley Online Library DOI 10.1002/ajmg.a.35216.

Lin et al. "Nonmuscle myosin IIA facilitates vesicle trafficking for MG53-mediated cell membrane repair," The FASEB Journal, vol. 26, 1875-1883 (2012) doi: 10.1096/fj.11-188599.

Weisleder et al. "Recombinant MG53 Protein Modulates Therapeutic Cell Membrane Repair in Treatment of Muscular Dystrophy," Science Translational Medicine Jun. 20, 2012: vol. 4, Issue 139, pp. 139ra85 DOI: 10.1126/scitranslmed.3003921.

Flix et al. "Dysferlin interacts with calsequestrin-1, myomesin-2 and dynein in human skeletal muscle," The International Journal of Biochemistry & Cell Biology 45 (2013) 1927-1938 http://dx.doi.org/10.1016/j.biocel.2013.06.007.

Ham et al. "Compensation of the AKT signaling by ERK signaling in transgenic mice hearts overexpressing TRIM72," Experimental Cell Search 319 (2013) 1451-1462 http://dx.doi.org/10.1016/j.yexcr.2013.02.016.

Ma et al. "Hypercholesterolemia blocked sevoflurane-induced cardioprotection against ischemia-reperfusion injury by alteration of the MG53/RISK/GSK3β signaling," International Journal of Cardiology 168 (2013) 3671-3678 http://dx.doi.org/10.1016/j.ijcard.2013.06.037.

Song et al. "Central role of E3 ubiquitin ligase MG53 in insulin resistance and metabolic disorders," Nature, Feb. 21, 2013, vol. 494, 375-381 doi:10.1038/nature11834.

Corona et al. "Effect of Recombinant Human MG53 Protein On Tourniquet-Induced Ischemia-Reperfusion Injury in Rat Muscle," Muscle & Nerve Jun. 2014, 919-921 DOI 10.1002/mus.24160.

Kim et al. "TRIM72 is required for effective repair of alveolar epithelial cell wounding," Am J Physiol Lung Cell Mol Physiol 307: L449-L459, 2014 doi:10.1152/ajplung.00172.2014.

Kohr et al. "S-nitrosylation of TRIM72 at cysteine 144 is critical for protection against oxidation-induced protein degradation and cell death," Journal of Molecular and Cellular Cardiology 69 (2014) 67-74 http://dx.doi.org/10.1016/j.yjmcc.2014.01.010.

Marshall et al. "Proteomic mapping of proteins released during necrosis and apoptosis from cultured neonatal cardiac myocytes," Am J Physiol Cell Physiol 306: C639-C647, 2014 doi:10.1152/ajpcell.00167.2013.

(56) References Cited

OTHER PUBLICATIONS

Nguyen et al. "Mitsugumin 53 (MG53) Ligase Ubiquitinates Focal Adhesion Kinase during Skeletal Myogenesis," The Journal of Biological Chemistry vol. 289, No. 6, pp. 3209-3216, Jan. 7, 2014 DOI 10.1074/jbc.M113.525154.

Ohno et al. "Loading-associated expression of TRIM72 and caveolin-3 in antigravitational soleus muscle in mice," Physiol Rep, 2 (12), 2014, e12259 doi: 10.14814/phy2.12259.

Palus et al. "Muscle wasting: an overview of recent developments in basic research," J Cachexia Sarcopenia Muscle (2014) 5:193-198 DOI 10.1007/s13539-014-0157-7.

Sanchez et al. "The tripartite motif coiled-coil is an elongated antiparallel hairpin dimer," PNAS, Feb. 18, 2014, vol. 111, No. 7, 2494-2499 www.pnas.org/lookup/suppl/doi:10.1073/pnas.1318962111/-/DCSupplemental.

Chan et al. "S-nitrosylation of TRIM72 mends the broken heart: A molecular modifier-mediated cardioprotection," Journal of Molecular and Cellular Cardiology 72 (2014) 292-295 http://dx.doi.org/10.1016/j.yjmcc.2014.04.004.

Duann et al. "MG53-mediated cell membrane repair protects against acute kidney injury," Sci Transl Med, Mar. 18, 2015 vol. 7 Issue 279 279ra36 DOI: 10.1126/scitranslmed.3010755.

Liu et al. "Cardioprotection of recombinant human MG53 protein in a porcine model of ischemia and reperfusion injury," Journal of Molecular and Cellular Cardiology 80 (2015) 10-19 http://dx.doi.org/10.1016/j.yjmcc.2014.12.010.

Liu et al. "Upregulation of MG53 Induces Diabetic Cardiomyopathy Through Transcriptional Activation of Peroxisome Proliferation-Activated Receptor α," Circulation. Mar. 3, 2015;131:795-804. DOI: 10.1161/CIRCULATIONAHA.114.012285.

Mokhonova et al. "The E3 ubiquitin ligase TRIM32 regulates myoblast proliferation by controlling turnover of NDRG2," Human Molecular Genetics, 2015, vol. 24, No. 10, 2873-2883 doi: 10.1093/hmg/ddv049.

Zhou et al. "MG53 protein: A promising novel therapeutic target for myocardial ischemia reperfusion injury," International Journal of Cardiology 199 (2015) 424-425 http://dx.doi.org/10.1016/j.ijcard.2015.07.084.

Zhu et al. "Amelioration of Ischemia-Reperfusion-Induced Muscle Injury by the Recombinant Human MG53 Protein," Muscle & Nerve Month 2015, 7 pages DOI 10.1002/mus.24619.

Lemckert et al. "Lack of MG53 in human heart precludes utility as a biomarker of myocardial injury or endogenous cardioprotective factor," Cardiovascular Research Advance Access published Feb. 7, 2016 doi:10.1093/cvr/cvw017.

Ozato et al. "TRIM family proteins and their emerging roles in innate immunity," Nature Reviews, Immunology, vol. 8, Nov. 2008, 849-860 doi:10.1038/nri2413.

International Search Report for PCT/CN2017093640, dated Sep. 13, 2017, 3 pages.

1st Office Action for Chiness patent applcation CN201780003946.5, dated Jul. 28, 2021, 8 pages.

Genbank: XP_004439526.1, Predicted: tripartite motif-containing protein 72 [Ceratotherium simum simum], Nov. 27, 2015, 2 pages.

Genbank: XP_004671095.1, tripartite motif-containing protein 72 [ J aculus jaculus], dated Jun. 23, 2015, 2 pages.

Nguyen et al., "Mitsugumin 53 (MG53) Ligase Ubiquitinates Focal Adhesion Kinase during Skeletal Myogenesis," Journal of Biological Chemistry, Jan. 7, 2014, vol. 289, No. 6, P3209-3216.

MSAAPGLLHQELSCPLCLQLFDAPVTAECGHSFCRACLGRVAGE
PAADGTVLCPCCQAPTRPQALSTNLQLARLVEGLAQVPQGHCEEHLDPLSIYCEQDRA
LVCGVCASLGSHRGHRLLPAAEAHARLKTQLPQQKLQLQEACMRKEKSVAVLEHQLVE
VEETVRQFRGAVGEQLGKMRVFLAALEGSLDREAERVRGEAGVALRRELGSLNSYLEQ
LRQMEKVLEEVADKPQTEFLMKYCLVTSRLQKILAESPPPARLDIQLPIISDDFKFQV
WRKMFRALMPALEELTFDPSSAHPSLVVSSSGRRVECSEQKAPPAGEDPRQFDKAVAV
VAHQQLSEGEHYWEVDVGDKPRWALGVIAAEAPRRGRLHAVPSQGLWLLGLREGKILE
AHVEAKEPRALRSPERRPTRIGLYLSFGDGVLSFYDASDADALVPLFAFHERLPRPVY
PFFDVCWHDKGKNAQPLLLVGPEGAEA  (SEQ ID NO: 1)

ATGTCGGCTGCGCCCGGCCTCCTGCACCAGGAGCTGTCCTGCCCGCTGTGCCTGCAGCTGTTCGACGCGC
CCGTGACAGCCGAGTGCGGCCACAGTTTCTGCCGCGCCTGCCTAGGCCGCGTGGCCGGGGAGCCGGCGGC
GGATGGCACCGTTCTCTGCCCCTGCTGCCAGGCCCCCACGCGGCCGCAGGCACTCAGCACCAACCTGCAG
CTGGCGCGCCTGGTGGAGGGGCTGGCCCAGGTGCCGCAGGGCCACTGCGAGGAGCACCTGGACCCGCTGA
GCATCTACTGCGAGCAGGACCGCGCGCTGGTGTGCGGAGTGTGCGCCTCACTCGGCTCGCACCGCGGTCA
TCGCCTCCTGCCTGCCGCCGAGGCCCACGCACGCCTCAAGACACAGCTGCCACAGCAGAAACTGCAGCTG
CAGGAGGCATGCATGCGCAAGGAGAAGAGTGTGGCTGTGCTGGAGCATCAGCTGGTGGAGGTGGAGGAGA
CAGTGCGTCAGTTCCGGGGGGCCGTGGGGGAGCAGCTGGGCAAGATGCGGGTGTTCCTGGCTGCACTGGA
GGGCTCCTTGGACCGCGAGGCAGAGCGTGTACGGGGTGAGGCAGGGGTCGCCTTGCGCCGGGAGCTGGGG
AGCCTGAACTCTTACCTGGAGCAGCTGCGGCAGATGGAGAAGGTCCTGGAGGAGGTGGCGGACAAGCCGC
AGACTGAGTTCCTCATGAAATACTGCCTGGTGACCAGCAGGCTGCAGAAGATCCTGGCAGAGTCTCCCCC
ACCCGCCCGTCTGGACATCCAGCTGCCAATTATCTCAGATGACTTCAAATTCCAGGTGTGGAGGAAGATG
TTCCGGGCTCTGATGCCAGCGCTGGAGGAGCTGACCTTTGACCCGAGCTCTGCGCACCCGAGCCTGGTGG
TGTCTTCCTCTGGCCGCCGCGTGGAGTGCTCGGAGCAGAAGGCGCCGCCGGCCGGGGAGGACCCGCGCCA
GTTCGACAAGGCGGTGGCGGTGGTGGCGCACCAGCAGCTCTCCGAGGGCGAGCACTACTGGGAGGTGGAT
GTTGGCGACAAGCCGCGCTGGGCGCTGGGCGTGATCGCGGCCGAGGCCCCCCGCCGCGGGCGCCTGCACG
CGGTGCCCTCGCAGGGCCTGTGGCTGCTGGGGCTGCGCGAGGGCAAGATCCTGGAGGCACACGTGGAGGC
CAAGGAGCCGCGCGCTCTGCGCAGCCCCGAGAGGCGGCCCACGCGCATTGGCCTTTACCTGAGCTTCGGC
GACGGCGTCCTCTCCTTCTACGATGCCAGCGACGCCGACGCGCTCGTGCCGCTTTTTGCCTTCCACGAGC
GCCTGCCCAGGCCCGTGTACCCCTTCTTCGACGTGTGCTGGCACGACAAGGGCAAGAATGCCCAGCCGCT
GCTGCTCGTGGGTCCCGAAGGCGCCGAGGCCTGA  (SEQ ID No: 19)

Fig. 2

MSAAPGLLRQELSCPLCLQLFDAPVTAECGHSFCRACLIRVAGE
PAADGTVACPCCQAPTRPQALSTNLQLSRLVEGLAQVPQGHCEEHLDPLSIYCEQDRT
LVCGVCASLGSHRGHRLLPAAEAQARLKTQLPQQKMQLQEACMRKEKTVAVLEHQLVE
VEETVRQFRGAVGEQLGKMRMFLAALESSLDREAERVRGDAGVALRRELSSLNSYLEQ
LRQMEKVLEEVADKPQTEFLMKFCLVTSRLQKILSESPPPARLDIQLPVISDDFKFQV
WKKMFRALMPALEELTFDPSSAHPSLVVSSSGRRVECSDQKAPPAGEDTRQFDKAVAV
VAQQLLSQGEHYWEVEVGDKPRWALGVMAADASRRGRLHAVPSQGLWLLGLRDGKILE
AHVEAKEPRALRTPERPPARIGLYLSFADGVLAFYDASNPDVLTPIFSFHERLPGPVY
PIFDVCWHDKGKNAQPLLLVGPEQEQA (SEQ ID NO: 2)

ATGTCGGCTGCACCCGGCCTTCTGCGTCAGGAACTGTCCTGCCCACTGTGCTTGCAGCTGTTCGATGCGC
CAGTGACGGCTGAGTGTGGCCACAGTTTCTGCCGTGCCTGCCTGATCCGGGTGGCAGGGGAGCCTGCTGC
GGACGGCACAGTTGCCTGTCCCTGTTGTCAGGCACCTACACGGCCGCAGGCTCTAAGCACTAACCTCCAG
TTGTCACGCCTTGTGGAGGGTTTGGCGCAAGTGCCCCAAGGCCACTGCGAGGAACACCTGGATCCACTGA
GCATCTACTGCGAGCAGGACCGCACACTTGTGTGTGGTGTGTGTGCCTCGCTCGGTTCTCACCGTGGTCA
TCGTCTCCTGCCTGCCGCTGAAGCCCAAGCACGCCTCAAGACACAGCTTCCACAGCAGAAGATGCAGCTG
CAGGAGGCATGCATGCGCAAGGAGAAGACTGTAGCGGTGCTGGAGCATCAGCTGGTGGAGGTGGAGGAGA
CAGTGCGCCAGTTCCGGGGAGCTGTCGGGGAGCAGCTGGGGAAGATGCGGATGTTCCTGGCTGCCCTAGA
AAGTTCTCTGGACCGTGAAGCAGAAAGGGTTCGGGGTGATGCTGGGGTTGCCTTGCGTCGGGAGCTGTCA
AGCCTGAACTCTTACCTAGAGCAACTGAGGCAGATGGAGAAGGTGCTGGAGGAGGTGGCTGACAAGCCAC
AGACAGAATTCCTCATGAAATTCTGCCTGGTAACCAGCAGGCTGCAGAAGATCCTGTCAGAGTCACCACC
ACCGGCAAGGCTAGATATCCAGCTGCCTGTCATCTCAGATGACTTCAAATTCCAGGTGTGGAAGAAGATG
TTCCGGGCTCTGATGCCAGCGCTGGAGGAACTGACTTTTGACCCCAGCTCTGCGCACCCGAGCCTGGTGG
TGTCCTCCTCTGGTCGCCGAGTGGAGTGCTCAGACCAGAAGGCGCCGCCAGCGGGAGAAGACACGCGTCA
GTTCGACAAGGCAGTAGCGGTGGTGGCGCAGCAGCTGCTGTCACAGGGCGAGCACTATTGGGAGGTGGAG
GTGGGCGACAAACCACGCTGGGCCCTGGGAGTGATGGCGGCTGACGCTTCCGCCGTGGCCGGCTGCACG
CGGTGCCCTCACAGGGGCTGTGGCTGCTGGGTCTGCGCGATGGCAAGATCCTGGAGGCGCACGTGGAGGC
CAAGGAGCCGCGGGCACTGCGCACCCCAGAGAGGCCTCCGGCGCGCATTGGCCTCTACCTAAGCTTCGCA
GATGGCGTCCTGGCTTTCTATGATGCGAGCAACCCCGACGTACTTACGCCAATCTTTTCTTTCCACGAGC
GTCTGCCCGGGCCGGTGTACCCCATCTTTGACGTGTGCTGGCACGACAAGGGCAAGAATGCCCAGCCCCT
GCTGCTTGTGGGGCCGGAGCAGGAACAGGCCTGA (SEQ ID NO: 20)

Fig. 3

```
MSTAPGLLRQELSCPLCLQLFDAPVTAECGHSFCRACLIRVAGE
PADDGTVACPCCQASTRPQALSTNLQLARLVEGLAQVPQGHCEEHLDPLSIYCEQDRT
LVCGVCASLGSHRGHRLLPAAEAHARLKTQLPQQKAQLQEACMRKEKSVAVLEHQLVE
VEETVRQFRGAVGEQLGKMRMFLAALESSLDREAERVRGEAGVALRRELSSLNSYLEQ
LRQMEKVLEEVADKPQTEFLMKFCLVTSRLQKILSESPPPARLDIQLPVISDDFKFQV
WKKMFRALMPELEELTFDPSSAHPSLVVSASGRRVECSEQKAPPAGEDTCQFDKTVAV
VAKQLLSQGEHYWEVEVGDKPRWALGVMAADASRRGRLHAVPSQGLWLLGLRDGKILE
AHVEAKEPRALRTPERPPARIGLYLSFADGVLTFYDASNTDALTPLFSFHERLPGPVY
PMFDVCWHDKGKNSQPLLLVGPDSEQA (SEQ ID NO: 3)
```

```
ATGTCGACTGCACCAGGCCTTTTGCGCCAGGAACTGTCTTGCCCGCTGTGCTTGCAGCTGTTCGATGCAC
CAGTGACCGCTGAGTGTGGCCACAGTTTCTGCCGTGCCTGCCTGATCCGTGTGGCAGGGGAGCCTGCCGA
CGATGGCACGGTTGCCTGTCCCTGTTGTCAGGCATCTACTCGGCCACAGGCGCTAAGCACTAACCTCCAG
TTGGCACGCCTTGTGGAGGGTTTGGCACAAGTGCCCCAAGGCCACTGCGAGGAACACCTGGATCCACTGA
GCATCTACTGCGAGCAGGACCGCACACTTGTGTGTGGTGTGTGTGCCTCTCTCGGTTCACACCGTGGTCA
CCGTCTTCTGCCTGCCGCAGAAGCCCATGCACGTCTCAAGACACAGCTTCCACAACAGAAGGCCCAGCTG
CAGGAGGCATGCATGCGCAAGGAGAAGAGTGTAGCAGTCCTGGAGCATCAGCTGGTGGAGGTGGAGGAGA
CCGTGCGTCAGTTCCGGGGAGCTGTTGGGGAGCAGCTGGGGAAGATGCGGATGTTCCTGGCTGCCCTAGA
AAGTTCTTTGGACCGTGAAGCAGAAAGGGTTCGAGGTGAGGCAGGGGTTGCCTTGCGGCGGGAGCTGTCA
AGCCTGAACTCTTACCTGGAGCAACTGAGGCAGATGGAGAAGGTGCTGGAGGAGGTGGCTGACAAGCCAC
AGACAGAATTCCTCATGAAATTCTGCCTGGTGACCAGCAGGCTGCAGAAGATTCTGTCAGAGTCACCACC
CCCAGCAAGGCTAGATATCCAGCTGCCTGTCATCTCAGATGACTTCAAATTCCAGGTGTGGAAGAAGATG
TTCCGGGCTCTGATGCCAGAGTTGGAGGAACTGACTTTTGACCCCAGCTCTGCGCACCCGAGCCTGGTGG
TGTCCGCCTCTGGTCGCCGAGTGGAGTGCTCGGAGCAGAAGGCGCCGCCAGCAGGAGAAGACACGTGCCA
GTTCGACAAGACGGTAGCGGTAGTGGCGAAGCAGCTGCTGTCACAGGGGGAGCACTACTGGGAGGTGGAG
GTGGGCGACAAGCCACGCTGGGCCCTGGGTGTGATGGCGGCTGACGCTTCCCGTCGTGGCCGCCTGCACG
CGGTGCCCTCACAGGGGCTGTGGTTGCTCGGCCTGCGCGATGGCAAGATCCTGGAGGCACACGTGGAGGC
CAAGGAGCCACGGGCACTGCGCACCCCAGAGAGGCCACCAGCGCGCATTGGCCTCTACCTAAGCTTTGCA
GATGGCGTCCTGACTTTCTATGATGCAAGCAACACCGACGCGCTTACACCGCTCTTTTCTTTTCATGAGC
GTCTGCCTGGGCCGGTGTACCCCATGTTTGACGTGTGCTGGCACGACAAGGGCAAGAATTCTCAGCCGCT
GTTGCTCGTGGGGCCAGACAGTGAGCAGGCCTGA (SEQ ID NO: 21)
```

Fig. 4

```
MSAAPGLLHQELSCPLCLQLFDAPVTAECGHSFCRACLGRVAGE
PAADGTVLCPCCQAPTRPQALSTNLQLARLVEGLAQVPQGHCEEHLDPLSIYCEQDRA
LVCGVCASLGSHRGHRLLPAAEAHARLKTQLPQQKLQLQEACMRKEKSVAVLEHQLVE
VEETVRQFRGAVGEQLGKMRVFLAALEGSLDREAERVRGEAGVALRRELGSLNSYLEQ
LRQMEKVLEEVADKPQTEFLMKYCLVTSRLQKILAESPPPARLDIQLPIISDDFKFQV
WRKMFRALMPALEELTFDPSSAHPSLVVSSSGRRVECSEQKAPPAGEDPRQFDKAVAV
VAHQQLSEGEHYWEVEVGDKPRWALGVIAAEGPRRGRLHAVPSQGLWLLGLREGKILE
AHVEAKEPRALRSPERRPTRIGLYLSFGDGVLSFYDASDADALVPLFAFHERLPGPVY
PFFDVCWHDKGKNSQPLLLVGSEGAEA(SEQ ID NO: 4)
```

```
ATGTCGGCTGCGCCGGGCCTCCTGCACCAGGAGCTGTCCTGCCCGCTGTGCCTGCAGCTGTTCGACGCGC
CCGTGACAGCCGAGTGCGGCCACAGTTTCTGTCGCGCCTGCCTGGGCCGCGTGGCCGGGGAACCGGCGGC
GGATGGCACCGTTCTCTGCCCCTGCTGTCAGGCCCCCACGCGGCCGCAGGCACTCAGCACCAACCTGCAG
CTGGCGCGCCTGGTGGAGGGGCTGGCCCAGGTGCCGCAGGGCCACTGCGAGGAGCACCTGGACCCGCTGA
GCATCTACTGTGAGCAGGACCGCGCGCTGGTGTGCGGAGTGTGCGCCTCACTCGGCTCGCACCGCGGTCA
TCGCCTGCTGCCCGCCGCCGAGGCCCACGCACGCCTCAAGACGCAGCTGCCACAGCAGAAACTGCAGCTG
CAGGAGGCATGCATGCGCAAGGAGAAGAGTGTAGCTGTGCTGGAGCATCAGTTGGTGGAAGTGGAGGAGA
CAGTGCGTCAGTTCCGGGGGGCCGTGGGGGAGCAGCTGGGCAAGATGCGGGTGTTCCTGGCTGCACTGGA
GGGCTCCTTGGACCGTGAGGCAGAGCGTGTGCGGGGTGAGGCAGGGGTCGCCTTGCGCCGGGAGCTGGGG
AGCCTGAACTCTTACCTGGAGCAGCTGCGGCAGATGGAGAAGGTGCTGGAGGAGGTGGCCGACAAGCCGC
AGACTGAGTTCCTAATGAAATACTGCCTGGTGACCAGCAGGCTGCAGAAGATCCTGGCAGAGTCTCCCCC
ACCCGCCCGTCTGGACATCCAGCTGCCAATCATCTCAGATGACTTCAAATTCCAGGTGTGGAGGAAGATG
TTCCGGGCTCTGATGCCAGCGCTGGAGGAGCTGACCTTTGACCCGAGCTCTGCGCACCCCAGCCTGGTGG
TGTCTTCCTCCGGCCGCCGCGTGGAGTGCTCGGAGCAGAAGGCGCCGCCGGCGGGGGAGGACCCGCGCCA
GTTCGACAAGGCGGTAGCGGTGGTGGCGCACCAGCAGCTCTCCGAGGGCGAACACTACTGGGAGGTGGAG
GTGGGCGACAAGCCGCGCTGGGCGCTGGGTGTGATCGCGGCCGAGGGGCCCCGTCGCGGGCGCCTGCACG
CGGTGCCCTCGCAGGGCCTGTGGCTGCTGGGGCTGCGTGAGGGCAAGATCCTGGAGGCTCACGTGGAGGC
CAAGGAGCCGCGCGCTCTGCGCAGCCCCGAGCGGCGGCCCACGCGCATCGGCCTCTACCTGAGCTTCGGC
GACGGCGTCCTCTCCTTCTACGATGCCAGCGACGCCGACGCGCTCGTGCCGCTTTTTGCCTTCCACGAGC
GCCTGCCTGGGCCCGTGTACCCCTTCTTCGACGTGTGCTGGCACGACAAGGGCAAGAACTCCCAGCCGCT
GCTGCTCGTGGGGTCCGAAGGCGCCGAAGCCTGA (SEQ ID NO: 22)
```

Fig. 5

MSAAPGLLHQELSCPLCLQLFDAPVTAECGHSFCRACLGRVAGE
PAADGTVLCPSCQAPTRPQALSTNQQLARLVEGLAQVPQGHCEEHLDPLSIYCEQDRV
LVCGVCASLGSHRGHRLLPAAEAHARLKTQLPQQKLQLQEACMRKEKSVGVLEQQLVE
VEETVRQFRGAVGEQLGKMRLFLAALEGSLDREAERVRGEAGVALRRELGSLKSYLEQ
LRQMEKVLEEVADKPQTEFLMKYCLVTSRLQKILAESPPPARLDIQLPVISDDFKFQV
WRKMFRALMPAMQELTFDPSTAHPSLVLSASGRRVECSEQKAPPAGEDPRQFDKAVAV
VTHQLLSEGEHYWEVEVGDKPRWALGVIGAQAGRRGRLHAVPSQGLWLLGLREGKILE
AHVEAKEPRALRTPERRPSRIGIYLSFADGVLSFYDASDADALELLFAFHERLPGPVY
PFFDVCWHDKGKNAQPLLLVGPDSGGEA (SEQ ID NO: 5)

ATGTCAGCTGCGCCCGGCCTCCTGCACCAGGAGCTGTCCTGTCCGCTGTGCCTGCAGCTGTTCGATGCGC
CGGTGACGGCTGAGTGCGGCCACAGCTTCTGCCGCGCCTGCCTGGGCCGCGTGGCAGGGGAGCCAGCCGC
GGATGGCACGGTGCTCTGCCCCAGCTGCCAGGCACCCACGCGGCCGCAGGCGCTCAGCACCAACCAGCAG
CTGGCGCGCCTGGTGGAGGGGCTGGCGCAGGTGCCGCAGGGCCACTGCGAGGAGCACCTAGACCCGCTCA
GCATCTACTGCGAGCAGGACCGCGTGCTCGTGTGCGGCGTCTGCGCCTCGCTGGGTTCGCACCGCGGCCA
CCGCCTGCTGCCCGCCGCCGAAGCCCATGCGCGCCTTAAGACGCAGCTCCCGCAGCAGAAGCTGCAGCTG
CAGGAGGCGTGTATGCGGAAGGAGAAGAGCGTGGGTGTGCTGGAGCAACAACTGGTGGAAGTGGAGGAGA
CGGTGCGTCAGTTCCGGGGGCAGTGGGGGAGCAGCTGGGCAAGATGCGGTTGTTCCTGGCTGCACTGGA
GGGCTCCTTGGACCGAGAAGCAGAGCGTGTGCGGGGTGAGGCGGGGGTCGCCTTGCGGAGGGAGCTGGGG
AGCCTGAAGTCTTACTTGGAGCAGCTGCGGCAGATGGAGAAGGTGCTGGAGGAGGTGGCAGACAAGCCCC
AGACCGAGTTCCTCATGAAATACTGCCTGGTGACCAGCAGGCTGCAGAAGATCCTGGCAGAGTCGCCCCC
ACCTGCCCGCCTGGACATTCAGCTGCCTGTCATCTCAGACGACTTCAAATTCCAGGTGTGGAGAAAGATG
TTCCGGGCCCTGATGCCAGCGATGCAGGAGCTGACCTTTGACCCCAGCACGGCCCACCCGAGCCTGGTGC
TGTCGGCCTCGGGCCGCCGCGTGGAGTGCTCGGAGCAGAAGGCGCCGCCGGCCGGAGAGGACCCGCGCCA
GTTCGACAAGGCGGTGGCGGTGGTGACGCACCAGCTGCTGTCGGAAGGCGAGCACTACTGGGAGGTGGAG
GTGGGCGACAAGCCACGCTGGGCGCTGGGCGTGATCGGGGCCCAGGCCGGTCGCCGCGGCCGGCTGCACG
CCGTGCCCTCGCAGGGCCTCTGGCTGCTCGGGCTGCGCGAGGGCAAGATCCTGGAGGCTCACGTCGAGGC
CAAGGAGCCGCGCGCCCTGCGCACCCCGGAGAGGCGGCCGTCGCGCATCGGGATCTACCTGAGCTTCGCG
GATGGCGTCCTCTCGTTCTACGACGCCAGCGACGCCGACGCGCTGGAGCTGCTCTTCGCCTTCCACGAAC
GCCTGCCGGGCCCCGTGTACCCCTTCTTCGACGTGTGCTGGCACGACAAGGGCAAGAACGCTCAGCCGCT
CCTGCTGGTGGGGCCCGACAGCGGCGGGGAGGCCTGA (SEQ ID NO: 23)

Fig. 6

```
MSAAPGLLHQELSCPLCLQLFDAPVTAECGHSFCRACLSRVAGE
PAADGTVPCPCCQALTRPQALSTNQQLARLVEGLAQVPQGHCEEHLDPLSIYCEQDRA
LVCGVCASLGSHRGHRLLPAAEAHARLKTQLPQQKLQLQEACMRKEKSVALLEHQLME
VEEMVRQFRGAVGEQLGKMRVFLAALEGSLDREAERVRGEAGVALRRELGSLNSYLEQ
LRQMEKVLEEVADKPQTEFLMKYCLVTSRLQKILAESPPPARLDIQLPVISDDFKFQV
WRKMFRALMPVTKELTFDPSSAHPSLVLSPSGRRVECSDQKAPPAGEDPCQFDKAVAV
VAQQVLSDGEHYWEVQVGEKPRWALGVIAAQASRRGRLHAVPSQGLWLLGLRDGKILE
AHVEAKEPRALRTPERRPTRIGIYLSFGDGVLSFYDASDPDALELLFAFHERLPGPVY
PFFDVCWHDKGKNAQPLLLVGPDGEEA (SEQ ID NO: 6)
```

```
ATGTCGGCCGCGCCGGGCCTCCTGCACCAGGAGCTGTCCTGCCCGCTCTGCCTGCAGCTGTTTGACGCGC
CGGTGACCGCCGAGTGCGGCCACAGTTTCTGCCGCGCCTGCCTGAGCCGCGTGGCTGGGGAGCCGGCGGC
GGACGGCACCGTGCCCTGCCCGTGCTGCCAGGCACTCACGCGGCCACAGGCGCTCAGCACCAACCAGCAG
CTGGCGCGCCTGGTGGAGGGGCTGGCGCAGGTGCCGCAGGGCCACTGCGAGGAGCACCTAGACCCGCTCA
GCATCTACTGCGAGCAGGATCGAGCGCTCGTGTGCGGCGTGTGCGCCTCGCTCGGCTCGCACCGCGGCCA
CCGCCTGCTGCCCGCCGCCGAAGCCCACGCGCGCCTCAAGACACAGCTGCCACAGCAGAAACTGCAGCTG
CAGGAGGCATGTATGCGCAAGGAGAAGAGTGTGGCTCTGCTGGAGCATCAGCTCATGGAAGTGGAGGAGA
TGGTGCGTCAGTTCCGGGGGCTGTAGGGGAGCAGCTGGGCAAGATGCGGGTGTTCCTGGCTGCACTGGA
GGGCTCCTTGGACCGTGAGGCAGAGCGCGTGCGGGGAGAGGCAGGGGTTGCCCTGCGGCGGGAGCTGGGG
AGCCTGAACTCTTACCTGGAGCAGTTGCGTCAGATGGAGAAGGTGCTGGAGGAGGTGGCCGACAAGCCAC
AGACTGAGTTCCTCATGAAATACTGCCTGGTGACCAGCAGGCTACAGAAGATCCTGGCAGAATCACCACC
GCCTGCCCGTTTGGACATCCAGCTGCCTGTCATCTCAGATGACTTCAAATTCCAGGTGTGGAGGAAGATG
TTCCGGGCTCTGATGCCAGTTACAAAGGAGCTGACCTTTGACCCGAGCTCTGCGCACCCGAGCCTGGTGC
TGTCTCCCTCCGGTCGCCGCGTGGAGTGCTCGGACCAGAAGGCGCCGCCGGCCGGGGAGGATCCGTGCCA
GTTCGACAAGGCCGTGGCGGTGGTGGCGCAGCAGGTGCTGTCCGACGGCGAGCACTACTGGGAGGTGCAG
GTGGGCGAGAAGCCGCGCTGGGCCCTCGGCGTGATCGCGGCCCAGGCCAGCCGCCGCGGCCGGCTGCACG
CCGTCCCCTCGCAGGGCCTCTGGCTGCTCGGGCTGCGGGACGGCAAGATCCTGGAGGCGCACGTCGAAGC
CAAGGAGCCGCGCGCGCTGCGCACCCCGGAGAGGCGGCCCACGCGCATCGGGATCTACCTAAGCTTCGGC
GACGGAGTCCTCTCCTTTTATGATGCCAGTGACCCCGACGCCCTCGAGCTGCTCTTTGCCTTCCACGAGC
GCCTGCCCGGCCCGTGTACCCCTTCTTCGACGTATGCTGGCACGACAAGGGCAAAAATGCTCAGCCGCT
GCTGCTGGTGGGGCCTGATGGCGAGGAGGCCTGA(SEQ ID NO: 24)
```

Fig. 7

MSAAPGLLHQELSCPLCLQLFDAPVTAECGHSFCRACLGRVAGE
PAADGTVLCPCCQAPTRPQALSTNLQLARLVEGLAQVPQGHCEEHLDPLSIYCEQDRA
LVCGVCASLGSHRGHRLLPAAEAHARLKTQLPQQKLQLQEACMRKEKSVAVLEHQLVE
VEETVRQFRGAVGEQLGKMRVFLAALEGSLDREAERVRGEAGVALRRELGSLNSYLEQ
LRQMEKVLEEVADKPQTEFLMKYCLVTSRLQKILAEAPPPARLDIQLPIISDDFKFQV
WRKMFRALMPALEELTFDPSSAHPSLVVSSSGRRVECSEQKAPPAGEDPRQFDKAVAV
VAHQQLSEGEHYWEVDVGDKPRWALGVIAAEAPRRGRLHAVPSQGLWLLGLREGKILE
AHVEAKEPRALRSPERRPTRIGLYLSFGDGVLSFYDASDADALVPLFAFHERLPRPVY
PFFDVCWHDKGKNAQPLLLVGPEGAEA(SEQ ID NO: 7)

ATGTCGGCTGCGCCCGGCCTCCTGCACCAGGAGCTGTCCTGCCCGCTGTGCCTGCAGCTGTTCGACGCGC
CCGTGACAGCCGAGTGCGGCCACAGTTTCTGCCGCGCCTGCCTAGGCCGCGTGGCCGGGGAGCCGGCGGC
GGATGGCACCGTTCTCTGCCCCTGCTGCCAGGCCCCCACGCGGCCGCAGGCACTCAGCACCAACCTGCAG
CTGGCGCGCCTGGTGGAGGGGCTGGCCCAGGTGCCGCAGGGCCACTGCGAGGAGCACCTGGACCCGCTGA
GCATCTACTGCGAGCAGGACCGCGCGCTGGTGTGCGGAGTGTGCGCCTCACTCGGCTCGCACCGCGGTCA
TCGCCTCCTGCCTGCCGCCGAGGCCCACGCACGCCTCAAGACACAGCTGCCACAGCAGAAACTGCAGCTG
CAGGAGGCATGCATGCGCAAGGAGAAGAGTGTGGCTGTGCTGGAGCATCAGCTGGTGGAGGTGGAGGAGA
CAGTGCGTCAGTTCCGGGGGGCCGTGGGGGAGCAGCTGGGCAAGATGCGGGTGTTCCTGGCTGCACTGGA
GGGCTCCTTGGACCGCGAGGCAGAGCGTGTACGGGGTGAGGCAGGGGTCGCCTTGCGCCGGGAGCTGGGG
AGCCTGAACTCTTACCTGGAGCAGCTGCGGCAGATGGAGAAGGTCCTGGAGGAGGTGGCGGACAAGCCGC
AGACTGAGTTCCTCATGAAATACTGCCTGGTGACCAGCAGGCTGCAGAAGATCCTGGCAGAGGCTCCCCC
ACCCGCCCGTCTGGACATCCAGCTGCCAATTATCTCAGATGACTTCAAATTCCAGGTGTGGAGGAAGATG
TTCCGGGCTCTGATGCCAGCGCTGGAGGAGCTGACCTTTGACCCGAGCTCTGCGCACCCGAGCCTGGTGG
TGTCTTCCTCTGGCCGCCGCGTGGAGTGCTCGGAGCAGAAGGCGCCGCCGGCCGGGGAGGACCCGCGCCA
GTTCGACAAGGCGGTGGCGGTGGTGGCGCACCAGCAGCTCTCCGAGGGCGAGCACTACTGGGAGGTGGAT
GTTGGCGACAAGCCGCGCTGGGCGCTGGGCGTGATCGCGGCCGAGGCCCCCGCCGCGGGCGCCTGCACG
CGGTGCCCTCGCAGGGCCTGTGGCTGCTGGGGCTGCGCGAGGGCAAGATCCTGGAGGCACACGTGGAGGC
CAAGGAGCCGCGCGCTCTGCGCAGCCCCGAGAGGCGGCCCACGCGCATTGGCCTTTACCTGAGCTTCGGC
GACGGCGTCCTCTCCTTCTACGATGCCAGCGACGCCGACGCGCTCGTGCCGCTTTTGCCTTCCACGAGC
GCCTGCCCAGGCCCGTGTACCCCTTCTTCGACGTGTGCTGGCACGACAAGGGCAAGAATGCCCAGCCGCT
GCTGCTCGTGGGTCCCGAAGGCGCCGAGGCCTGA (SEQ ID NO: 13)

Fig. 8

```
MSAAPGLLRQELSCPLCLQLFDAPVTAECGHSFCRACLIRVAGE
PAADGTVACPCCQAPTRPQALSTNLQLSRLVEGLAQVPQGHCEEHLDPLSIYCEQDRT
LVCGVCASLGSHRGHRLLPAAEAQARLKTQLPQQKMQLQEACMRKEKTVAVLEHQLVE
VEETVRQFRGAVGEQLGKMRMFLAALESSLDREAERVRGDAGVALRRELSSLNSYLEQ
LRQMEKVLEEVADKPQTEFLMKFCLVTSRLQKILSEAPPPARLDIQLPVISDDFKFQV
WKKMFRALMPALEELTFDPSSAHPSLVVSSSGRRVECSDQKAPPAGEDTRQFDKAVAV
VAQQLLSQGEHYWEVEVGDKPRWALGVMAADASRRGRLHAVPSQGLWLLGLRDGKILE
AHVEAKEPRALRTPERPPARIGLYLSFADGVLAFYDASNPDVLTPIFSFHERLPGPVY
PIFDVCWHDKGKNAQPLLLVGPEQEQA(SEQ ID NO: 8)
```

```
ATGTCGGCTGCACCCGGCCTTCTGCGTCAGGAACTGTCCTGCCCACTGTGCTTGCAGCTGTTCGATGCGC
CAGTGACGGCTGAGTGTGGCCACAGTTTCTGCCGTGCCTGCCTGATCCGGGTGGCAGGGGAGCCTGCTGC
GGACGGCACAGTTGCCTGTCCCTGTTGTCAGGCACCTACACGGCCGCAGGCTCTAAGCACTAACCTCCAG
TTGTCACGCCTTGTGGAGGGTTTGGCGCAAGTGCCCCAAGGCCACTGCGAGGAACACCTGGATCCACTGA
GCATCTACTGCGAGCAGGACCGCACACTTGTGTGTGGTGTGTGTGCCTCGCTCGGTTCTCACCGTGGTCA
TCGTCTCCTGCCTGCCGCTGAAGCCCAAGCACGCCTCAAGACACAGCTTCCACAGCAGAAGATGCAGCTG
CAGGAGGCATGCATGCGCAAGGAGAAGACTGTAGCGGTGCTGGAGCATCAGCTGGTGGAGGTGGAGGAGA
CAGTGCGCCAGTTCCGGGGAGCTGTCGGGGAGCAGCTGGGGAAGATGCGGATGTTCCTGGCTGCCCTAGA
AAGTTCTCTGGACCGTGAAGCAGAAAGGGTTCGGGGTGATGCTGGGGTTGCCTTGCGTCGGGAGCTGTCA
AGCCTGAACTCTTACCTAGAGCAACTGAGGCAGATGGAGAAGGTGCTGGAGGAGGTGGCTGACAAGCCAC
AGACAGAATTCCTCATGAAATTCTGCCTGGTAACCAGCAGGCTGCAGAAGATCCTGTCAGAGGCACCACC
ACCGGCAAGGCTAGATATCCAGCTGCCTGTCATCTCAGATGACTTCAAATTCCAGGTGTGGAAGAAGATG
TTCCGGGCTCTGATGCCAGCGCTGGAGGAACTGACTTTTGACCCCAGCTCTGCGCACCCGAGCCTGGTGG
TGTCCTCCTCTGGTCGCCGAGTGGAGTGCTCAGACCAGAAGGCGCCGCCAGCGGGAGAAGACACGCGTCA
GTTCGACAAGGCAGTAGCGGTGGTGGCGCAGCAGCTGCTGTCACAGGGCGAGCACTATTGGGAGGTGGAG
GTGGGCGACAAACCACGCTGGGCCCTGGGAGTGATGGCGGCTGACGCTTCCCGCCGTGGCCGGCTGCACG
CGGTGCCCTCACAGGGGCTGTGGCTGCTGGGTCTGCGCGATGGCAAGATCCTGGAGGCGCACGTGGAGGC
CAAGGAGCCGCGGGCACTGCGCACCCCAGAGAGGCCTCCGGCGCGCATTGGCCTCTACCTAAGCTTCGCA
GATGGCGTCCTGGCTTTCTATGATGCGAGCAACCCCGACGTACTTACGCCAATCTTTTCTTTCCACGAGC
GTCTGCCCGGGCCGGTGTACCCCATCTTTGACGTGCTGGCACGACAAGGGCAAGAATGCCCAGCCCCT
GCTGCTTGTGGGGCCGGAGCAGGAACAGGCCTGA(SEQ ID NO: 14)
```

Fig. 9

```
MSTAPGLLRQELSCPLCLQLFDAPVTAECGHSFCRACLIRVAGE
PADDGTVACPCCQASTRPQALSTNLQLARLVEGLAQVPQGHCEEHLDPLSIYCEQDRT
LVCGVCASLGSHRGHRLLPAAEAHARLKTQLPQQKAQLQEACMRKEKSVAVLEHQLVE
VEETVRQFRGAVGEQLGKMRMFLAALESSLDREAERVRGEAGVALRRELSSLNSYLEQ
LRQMEKVLEEVADKPQTEFLMKFCLVTSRLQKILSEAPPPARLDIQLPVISDDFKFQV
WKKMFRALMPELEELTFDPSSAHPSLVVSASGRRVECSEQKAPPAGEDTCQFDKTVAV
VAKQLLSQGEHYWEVEVGDKPRWALGVMAADASRRGRLHAVPSQGLWLLGLRDGKILE
AHVEAKEPRALRTPERPPARIGLYLSFADGVLTFYDASNTDALTPLFSFHERLPGPVY
PMFDVCWHDKGKNSQPLLLVGPDSEQA(SEQ ID NO: 9)
```

```
ATGTCGACTGCACCAGGCCTTTTGCGCCAGGAACTGTCTTGCCCGCTGTGCTTGCAGCTGTTCGATGCAC
CAGTGACCGCTGAGTGTGGCCACAGTTTCTGCCGTGCCTGCCTGATCCGTGTGGCAGGGGAGCCTGCCGA
CGATGGCACGGTTGCCTGTCCCTGTTGTCAGGCATCTACTCGGCCACAGGCGCTAAGCACTAACCTCCAG
TTGGCACGCCTTGTGGAGGGTTTGGCACAAGTGCCCCAAGGCCACTGCGAGGAACACCTGGATCCACTGA
GCATCTACTGCGAGCAGGACCGCACACTTGTGTGTGGTGTGTGTGCCTCTCTCGGTTCACACCGTGGTCA
CCGTCTTCTGCCTGCCGCAGAAGCCCATGCACGTCTCAAGACACAGCTTCCACAACAGAAGGCCCAGCTG
CAGGAGGCATGCATGCGCAAGGAGAAGAGTGTAGCAGTCCTGGAGCATCAGCTGGTGGAGGTGGAGGAGA
CCGTGCGTCAGTTCCGGGGAGCTGTTGGGGAGCAGCTGGGGAAGATGCGGATGTTCCTGGCTGCCCTAGA
AAGTTCTTTGGACCGTGAAGCAGAAAGGGTTCGAGGTGAGGCAGGGGTTGCCTTGCGGCGGGAGCTGTCA
AGCCTGAACTCTTACCTGGAGCAACTGAGGCAGATGGAGAAGGTGCTGGAGGAGGTGGCTGACAAGCCAC
AGACAGAATTCCTCATGAAATTCTGCCTGGTGACCAGCAGGCTGCAGAAGATTCTGTCAGAGGCACCACC
CCCAGCAAGGCTAGATATCCAGCTGCCTGTCATCTCAGATGACTTCAAATTCCAGGTGTGGAAGAAGATG
TTCCGGGCTCTGATGCCAGAGTTGGAGGAACTGACTTTTGACCCCAGCTCTGCGCACCCGAGCCTGGTGG
TGTCCGCCTCTGGTCGCCGAGTGGAGTGCTCGGAGCAGAAGGCGCCGCCAGCAGGAGAAGACACGTGCCA
GTTCGACAAGACGGTAGCGGTAGTGGCGAAGCAGCTGCTGTCACAGGGGGAGCACTACTGGGAGGTGGAG
GTGGGCGACAAGCCACGCTGGGCCCTGGGTGTGATGGCGGCTGACGCTTCCCGTCGTGGCCGCCTGCACG
CGGTGCCCTCACAGGGGCTGTGGTTGCTCGGCCTGCGCGATGGCAAGATCCTGGAGGCACACGTGGAGGC
CAAGGAGCCACGGGCACTGCGCACCCCAGAGAGGCCACCAGCGCGCATTGGCCTCTACCTAAGCTTTGCA
GATGGCGTCCTGACTTTCTATGATGCAAGCAACACCGACGCGCTTACACCGCTCTTTTCTTTCATGAGC
GTCTGCCTGGGCCGGTGTACCCCATGTTTGACGTGTGCTGGCACGACAAGGGCAAGAATTCTCAGCCGCT
GTTGCTCGTGGGGCCAGACAGTGAGCAGGCCTGA (SEQ ID NO: 15)
```

Fig. 10

MSAAPGLLHQELSCPLCLQLFDAPVTAECGHSFCRACLGRVAGE
PAADGTVLCPCCQAPTRPQALSTNLQLARLVEGLAQVPQGHCEEHLDPLSIYCEQDRA
LVCGVCASLGSHRGHRLLPAAEAHARLKTQLPQQKLQLQEACMRKEKSVAVLEHQLVE
VEETVRQFRGAVGEQLGKMRVFLAALEGSLDREAERVRGEAGVALRRELGSLNSYLEQ
LRQMEKVLEEVADKPQTEFLMKYCLVTSRLQKILAEAPPPARLDIQLPIISDDFKFQV
WRKMFRALMPALEELTFDPSSAHPSLVVSSSGRRVECSEQKAPPAGEDPRQFDKAVAV
VAHQQLSEGEHYWEVEVGDKPRWALGVIAAEGPRRGRLHAVPSQGLWLLGLREGKILE
AHVEAKEPRALRSPERRPTRIGLYLSFGDGVLSFYDASDADALVPLFAFHERLPGPVY
PFFDVCWHDKGKNSQPLLLVGSEGAEA (SEQ ID NO: 10)

ATGTCGGCTGCGCCGGGCCTCCTGCACCAGGAGCTGTCCTGCCCGCTGTGCCTGCAGCTGTTCGACGCGC
CCGTGACAGCCGAGTGCGGCCACAGTTTCTGTCGCGCCTGCCTGGGCCGCGTGGCCGGGGAACCGGCGGC
GGATGGCACCGTTCTCTGCCCCTGCTGTCAGGCCCCCACGCGGCCGCAGGCACTCAGCACCAACCTGCAG
CTGGCGCGCCTGGTGGAGGGGCTGGCCCAGGTGCCGCAGGGCCACTGCGAGGAGCACCTGGACCCGCTGA
GCATCTACTGTGAGCAGGACCGCGCGCTGGTGTGCGGAGTGTGCGCCTCACTCGGCTCGCACCGCGGTCA
TCGCCTGCTGCCCGCCGCCGAGGCCCACGCACGCCTCAAGACGCAGCTGCCACAGCAGAAACTGCAGCTG
CAGGAGGCATGCATGCGCAAGGAGAAGAGTGTAGCTGTGCTGGAGCATCAGTTGGTGGAAGTGGAGGAGA
CAGTGCGTCAGTTCCGGGGGGCCGTGGGGGAGCAGCTGGGCAAGATGCGGGTGTTCCTGGCTGCACTGGA
GGGCTCCTTGGACCGTGAGGCAGAGCGTGTGCGGGGTGAGGCAGGGGTCGCCTTGCGCCGGGAGCTGGGG
AGCCTGAACTCTTACCTGGAGCAGCTGCGGCAGATGGAGAAGGTGCTGGAGGAGGTGGCCGACAAGCCGC
AGACTGAGTTCCTAATGAAATACTGCCTGGTGACCAGCAGGCTGCAGAAGATCCTGGCAGAGGCTCCCCC
ACCCGCCCGTCTGGACATCCAGCTGCCAATCATCTCAGATGACTTCAAATTCCAGGTGTGGAGGAAGATG
TTCCGGGCTCTGATGCCAGCGCTGGAGGAGCTGACCTTTGACCCGAGCTCTGCGCACCCCAGCCTGGTGG
TGTCTTCCTCCGGCCGCCGCGTGGAGTGCTCGGAGCAGAAGGCGCCGCCGGCGGGGGAGGACCCGCGCCA
GTTCGACAAGGCGGTAGCGGTGGTGGCGCACCAGCAGCTCTCCGAGGGCGAACACTACTGGGAGGTGGAG
GTGGGCGACAAGCCGCGCTGGGCGCTGGGTGTGATCGCGGCCGAGGGGCCCCGTCGCGGGCGCCTGCACG
CGGTGCCCTCGCAGGGCCTGTGGCTGCTGGGGCTGCGTGAGGGCAAGATCCTGGAGGCTCACGTGGAGGC
CAAGGAGCCGCGCGCTCTGCGCAGCCCCGAGCGGCGGCCCACGCGCATCGGCCTCTACCTGAGCTTCGGC
GACGGCGTCCTCTCCTTCTACGATGCCAGCGACGCCGACGCGCTCGTGCCGCTTTTTGCCTTCCACGAGC
GCCTGCCTGGGCCCGTGTACCCCTTCTTCGACGTGTGCTGGCACGACAAGGGCAAGAACTCCCAGCCGCT
GCTGCTCGTGGGGTCCGAAGGCGCCGAAGCCTGA (SEQ ID NO: 16)

Fig. 11

MSAAPGLLHQELSCPLCLQLFDAPVTAECGHSFCRACLGRVAGE
PAADGTVLCPSCQAPTRPQALSTNQQLARLVEGLAQVPQGHCEEHLDPLSIYCEQDRV
LVCGVCASLGSHRGHRLLPAAEAHARLKTQLPQQKLQLQEACMRKEKSVGVLEQQLVE
VEETVRQFRGAVGEQLGKMRLFLAALEGSLDREAERVRGEAGVALRRELGSLKSYLEQ
LRQMEKVLEEVADKPQTEFLMKYCLVTSRLQKILAEAPPPARLDIQLPVISDDFKFQV
WRKMFRALMPAMQELTFDPSTAHPSLVLSASGRRVECSEQKAPPAGEDPRQFDKAVAV
VTHQLLSEGEHYWEVEVGDKPRWALGVIGAQAGRRGRLHAVPSQGLWLLGLREGKILE
AHVEAKEPRALRTPERRPSRIGIYLSFADGVLSFYDASDADALELLFAFHERLPGPVY
PFFDVCWHDKGKNAQPLLLVGPDSGGEA (SEQ ID NO: 11)

ATGTCAGCTGCGCCCGGCCTCCTGCACCAGGAGCTGTCCTGTCCGCTGTGCCTGCAGCTGTTCGATGCGC
CGGTGACGGCTGAGTGCGGCCACAGCTTCTGCCGCGCCTGCCTGGGCCGCGTGGCAGGGGAGCCAGCCGC
GGATGGCACGGTGCTCTGCCCCAGCTGCCAGGCACCCACGCGGCCGCAGGCGCTCAGCACCAACCAGCAG
CTGGCGCGCCTGGTGGAGGGGCTGGCGCAGGTGCCGCAGGGCCACTGCGAGGAGCACCTAGACCCGCTCA
GCATCTACTGCGAGCAGGACCGCGTGCTCGTGTGCGGCGTCTGCGCCTCGCTGGGTTCGCACCGCGGCCA
CCGCCTGCTGCCCGCCGCCGAAGCCCATGCGCGCCTTAAGACGCAGCTCCCGCAGCAGAAGCTGCAGCTG
CAGGAGGCGTGTATGCGGAAGGAGAAGAGCGTGGGTGTGCTGGAGCAACAACTGGTGGAAGTGGAGGAGA
CGGTGCGTCAGTTCCGGGGGGCAGTGGGGGAGCAGCTGGGCAAGATGCGGTTGTTCCTGGCTGCACTGGA
GGGCTCCTTGGACCGAGAAGCAGAGCGTGTGCGGGGTGAGGCGGGGGTCGCCTTGCGGAGGGAGCTGGGG
AGCCTGAAGTCTTACTTGGAGCAGCTGCGGCAGATGGAGAAGGTGCTGGAGGAGGTGGCAGACAAGCCCC
AGACCGAGTTCCTCATGAAATACTGCCTGGTGACCAGCAGGCTGCAGAAGATCCTGGCAGAGGCGCCCCC
ACCTGCCCGCCTGGACATTCAGCTGCCTGTCATCTCAGACGACTTCAAATTCCAGGTGTGGAGAAAGATG
TTCCGGGCCCTGATGCCAGCGATGCAGGAGCTGACCTTTGACCCCAGCACGGCCCACCCGAGCCTGGTGC
TGTCGGCCTCGGGCCGCCGCGTGGAGTGCTCGGAGCAGAAGGCGCCGCCGGCCGGAGAGGACCCGCGCCA
GTTCGACAAGGCGGTGGCGGTGGTGACGCACCAGCTGCTGTCGGAAGGCGAGCACTACTGGGAGGTGGAG
GTGGGCGACAAGCCACGCTGGGCGCTGGGCGTGATCGGGGCCCAGGCCGGTCGCCGCGGCCGGCTGCACG
CCGTGCCCTCGCAGGGCCTCTGGCTGCTCGGGCTGCGCGAGGGCAAGATCCTGGAGGCTCACGTCGAGGC
CAAGGAGCCGCGCGCCCTGCGCACCCCGGAGAGGCGGCCGTCGCGCATCGGGATCTACCTGAGCTTCGCG
GATGGCGTCCTCTCGTTCTACGACGCCAGCGACGCCGACGCGCTGGAGCTGCTCTTCGCCTTCCACGAAC
GCCTGCCGGGCCCCGTGTACCCCTTCTTCGACGTGTGCTGGCACGACAAGGGCAAGAACGCTCAGCCGCT
CCTGCTGGTGGGGCCCGACAGCGGCGGGGAGGCCTGA (SEQ ID NO: 17)

Fig. 12

MSAAPGLLHQELSCPLCLQLFDAPVTAECGHSFCRACLSRVAGE
PAADGTVPCPCCQALTRPQALSTNQQLARLVEGLAQVPQGHCEEHLDPLSIYCEQDRA
LVCGVCASLGSHRGHRLLPAAEAHARLKTQLPQQKLQLQEACMRKEKSVALLEHQLME
VEEMVRQFRGAVGEQLGKMRVFLAALEGSLDREAERVRGEAGVALRRELGSLNSYLEQ
LRQMEKVLEEVADKPQTEFLMKYCLVTSRLQKILAEAPPPARLDIQLPVISDDFKFQV
WRKMFRALMPVTKELTFDPSSAHPSLVLSPSGRRVECSDQKAPPAGEDPCQFDKAVAV
VAQQVLSDGEHYWEVQVGEKPRWALGVIAAQASRRGRLHAVPSQGLWLLGLRDGKILE
AHVEAKEPRALRTPERRPTRIGIYLSFGDGVLSFYDASDPDALELLFAFHERLPGPVY
PFFDVCWHDKGKNAQPLLLVGPDGEEA (SEQ ID NO: 12)

ATGTCGGCCGCGCCGGGCCTCCTGCACCAGGAGCTGTCCTGCCCGCTCTGCCTGCAGCTGTTTGACGCGC
CGGTGACCGCCGAGTGCGGCCACAGTTTCTGCCGCGCCTGCCTGAGCCGCGTGGCTGGGGAGCCGGCGGC
GGACGGCACCGTGCCCTGCCCGTGCTGCCAGGCACTCACGCGGCCACAGGCGCTCAGCACCAACCAGCAG
CTGGCGCGCCTGGTGGAGGGGCTGGCGCAGGTGCCGCAGGGCCACTGCGAGGAGCACCTAGACCCGCTCA
GCATCTACTGCGAGCAGGATCGAGCGCTCGTGTGCGGCGTGTGCGCCTCGCTCGGCTCGCACCGCGGCCA
CCGCCTGCTGCCCGCCGCCGAAGCCCACGCGCGCCTCAAGACACAGCTGCCACAGCAGAAACTGCAGCTG
CAGGAGGCATGTATGCGCAAGGAGAAGAGTGTGGCTCTGCTGGAGCATCAGCTCATGGAAGTGGAGGAGA
TGGTGCGTCAGTTCCGGGGGGCTGTAGGGGAGCAGCTGGGCAAGATGCGGGTGTTCCTGGCTGCACTGGA
GGGCTCCTTGGACCGTGAGGCAGAGCGCGTGCGGGGAGAGGCAGGGGTTGCCCTGCGGCGGGAGCTGGGG
AGCCTGAACTCTTACCTGGAGCAGTTGCGTCAGATGGAGAAGGTGCTGGAGGAGGTGGCCGACAAGCCAC
AGACTGAGTTCCTCATGAAATACTGCCTGGTGACCAGCAGGCTACAGAAGATCCTGGCAGAAGCACCACC
GCCTGCCCGTTTGGACATCCAGCTGCCTGTCATCTCAGATGACTTCAAATTCCAGGTGTGGAGGAAGATG
TTCCGGGCTCTGATGCCAGTTACAAAGGAGCTGACCTTTGACCCGAGCTCTGCGCACCCGAGCCTGGTGC
TGTCTCCCTCCGGTCGCCGCGTGGAGTGCTCGGACCAGAAGGCGCCGCCGGCCGGGGAGGATCCGTGCCA
GTTCGACAAGGCCGTGGCGGTGGTGGCGCAGCAGGTGCTGTCCGACGGCGAGCACTACTGGGAGGTGCAG
GTGGGCGAGAAGCCGCGCTGGGCCCTCGGCGTGATCGCGGCCCAGGCCAGCCGCCGCGGCCGGCTGCACG
CCGTCCCCTCGCAGGGCCTCTGGCTGCTCGGGCTGCGGGACGGCAAGATCCTGGAGGCGCACGTCGAAGC
CAAGGAGCCGCGCGCGCTGCGCACCCCGGAGAGGCGGCCCACGCGCATCGGGATCTACCTAAGCTTCGGC
GACGGAGTCCTCTCCTTTTATGATGCCAGTGACCCCGACGCCCTCGAGCTGCTCTTTGCCTTCCACGAGC
GCCTGCCCGGCCCCGTGTACCCCTTCTTCGACGTATGCTGGCACGACAAGGGCAAAAATGCTCAGCCGCT
GCTGCTGGTGGGGCCTGATGGCGAGGAGGCCTGA (SEQ ID NO: 18)

Fig. 13

A
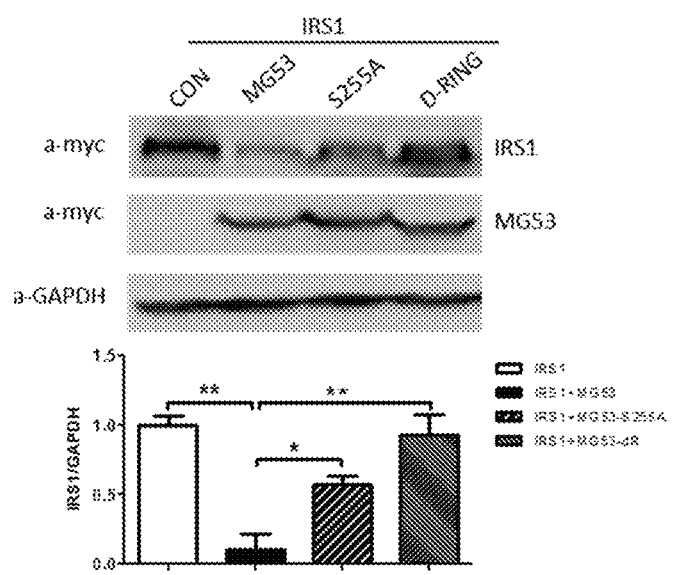
B
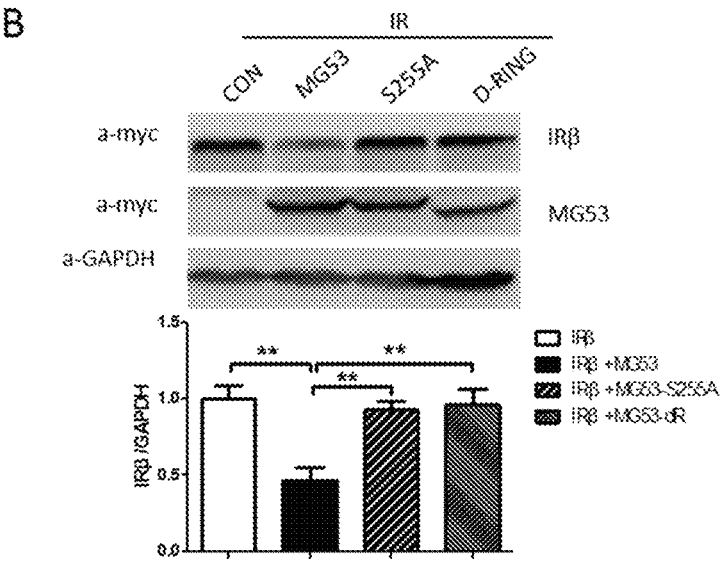
Fig. 16

MSAAPGLLHQ ELSCPLCLQL FDAPVTAECG HSFCRACLGR VAGEPAADGT VLCPCCQAPT
RPQALSTNLQ LARLVEGLAQ VPQGHCEEHL DPLSIYCEQD RALVCGVCAS LGSHRGHRLL
PAAEAHARLK TQLPQQKLQL QEACMRKEKS VAVLEHQLVE VEETVRQFRG AVGEQLGKMR
VFLAALEGSL DCEAERVRGE AGVALRRELG SLNSYLEQLR QMEKVLEEVA DKPQTEFLMK
YCLVTSRLQK ILAESPPPAR LDIQLPIISD DFKFQVWRKM FRALMPALEE LTFDPSSAHP
SLVVSSSGRR VECSEQKAPP AGEDPRQFDK AVAVVAHQQL SEGEHYWEVD VGDKPRWALG
VIAAEAPRRG RLHAVPSQGL WLLGLREGKI LEAHVEAKEP RALRSPERRP TRIGLYLSFG
DGVLSFYDAS DADALVPLFA FHERLPRPVY PFFDVCWHDK GKNAQPLLLV GPEGAEA (SEQ ID NO: 139)

atgtcggctg cgcccggcct cctgcaccag gagctgtcct gcccgctgtg cctgcagctg
ttcgacgcgc ccgtgacagc cgagtgcggc cacagtttct gccgcgcctg cctaggccgc
gtggccgggg agccggcggc ggatggcacc gttctctgcc cctgctgcca ggccccacg
cggccgcagg cactcagcac caacctgcag ctggcgcgcc tggtggaggg ctggcccag
gtgccgcagg ccactgcga ggagcacctg gacccgctga gcatctactg cgagcaggac
cgcgcgctgg tgtgcggagt gtgcgcctca ctcggctcgc accgcggtca tcgcctcctg
cctgccgccg aggcccacgc acgcctcaag acacagctgc cacagcagaa actgcagctg
caggaggcat gcatgcgtaa ggagaagagt gtggctgtgc tggagcatca gctggtggag
gtggaggaga cagtgcgtca gttccggggg gccgtggggg agcagctggg caagatgcgg
gtgttcctgg ctgcactgga gggctccttg gactgcgagg cagagcgtgt acggggtgag
gcaggggtcg ccttgcgccg ggagctgggg agcctgaact cttacctgga gcagctgcgg
cagatggaga aggtcctgga ggaggtggcg gacaagccgc agactgagtt cctcatgaaa
tactgcctgg tgaccagcag gctgcagaag atcctggcag agtctccccc acccgccgt
ctggacatcc agctgccaat tatctcagat gacttcaaat tccaggtgtg gaggaagatg
ttccgggctc tgatgccagc gctggaggag ctgacctttg acccgagctc tgcgcacccg
agcctggtgg tgtcttcctc tggccgccgc gtggagtgct cggagcagaa ggcgccgcg
gccggggagg acccgcgcca gttcgacaag gcggtggcgg tggtggcgca ccagcagctc
tccgagggcg agcactactg ggaggtggat gttggcgaca agccgcgctg ggcgctgggc
gtgatcgcgg ccgaggcccc ccgccgggg cgcctgcacg cggtgcctc gcagggcctg
tggctgctgg ggctgcgcga gggcaagatc ctggaggcac acgtggaggc caaggagccg
cgcgctctgc gcagccccga gaggcggccc acgcgcattg cctttacct gagcttcggc
gacggcgtcc tctccttcta cgatgccagc gacgccgacg cgctcgtgcc gcttttgcc
ttccacgagc gcctgccag gcccgtgtac cccttcttcg acgtgtgctg gcacgacaag
ggcaagaatg cccagccgct gctgctcgtg ggtcccgaag cgccgaggc ctga (SEQ ID NO: 143)

Fig. 20

```
MRKEKSVAVL EHQLVEVEET VRQFRGAVGE QLGKMRVFLA ALEGSLDREA ERVRGEAGVA
LRRELGSLNS YLEQLRQMEK VLEEVADKPQ TEFLMKYCLV TSRLQKILAE SPPPARLDIQ
LPIISDDFKF QVWRKMFRAL MPALEELTFD PSSAHPSLVV SSSGRRVECS EQKAPPAGED
PRQFDKAVAV VAHQQLSEGE HYWEVDVGDK PRWALGVIAA EAPRRGRLHA VPSQGLWLLG
LREGKILEAH VEAKEPRALR SPERRPTRIG LYLSFGDGVL SFYDASDADA LVPLFAFHER
LPRPVYPFFD VCWHDKGKNA QPLLLVGPEG AEA     (SEQ ID NO: 140)
```

```
atgcgcaagg agaagagtgt ggctgtgctg gagcatcagc tggtggaggt ggaggagaca
gtgcgtcagt tccgggggc cgtgggggag cagctgggca agatgcgggt gttcctggct
gcactggagg gctccttgga ccgcgaggca gagcgtgtac ggggtgaggc aggggtcgcc
ttgcgccggg agctggggag cctgaactct tacctggagc agctgcggca gatggagaag
gtcctggagg aggtggcgga caagccgcag actgagttcc tcatgaaata ctgcctggtg
accagcaggc tgcagaagat cctggcagag tctcccccac ccgcccgtct ggacatccag
ctgccaatta tctcagatga cttcaaattc caggtgtgga ggaagatgtt ccgggctctg
atgccagcgc tggaggagct gacctttgac ccgagctctg cgcacccgag cctggtggtg
tcttcctctg gccgccgcgt ggagtgctcg gagcagaagg cgccgccggc cggggaggac
ccgcgccagt tcgacaaggc ggtggcggtg gtggcgcacc agcagctctc cgagggcgag
cactactggg aggtggatgt tggcgacaag ccgcgctggg cgctgggcgt gatcgcggcc
gaggcccccc gccgcgggcg cctgcacgcg gtgccctcgc agggcctgtg gctgctgggg
ctgcgcgagg gcaagatcct ggaggcacac gtggaggcca aggagccgcg cgctctgcgc
agccccgaga ggcggcccac gcgcattggc ctttacctga gcttcggcga cggcgtcctc
tccttctacg atgccagcga cgccgacgcg ctcgtgccgc tttttgcctt ccacgagcgc
ctgccaggc cgtgtaccc cttcttcgac gtgtgctggc acgacaaggg caagaatgcc
cagccgctgc tgctcgtggg tcccgaaggc gccgaggcct ga (SEQ ID NO: 144)
```

Fig. 21

```
MRKEKSVAVL EHQLVEVEET VRQFRGAVGE QLGKMRVFLA ALEGSLDREA ERVRGEAGVA
LRRELGSLNS YLEQLRQMEK VLEEVADKPQ TEFLMKYCLV TSRLQKILAE SPPPARLDIQ
LPIISDDFKF QVWRKMFRAL MPALEELTFD PSSAHPSLVV SSSGRRVECS GQKAPPAGED
PRQFDKAVAV VAHQQLSEGE HYWEVDVGDK PRWALGVIAA EAPRRGRLHA VPSQGLWLLG
LREGKILEAH VEAKEPRALR SPERRPTRIG LYLSFGDGVL SFYDASDADA LVPLFAFHER
LPRPVYPFFD VCWHDKGKNA QPLLLVGPEG AEA   (SEQ ID NO: 141)

atgcgtaagg agaagagtgt ggctgtgctg gagcatcagc tggtggaggt ggaggagaca
gtgcgtcagt tccggggggc cgtgggggag cagctgggca agatgcgggt gttcctggct
gcactggagg gctccttgga ccgcgaggca gagcgtgtac ggggtgaggc aggggtcgcc
ttgcgccggg agctggggag cctgaactct tacctggagc agctgcggca gatggagaag
gtcctggagg aggtggcgga caagccgcag actgagttcc tcatgaaata ctgcctggtg
accagcaggc tgcagaagat cctggcagag tctcccccac ccgcccgtct ggacatccag
ctgccaatta tctcagatga cttcaaattc caggtgtgga ggaagatgtt ccgggctctg
atgccagcgc tggaggagct gacctttgac ccgagctctg cgcacccgag cctggtggtg
tcttcctctg gccgccgcgt ggagtgctcg gggcagaagg cgccgccggc cggggaggac
ccgcgccagt tcgacaaggc ggtggcggtg gtggcgcacc agcagctctc cgagggcgag
cactactggg aggtggatgt ggcgacaag ccgcgctggg cgctgggcgt gatcgcggcc
gaggcccccc gccgcgggcg cctgcacgcg gtgccctcgc agggcctgtg gctgctgggg
ctgcgcgagg gcaagatcct ggaggcacac gtggaggcca aggagccgcg cgctctgcgc
agccccgaga ggcggcccac gcgcattggc ctttacctga gcttcggcga cggcgtcctc
tccttctacg atgccagcga cgccgacgcg ctcgtgccgc ttttgccttt ccacgagcgc
ctgcccaggc ccgtgtaccc cttcttcgac gtgtgctggc acgacaaggg caagaatgcc
cagccgctgc tgctcgtggg tcccgaaggc gccgaggcct ga (SEQ ID NO: 145)
```

Fig. 22

```
MSAAPGLLHQ ELSCPLCLQL FDAPVTAECG HSFCRACLGR VAGEPAADGT VLCPCCQAPT
RPQALSTNLQ LARLVEGLAQ VPQGHCEEHL DPLSIYCEQD RALVCGVCAS LGSHRGHRLL
PAAEAHARLK TQLPQQKLQL QEACMRKEKS VAVLEHQLVE VEETVRQFRG AVGEQLGKMR
VFLAALEGSL DREAERVRGE AGVALRRELG SLNSYLEQLR QMEKVLEEVA DKPQTEFLMK
YCLVTSRLQK ILAESPPPAR LDIQLPIIS  (SEQ ID NO: 142)

atgtcggctg cgcccggcct cctgcaccag gagctgtcct gcccgctgtg cctgcagctg
ttcgacgcgc ccgtgacagc cgagtgcggc cacagtttct gccgcgcctg cctaggccgc
gtggccgggg agccggcggc ggatggcacc gttctctgcc cctgctgcca ggcccccacg
cggccgcagg cactcagcac caacctgcag ctggcgcgcc tggtggaggg gctggcccag
gtgccgcagg gccactgcga ggagcacctg gacccgctga gcatctactg cgagcaggac
cgcgcgctgg tgtgcggagt gtgcgcctca ctcggctcgc accgcggtca tcgcctcctg
cctgccgccg aggcccacgc acgcctcaag acacagctgc cacagcagaa actgcagctg
caggaggcat gcatgcgtaa ggagaagagt gtggctgtgc tggagcatca gctggtggag
gtggaggaga cagtgcgtca gttccggggg gccgtggggg agcagctggg caagatgcgg
gtgttcctgg ctgcactgga gggctccttg gaccgcgagg cagagcgtgt acggggtgag
gcaggggtcg ccttgcgccg ggagctgggg agcctgaact cttacctgga gcagctgcgg
cagatggaga aggtcctgga ggaggtggcg gacaagccgc agactgagtt cctcatgaaa
tactgcctgg tgaccagcag gctgcagaag atcctggcag agtctccccc acccgcccgt
ctggacatcc agctgccaat tatctcctga (SEQ ID NO: 146)
```

Fig. 23

MSAAPGLLHQ ELSCPLCLQL FDAPVTAECG HSFCRACLGR VAGEPAADGT VLCPCCQAPT
RPQALSTNLQ LARLVEGLAQ VPQGHCEEHL DPLSIYCEQD RALVCGVCAS LGSHRGHRLL
PAAEAHARLK TQLPQQKLQL QEACMRKEKS VAVLEHQLVE VEETVRQFRG AVGEQLGKMR
VFLAALEGSL DCEAERVRGE AGVALRRELG SLNSYLEQLR QMEKVLEEVA DKPQTEFLMK
YCLVTSRLQK ILAEAPPPAR LDIQLPIISD DFKFQVWRKM FRALMPALEE LTFDPSSAHP
SLVVSSSGRR VECSEQKAPP AGEDPRQFDK AVAVVAHQQL SEGEHYWEVD VGDKPRWALG
VIAAEAPRRG RLHAVPSQGL WLLGLREGKI LEAHVEAKEP RALRSPERRP TRIGLYLSFG
DGVLSFYDAS DADALVPLFA FHERLPRPVY PFFDVCWHDK GKNAQPLLLV GPEGAEA (SEQ ID NO: 147)

atgtcggctg cgcccggcct cctgcaccag gagctgtcct gcccgctgtg cctgcagctg
ttcgacgcgc ccgtgacagc cgagtgcggc cacagtttct gccgcgcctg cctaggccgc
gtggccgggg agccggcggc ggatggcacc gttctctgcc cctgctgcca ggccccacg
cggccgcagg cactcagcac caacctgcag ctggcgcgcc tggtggaggg gctggcccag
gtgccgcagg gccactgcga ggagcacctg gacccgctga gcatctactg cgagcaggac
cgcgcgctgg tgtgcggagt gtgcgcctca ctcggctcgc accgcggtca tcgcctcctg
cctgccgccg aggcccacgc acgcctcaag acacagctgc cacagcagaa actgcagctg
caggaggcat gcatgcgtaa ggagaagagt gtggctgtgc tggagcatca gctggtggag
gtggaggaga cagtgcgtca gttccggggg gccgtggggg agcagctggg caagatgcgg
gtgttcctgg ctgcactgga gggctccttg gactgcgagg cagagcgtgt acggggtgag
gcagggtcg ccttgcgccg ggagctgggg agcctgaact cttacctgga gcagctgcgg
cagatggaga aggtcctgga ggaggtggcg acaagccgc agactgagtt cctcatgaaa
tactgcctgg tgaccagcag gctgcagaag atcctggcag aggctccccc accgccgct
ctggacatcc agctgccaat tatctcagat gacttcaaat tccaggtgtg gaggaagatg
ttccgggctc tgatgccagc gctggaggag ctgacctttg acccgagctc tgcgcacccg
agcctggtgg tgtcttcctc tggccgccgc gtggagtgct cggagcagaa ggcgccgccg
gccggggagg accccgcca gttcgacaag gcggtggcgg tggtggcgca ccagcagctc
tccgaggcg agcactactg ggaggtggat gttggcgaca gccgcgctg ggcgctgggc
gtgatcgcgg ccgaggcccc ccgccgcggg cgcctgcacg cggtgccctc gcagggcctg
tggctgctgg ggctgcgcga gggcaagatc ctggaggcac acgtggaggc caaggagccg
cgcgctctgc gcagccccga gaggcggccc acgcgcattg gcctttacct gagcttcggc
gacggcgtcc tctccttcta cgatgccagc gacgccgacg cgctcgtgcc gcttttgcc
ttccacgagc gcctgcccag gccgtgtac cccttcttcg acgtgtgctg gcacgacaag
ggcaagaatg cccagccgct gctgctcgtg ggtcccgaag gcgccgaggc ctga (SEQ ID NO: 151)

Fig. 24

```
MRKEKSVAVL EHQLVEVEET VRQFRGAVGE QLGKMRVFLA ALEGSLDREA ERVRGEAGVA
LRRELGSLNS YLEQLRQMEK VLEEVADKPQ TEFLMKYCLV TSRLQKILAE APPPARLDIQ
LPIISDDFKF QVWRKMFRAL MPALEELTFD PSSAHPSLVV SSSGRRVECS EQKAPPAGED
PRQFDKAVAV VAHQQLSEGE HYWEVDVGDK PRWALGVIAA EAPRRGRLHA VPSQGLWLLG
LREGKILEAH VEAKEPRALR SPERRPTRIG LYLSFGDGVL SFYDASDADA LVPLFAFHER
LPRPVYPFFD VCWHDKGKNA QPLLLVGPEG AEA     (SEQ ID NO: 148)
```

```
atgcgcaagg agaagagtgt ggctgtgctg gagcatcagc tggtggaggt ggaggagaca
gtgcgtcagt tccggggggc cgtgggggag cagctgggca agatgcgggt gttcctggct
gcactggagg gctccttgga ccgcgaggca gagcgtgtac ggggtgaggc aggggtcgcc
ttgcgccggg agctggggag cctgaactct tacctggagc agctgcggca gatggagaag
gtcctggagg aggtggcgga caagccgcag actgagttcc tcatgaaata ctgcctggtg
accagcaggc tgcagaagat cctggcagag ctcccccac ccgcccgtct ggacatccag
ctgccaatta tctcagatga cttcaaattc caggtgtgga ggaagatgtt ccgggctctg
atgccagcgc tggaggagct gacctttgac ccgagctctc gcacccgag cctggtggtg
tcttcctctg gccgccgcgt ggagtgctcg gagcagaagg cgccgccggc cggggaggac
ccgcgccagt tcgacaaggc ggtggcggtg gtggcgcacc agcagctctc cgagggcgag
cactactggg aggtggatgt tggcgacaag ccgcgctggg cgctgggcgt gatcgcggcc
gaggccccc gccgcgggcg cctgcacgcg gtgccctcgc agggcctgtg gctgctgggg
ctgcgcgagg gcaagatcct ggaggcacac gtggaggcca aggagccgcg cgctctgcgc
agccccgaga ggcggcccac gcgcattggc ctttacctga gcttcggcga cggcgtcctc
tccttctacg atgccagcga cgccgacgcg ctcgtgccgc ttttgccctt ccacgagcgc
ctgccaggc ccgtgtaccc cttcttcgac gtgtgctggc acgacaaggg caagaatgcc
cagccgctgc tgctcgtggg tcccgaaggc gccgaggcct ga (SEQ ID NO: 152)
```

Fig. 25

```
MRKEKSVAVL EHQLVEVEET VRQFRGAVGE QLGKMRVFLA ALEGSLDREA ERVRGEAGVA
LRRELGSLNS YLEQLRQMEK VLEEVADKPQ TEFLMKYCLV TSRLQKILAE APPPARLDIQ
LPIISDDFKF QVWRKMFRAL MPALEELTFD PSSAHPSLVV SSSGRRVECS GQKAPPAGED
PRQFDKAVAV VAHQQLSEGE HYWEVDVGDK PRWALGVIAA EAPRRGRLHA VPSQGLWLLG
LREGKILEAH VEAKEPRALR SPERRPTRIG LYLSFGDGVL SFYDASDADA LVPLFAFHER
LPRPVYPFFD VCWHDKGKNA QPLLLVGPEG AEA   (SEQ ID NO: 149)

atgcgtaagg agaagagtgt ggctgtgctg gagcatcagc tggtggaggt ggaggagaca
gtgcgtcagt tccggggggc cgtgggggag cagctgggca agatgcgggt gttcctggct
gcactggagg gctccttgga ccgcgaggca gagcgtgtac ggggtgaggc aggggtcgcc
ttgcgccggg agctggggag cctgaactct tacctggagc agctgcggca gatggagaag
gtcctggagg aggtggcgga caagccgcag actgagttcc tcatgaaata ctgcctggtg
accagcaggc tgcagaagat cctggcagag gctcccccac ccgcccgtct ggacatccag
ctgccaatta tctcagatga cttcaaattc caggtgtgga ggaagatgtt ccgggctctg
atgccagcgc tggaggagct gacctttgac ccgagctctg cgcacccgag cctggtggtg
tcttcctctg gccgccgcgt ggagtgctcg ggcagaagg cgccgccggc cggggaggac
ccgcgccagt tcgacaaggc ggtggcggtg gtggcgcacc agcagctctc cgagggcgag
cactactggg aggtggatgt ggcgacaag ccgcgctggg cgctgggcgt gatcgcggcc
gaggccccc gccgcgggcg cctgcacgcg gtgccctcgc agggcctgtg gctgctgggg
ctgcgcgagg gcaagatcct ggaggcacac gtggaggcca aggagccgcg cgctctgcgc
agccccgaga ggcggcccac gcgcattggc ctttacctga gcttcggcga cggcgtcctc
tccttctacg atgccagcga cgccgacgcg ctcgtgccgc tttttgcctt ccacgagcgc
ctgcccaggc ccgtgtaccc cttcttcgac gtgtgctggc acgacaaggg caagaatgcc
cagccgctgc tgctcgtggg tcccgaaggc gccgaggcct ga (SEQ ID NO: 153)
```

Fig. 26

```
MSAAPGLLHQ ELSCPLCLQL FDAPVTAECG HSFCRACLGR VAGEPAADGT VLCPCCQAPT
RPQALSTNLQ LARLVEGLAQ VPQGHCEEHL DPLSIYCEQD RALVCGVCAS LGSHRGHRLL
PAAEAHARLK TQLPQQKLQL QEACMRKEKS VAVLEHQLVE VEETVRQFRG AVGEQLGKMR
VFLAALEGSL DREAERVRGE AGVALRRELG SLNSYLEQLR QMEKVLEEVA DKPQTEFLMK
YCLVTSRLQK ILAEAPPPAR LDIQLPIIS  (SEQ ID NO: 150)
```

```
atgtcggctg cgcccggcct cctgcaccag gagctgtcct gcccgctgtg cctgcagctg
ttcgacgcgc ccgtgacagc cgagtgcggc cacagtttct gccgcgcctg cctaggccgc
gtggccgggg agccggcggc ggatggcacc gttctctgcc cctgctgcca ggcccccacg
cggccgcagg cactcagcac caacctgcag ctggcgcgcc tggtggaggg gctggcccag
gtgccgcagg gccactgcga ggagcacctg gacccgctga gcatctactg cgagcaggac
cgcgcgctgg tgtgcggagt gtgcgcctca ctcggctcgc accgcggtca tcgcctcctg
cctgccgccg aggcccacgc acgcctcaag acacagctgc cacagcagaa actgcagctg
caggaggcat gcatgcgtaa ggagaagagt gtggctgtgc tggagcatca gctggtggag
gtggaggaga cagtgcgtca gttccggggg gccgtggggg agcagctggg caagatgcgg
gtgttcctgg ctgcactgga gggctccttg gaccgcgagg cagagcgtgt acggggtgag
gcagggtcg ccttgcgccg ggagctgggg agcctgaact cttacctgga gcagctgcgg
cagatggaga aggtcctgga ggaggtggcg gacaagccgc agactgagtt cctcatgaaa
tactgcctgg tgaccagcag gctgcagaag atcctggcag aggctccccc acccgcccgt
ctggacatcc agctgccaat tatctcctga (SEQ ID NO: 154)
```

Fig. 27

| amino acid positions of full-length MG53 protein (positions 1-*n*) | 1 p s m q n |
|---|---|
| amino acid positions of MG53 subtype 1 (positions *m-n*) | m n |
| amino acid positions of MG53 subtype 2 (positions *1-s*) | 1 s |
| amino acid positions of MG53 subtype 3 (positions *p-q*) | p q |

Fig. 28

MG53 MUTANTS, METHODS OF MAKING THE SAME, AND USES THEREOF

CROSS-REFERENCE TO RELATED APPLICATIONS

This application is a continuation-in-part of PCT/CN2017/093640, filed Jul. 20, 2017, now pending, which claims priority to CN 201610621989.7, filed Aug. 1, 2016, CN 201610847346.4, filed Sep. 23, 2016 and CN 201710560975.3, filed Jul. 11, 2017. The contents of the above-referenced applications are incorporated herein by reference in their entireties for all purposes.

TECHNICAL FIELD

The present invention relates to the biomedical field. In particular, the present invention relates to MG53 mutants, pharmaceutical compositions comprising the MG53 mutants, nucleic acids encoding the MG53 mutants, methods for preparing the MG53 mutants, and uses of the MG53 mutants in the manufacture of medicaments for treating heart diseases, diabetic cerebrovascular diseases, diabetic ocular complications, diabetic neuropathy, diabetic foot, kidney diseases, and diseases associated with cellular and/or tissue damage.

BACKGROUND ART

Mitsugumin 53 (MG53), also known as TRIM72, is a member of the Tripartite motif-containing proteins (TRIM) family. MG53 comprises a TRIM motif at the N-terminus and a SPRY motif at the C-terminus. The TRIM motif consists of successively linked Ring, B-box and coiled-coil domains (see Chuanxi Cai et al., the *Journal of Biological Chemistry*, Vol. 284 (5), 3314-3322 (2009)). MG53 plays a variety of roles throughout the body, but it is mainly expressed in striated muscles, and is essential for maintaining the homeostasis of skeletal muscle and the heart. MG53 was previously found to have cell membrane repair function and cardioprotective function (see, e.g., Chuanxi Cai et al., *Nature Cell Biology*, Vol. 11, 56-64 (2009); CN101797375B). In addition, further studies have found that MG53 also plays a protective role in ischemic preconditioning (IPC) and ischemic postconditioning (PostC), by activation of the reperfusion injury salvage kinase (RISK) pathway. The N- and C-termini of the MG53 molecule can bind to Caveolin-3 and p85-PI3K kinases respectively to form a complex, which activates the RISK pathway to elicit cardiac protection (see Chun-Mei Cao et al., *Circulation* 121, 2565-2574, (2010)).

Although MG53 has cell membrane repair function and cardioprotective function, previous studies also found that MG53 has E3 ubiquitin ligase activity, which contributes to the development of insulin resistance and metabolic syndrome. The Ring domain of the TRIM motif at the N-terminus of MG53 binds to insulin receptor (IR) and insulin receptor substrate-1 (IRS1) and mediates the ubiquitination and subsequent degradation of these proteins by the proteasome, thereby blocking the insulin signaling pathway and leading to insulin resistance and associated metabolic diseases such as obesity, diabetes, hypertension, dyslipidemia, etc. (see, for example, R. Song et al. *Nature* 494, 375-379, (2013); J. S. Yi et al., *Nature Communications* 4, 2354 (2013)). Thus, the wild-type MG53 elicits cell membrane repair function and cardioprotective function, but also causes deleterious side effects, such as insulin resistance and its associated metabolic diseases.

SUMMARY OF THE INVENTION

The present invention relates to MG53 mutants, pharmaceutical compositions comprising the MG53 mutants, nucleic acids encoding the MG53 mutants, methods for preparing the MG53 mutants, and uses of the MG53 mutants in the manufacture of medicaments for treating heart diseases, diabetic cerebrovascular diseases, diabetic ocular complications, diabetic neuropathy, diabetic foot, kidney diseases, and diseases associated with cellular and/or tissue damage. In particular, the MG53 mutants may avoid or reduce metabolic side effects, such as insulin resistance, obesity, diabetes, hypertension, dyslipidemia, etc., while still retaining cell membrane repair function and/or cardioprotective function.

In one aspect, the present invention relates to an MG53 mutant, wherein the MG53 mutant is identical to the amino acid sequence of a wild-type MG53 except for at least one serine in the coiled-coil-SPRY region of the wild-type MG53, which is deleted and/or mutated into any other non-serine or non-threonine amino acid(s). In certain embodiments, the coiled-coil-SPRY region is located at positions 122-477 of the amino acid sequence of the wild-type MG53. In certain embodiments, the wild-type MG53 is derived from an animal, preferably from a mammal, e.g., human, mouse, rat, monkey, swine, dog, etc. In certain embodiments, the amino acid sequence of the wild type MG53 is set forth in SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142.

In certain embodiments, the MG53 mutant is identical to the amino acid sequence of a wild-type MG53 except for at least one serine in the coiled-coil-SPRY region of the wild-type MG53, which is mutated into a non-polar amino acid. In certain embodiments, the non-polar amino acid is selected from the group consisting of glycine, alanine, leucine, isoleucine, valine, proline, phenylalanine, methionine, and tryptophan. Preferably, in certain embodiments, the non-polar amino acid is alanine. In certain embodiments, the MG53 mutant is identical to the amino acid sequence of a wild-type MG53 except for at least one serine in the coiled-coil-SPRY region of the wild-type MG53, which is mutated into any non-serine or non-threonine polar amino acid(s). In certain embodiments, the polar amino acid is selected from the group consisting of glutamine, cysteine, asparagine, tyrosine, aspartic acid, glutamic acid, lysine, arginine, and histidine. Preferably, in certain embodiments, the polar amino acid is cysteine.

In certain embodiments, the deleted or mutated serine is located at one or more of positions 150, 189, 211, 214, 246, 255, 269, 296, 297, 301, 305, 306, 307, 314, 341, 377, 405, 418, 425, or 430 of the amino acid sequence set forth in SEQ ID NO: 1 of a wild-type MG53.

In certain embodiments, the deleted or mutated serine is located at one or more of positions 150, 189, 211, 214, 246, 255, 269, 296, 297, 301, 305, 306, 307, 314, 341, 377, 405, 418, 425, or 430 of the amino acid sequence set forth in SEQ ID NO: 139 of a wild-type MG53.

In certain embodiments, the deleted or mutated serine is located at one or more of positions 150, 189, 211, 214, 246, 255, 269, 296, 297, 301, 305, 306, 307, 314, 341, 377, 405, 418, 425, or 430 of the amino acid sequence set forth in SEQ ID NO: 140 of a wild-type MG53.

In certain embodiments, the deleted or mutated serine is located at one or more of positions 150, 189, 211, 214, 246, 255, 269, 296, 297, 301, 305, 306, 307, 314, 341, 377, 405, 418, 425, or 430 of the amino acid sequence set forth in SEQ ID NO: 141 of a wild-type MG53.

In certain embodiments, the deleted or mutated serine is located at one or more of positions 150, 189, 211, 214, 246, 255, or 269 of the amino acid sequence set forth in SEQ ID NO: 142 of a wild-type MG53.

In certain embodiments, the deleted or mutated serine is located at one or more of positions 188, 189, 210, 211, 214, 246, 253, 255, 269, 296, 297, 301, 305, 306, 307, 314, 341, 367, 377, 418, 430, or 440 of the amino acid sequence set forth in SEQ ID NO: 2 of a wild-type MG53.

In certain embodiments, the deleted or mutated serine is located at one or more of positions 150, 188, 189, 210, 211, 214, 246, 253, 255, 269, 296, 297, 301, 305, 307, 314, 341, 367, 377, 418, 430, 440, 464, or 474 of the amino acid sequence set forth in SEQ ID NO: 3 of a wild-type MG53.

In certain embodiments, the deleted or mutated serine is located at one or more of positions 150, 189, 211, 214, 246, 255, 269, 296, 297, 301, 305, 306, 307, 341, 377, 405, 418, 425, 430, or 464 of the amino acid sequence set forth in SEQ ID NO: 4 of a wild-type MG53.

In certain embodiments, the deleted or mutated serine is located at one or more of positions 150, 189, 211, 214, 246, 255, 269, 296, 301, 305, 307, 314, 341, 377, 411, 418, 425, 430, or 474 of the amino acid sequence set forth in SEQ ID NO: 5 of a wild-type MG53.

In certain embodiments, the deleted or mutated serine is located at one or more of positions 150, 189, 211, 214, 246, 255, 269, 296, 297, 301, 305, 307, 314, 341, 367, 377, 418, 425, or 430 of the amino acid sequence set forth in SEQ ID NO: 6 of a wild-type MG53.

In certain embodiments, the deleted or mutated serine is located at one or more of positions 150, 188-189, 210-211, 214, 246, 253-255, 269, 296-297, 301, 305-307, 314, 341, 367, 377, 405, 411, 418, 425, 430, 440, 464, or 474 of the amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142) of a wild-type MG53.

In certain embodiments, the deleted or mutated serine is located at one or more of positions 189, 211, 214, 246, 253-255, 269, 296, 301, 305, 307, 341, 377, 418, or 430 of the amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142) of a wild-type MG53.

In certain embodiments, the deleted or mutated serine is located at one or more of positions 211, 214, 246, 253-255, 269, 296, or 297 of the amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142) of a wild-type MG53.

In certain embodiments, the deleted or mutated serine is located at one or more of positions 211, 214, 246, 255, 269, 296, or 297 of the amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142) of a wild-type MG53.

In certain embodiments, the deleted or mutated serine is located at one or more of positions 253-255 of the amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142) of a wild-type MG53. In certain embodiments, the deleted or mutated serine is located at position 253 of the amino acid sequence of a wild-type MG53. In certain embodiments, the deleted or mutated serine is located at position 255 of the amino acid sequence of a wild-type MG53. In certain embodiments, the deleted or mutated serine is located at position 255 of the amino acid sequence set forth in SEQ ID NO: 1 of a wild-type MG53. In certain embodiments, the deleted or mutated serine is located at position 255 of the amino acid sequence set forth in SEQ ID NO: 139, SEQ ID NO: 140, SEQ ID NO: 141 or SEQ ID NO: 142 of a wild-type MG53.

In certain embodiments, the MG53 mutant comprises two or more serine mutations. In certain embodiments, two or more serine mutations of the MG53 mutant comprise serine mutation at one or more of positions 253-255. In certain embodiments, two or more serine mutations of the MG53 mutant comprise serine mutation at position 253. In certain embodiments, two or more serine mutations of the MG53 mutant comprise serine mutation at position 255. In certain embodiments, two or more serine mutations of the MG53 mutant comprise serine mutations at positions 253 and 255.

A person skilled in the art will comprehend that serine residues in the wild-type MG53 proteins of different species may be located at different positions, and thus the positions of the deleted or mutated serine may also differ. In certain embodiments, the deleted or mutated serine is within 1 to 10 amino acids, 1 to 5 amino acids, or 1 to 3 amino acids upstream or downstream of the corresponding serine position in the amino acid sequence of the wild-type MG53 set forth in SEQ ID NO: 1.

In certain embodiments, the amino acid sequence of the MG53 mutant is the amino acid sequence set forth in SEQ ID NO: 7, SEQ ID NO: 8, SEQ ID NO: 9, SEQ ID NO: 10, SEQ ID NO: 11, SEQ ID NO: 12, SEQ ID NO: 147, SEQ ID NO: 148, SEQ ID NO: 149 or SEQ ID NO: 150. Preferably, in certain embodiments, the amino acid sequence of the MG53 mutant is the amino acid sequence set forth in SEQ ID NO: 7. In certain embodiments, the amino acid sequence of the MG53 mutant has at least 70%, at least 75%, at least 80%, at least 85%, at least 90%, at least 95%, at least 98%, or at least 99% amino acid sequence homology to one of the amino acid sequences set forth in SEQ ID NO: 7, SEQ ID NO: 8, SEQ ID NO: 9, SEQ ID NO: 10, SEQ ID NO:11, SEQ ID NO: 12, SEQ ID NO: 147, SEQ ID NO: 148, SEQ ID NO: 149, SEQ ID NO:150, and the MG53 mutant avoids metabolic side effects caused by wild-type MG53 while still retaining cell membrane repair function and/or cardioprotective function.

In another aspect, the present invention relates to a pharmaceutical composition comprising the MG53 mutant and a pharmaceutically acceptable carrier.

In another aspect, the present invention relates to an isolated nucleic acid comprising a nucleic acid sequence encoding the amino acid sequence of the MG53 mutant. In certain embodiments, the nucleic acid comprises any one of the nucleic acid sequences set forth in SEQ ID NOs: 13-18. In certain embodiments, the nucleic acid comprises any one of the nucleic acid sequences set forth in SEQ ID NOS: 151-154.

In another aspect, the present invention relates to an expression vector comprising a nucleic acid sequence encoding the amino acid sequence of the MG53 mutant. In certain embodiments, the nucleic acid comprises any one of the nucleic acid sequences set forth in SEQ ID NOs: 13-18.

In certain embodiments, the nucleic acid comprises any one of the nucleic acid sequences set forth in SEQ ID NOs: 151-154.

In yet another aspect, the present invention relates to a host cell comprising the expression vector described herein.

In still another aspect, the present invention relates to a method for preparing the MG53 mutant, comprising determining one or more serine positions for mutation, performing site-directed mutagenesis at said position on the full-length sequence of a plasmid comprising a nucleic acid sequence encoding the amino acid sequence of a wild-type MG53, transfecting the plasmid with site-directed mutagenesis into a host cell, and inducing the host cell to produce the MG53 mutant. In certain embodiments, the site-directed mutagenesis comprises the following steps: (1) determining the corresponding nucleotide site of the amino acid targeted for site-directed mutagenesis in the cDNA sequence; modifying the nucleotide sequence at the mutation site according to the target amino acid; and designing primers by intercepting a sequence of 20-40 bp in length comprising the mutation site; (2) performing PCR reaction by using the primers of step (1) and taking a wild type MG53 plasmid as a template, performing agarose gel electrophoresis for the PCR product, and purifying the PCR product; (3) performing enzymatic reaction for the purified PCR product of step (2) by using restriction endonuclease, ligating the enzyme-digested product with a suitable plasmid expression vector, transforming and cultivating the ligation product in bacterial competent cells. In certain embodiments, the site-directed mutagenesis further comprises the following step: (4) selecting the clones of step (3) to perform colony PCR identification by using the primers of step (1), performing agarose gel electrophoresis for the PCR product, and then performing DNA sequencing identification to identify positive clones with the site-directed mutagenesis.

In another aspect, the present invention relates to use of the MG53 mutant in the manufacture of a medicament for treating heart diseases, diabetic cerebrovascular diseases, diabetic ocular complications, diabetic neuropathy, diabetic foot, kidney diseases, and diseases associated with cellular and/or tissue damage. In certain embodiments, the medicament may avoid or reduce metabolic side effects, such as insulin resistance, obesity, diabetes, hypertension, dyslipidemia, while treating heart diseases, diabetic cerebrovascular diseases, diabetic ocular complications, diabetic neuropathy, diabetic foot, kidney diseases, and diseases associated with cellular and/or tissue damage. In certain embodiments, the heart diseases are diseases associated with myocardial damage, including but not limited to, diabetic heart disease, myocardial ischemia, cardiac ischemia/reperfusion injury, myocardial infarction, heart failure, arrhythmia, heart rupture, angina, myocarditis, coronary heart disease, and pericarditis. In certain embodiments, the diabetic cerebrovascular diseases include, but are not limited to, cerebral arteriosclerosis, ischemic cerebrovascular disease, cerebral hemorrhage, cerebral atrophy, and cerebral infarction. In certain embodiments, the diabetic ocular complications include, but are not limited to, diabetic retinopathy, diabetic cataract, diabetic associated uveitis, and blindness. In certain embodiments, the diabetic neuropathy includes, but is not limited to, diabetic peripheral neuropathy. In certain embodiments, the kidney diseases include, but are not limited to, acute glomerulonephritis, chronic glomerulonephritis, nephrotic syndrome, acute kidney injury, diabetic nephropathy, etc. In certain embodiments, the diseases associated with cellular and/or tissue damage include, but are not limited to, diseases associated with the cellular and/or tissue damage of kidney, brain, lung, liver, heart, spleen, digestive tract, and skin, such as brain injury, lung injury, spleen injury, splenic rupture, gastric ulcer, gastritis, gastric perforation, gastrointestinal mucosal injury, trauma, burns, ulcers, mucositis, asthma, chronic obstructive pulmonary disease (COPD), stroke, skin aging, etc. In certain embodiments, the present invention relates to use of a polypeptide set forth in SEQ ID NO: 7 in the manufacture of a medicament for treating heart diseases, diabetic cerebrovascular diseases, diabetic ocular complications, diabetic neuropathy, diabetic foot, kidney diseases, and diseases associated with cellular and/or tissue damage. In certain embodiments, the present invention relates to use of a polypeptide set forth in SEQ ID NO: 147, SEQ ID NO: 148, SEQ ID NO: 149 or SEQ ID NO: 150 in the manufacture of a medicament for treating heart diseases, diabetic cerebrovascular diseases, diabetic ocular complications, diabetic neuropathy, diabetic foot, kidney diseases, and diseases associated with cellular and/or tissue damage.

In yet another aspect, the present invention relates to a method of treating heart diseases, diabetic cerebrovascular diseases, diabetic ocular complications, diabetic neuropathy, diabetic foot, kidney diseases, and diseases associated with cellular and/or tissue damage, comprising administering to a subject in need thereof a therapeutically effective amount of the MG53 mutant. In certain embodiments, the MG53 mutant may avoid or reduce metabolic side effects, such as insulin resistance, obesity, diabetes, hypertension, and dyslipidemia, while treating heart diseases, diabetic cerebrovascular diseases, diabetic ocular complications, diabetic neuropathy, diabetic foot, kidney diseases, and diseases associated with cellular and/or tissue damage. In certain embodiments, the heart diseases are diseases associated with myocardial damage, including but not limited to, diabetic heart disease, myocardial ischemia, cardiac ischemia/reperfusion injury, myocardial infarction, heart failure, arrhythmia, heart rupture, angina, myocarditis, coronary heart disease, and pericarditis. In certain embodiments, the diabetic cerebrovascular diseases include, but are not limited to, cerebral arteriosclerosis, ischemic cerebrovascular disease, cerebral hemorrhage, cerebral atrophy, and cerebral infarction. In certain embodiments, the diabetic ocular complications include, but are not limited to, diabetic retinopathy, diabetic cataract, diabetic associated uveitis, and blindness. In certain embodiments, the diabetic neuropathy includes, but is not limited to, diabetic peripheral neuropathy. In certain embodiments, the kidney diseases include, but are not limited to, acute glomerulonephritis, chronic glomerulonephritis, nephrotic syndrome, acute kidney injury, diabetic nephropathy, etc. In certain embodiments, the diseases associated with cellular and/or tissue damage include, but are not limited to, diseases associated with the cellular and/or tissue damage of kidney, brain, lung, liver, heart, spleen, digestive tract, and skin, such as brain injury, lung injury, spleen injury, splenic rupture, gastric ulcer, gastritis, gastric perforation, gastrointestinal mucosal injury, trauma, burns, ulcers, mucositis, asthma, chronic obstructive pulmonary disease (COPD), stroke, skin aging, etc. In certain embodiments, the present invention relates to a method of treating heart diseases, diabetic cerebrovascular diseases, diabetic ocular complications, diabetic neuropathy, diabetic foot, kidney diseases, and diseases associated with cellular and/or tissue damage, comprising administering to a subject in need thereof a therapeutically effective amount of the polypeptide set forth in SEQ ID NO: 7. In certain embodiments, the present invention relates to a method of treating heart diseases, diabetic cerebrovascular diseases, diabetic ocular complications, diabetic neuropathy, diabetic foot, kidney diseases, and diseases associated with cellular and/or tissue damage, comprising administering to a subject in need thereof a therapeutically effective amount of a polypeptide set forth in SEQ ID NO: 147, SEQ ID NO: 148, SEQ ID NO: 149, or SEQ ID NO: 150.

In yet other aspect, the present invention relates to an MG53 mutant for use in treating heart diseases, diabetic cerebrovascular diseases, diabetic ocular complications, diabetic neuropathy, diabetic foot, kidney diseases, and diseases associated with cellular and/or tissue damage. In certain embodiments, the MG53 mutant may avoid or reduce metabolic side effects, such as insulin resistance, obesity, diabetes, hypertension, and dyslipidemia, while treating heart diseases, diabetic cerebrovascular diseases, diabetic ocular complications, diabetic neuropathy, diabetic foot, kidney diseases, and diseases associated with cellular and/or tissue damage. In certain embodiments, the heart diseases are diseases associated with myocardial damage, including but not limited to, diabetic heart disease, myocardial ischemia, cardiac ischemia/reperfusion injury, myocardial infarction, heart failure, arrhythmia, heart rupture, angina, myocarditis, coronary heart disease, and pericarditis. In certain embodiments, the diabetic cerebrovascular diseases include, but are not limited to, cerebral arteriosclerosis, ischemic cerebrovascular disease, cerebral hemorrhage, cerebral atrophy, and cerebral infarction. In certain embodiments, the diabetic ocular complications include, but are not limited to, diabetic retinopathy, diabetic cataract, diabetic associated uveitis, and blindness. In certain embodiments, the diabetic neuropathy includes, but is not limited to, diabetic peripheral neuropathy. In certain embodiments, the kidney diseases include, but are not limited to, acute glomerulonephritis, chronic glomerulonephritis, nephrotic syndrome, acute kidney injury, diabetic nephropathy, etc. In certain embodiments, the diseases associated with cellular and/or tissue damage include, but are not limited to, diseases associated with the cellular and/or tissue damage of kidney, brain, lung, liver, heart, spleen, digestive tract, and skin, such as brain injury, lung injury, spleen injury, splenic rupture, gastric ulcer, gastritis, gastric perforation, gastrointestinal mucosal injury, trauma, burns, ulcers, mucositis, asthma, chronic obstructive pulmonary disease (COPD), stroke, skin aging, etc. In certain embodiments, the present invention relates to a polypeptide set forth in SEQ ID NO: 7 for use in treating heart diseases, diabetic cerebrovascular diseases, diabetic ocular complications, diabetic neuropathy, diabetic foot, kidney diseases, and diseases associated with cellular and/or tissue damage. In certain embodiments, the present invention relates to a polypeptide set forth in SEQ ID NO: 147, SEQ ID NO: 148, SEQ ID NO: 149, or SEQ ID NO: 150 for use in treating heart diseases, diabetic cerebrovascular diseases, diabetic ocular complications, diabetic neuropathy, diabetic foot, kidney diseases, and diseases associated with cellular and/or tissue damage.

BRIEF DESCRIPTION OF THE FIGURES

FIG. 2 illustrates the amino acid sequence SEQ ID NO: 1 of human wild-type MG53 and its encoding nucleic acid sequence SEQ ID NO: 19.

FIG. 3 illustrates the amino acid sequence SEQ ID NO: 2 of mouse wild-type MG53 and its encoding nucleic acid sequence SEQ ID NO: 20.

FIG. 4 illustrates the amino acid sequence SEQ ID NO: 3 of rat wild-type MG53 and its encoding nucleic acid sequence SEQ ID NO: 21.

FIG. 5 illustrates the amino acid sequence SEQ ID NO: 4 of monkey wild-type MG53 and its encoding nucleic acid sequence SEQ ID NO: 22.

FIG. 6 illustrates the amino acid sequence SEQ ID NO: 5 of swine wild-type MG53 and its encoding nucleic acid sequence SEQ ID NO: 23.

FIG. 7 illustrates the amino acid sequence SEQ ID NO: 6 of dog wild-type MG53 and its encoding nucleic acid sequence SEQ ID NO: 24.

FIG. 8 illustrates the amino acid sequence SEQ ID NO: 7 of human MG53 S255A mutant and its encoding nucleic acid sequence SEQ ID NO: 13.

FIG. 9 illustrates the amino acid sequence SEQ ID NO: 8 of mouse MG53 S255A mutant and its encoding nucleic acid sequence SEQ ID NO: 14.

FIG. 10 illustrates the amino acid sequence SEQ ID NO: 9 of rat MG53 S255A mutant and its encoding nucleic acid sequence SEQ ID NO: 15.

FIG. 11 illustrates the amino acid sequence SEQ ID NO: 10 of monkey MG53 S255A mutant and its encoding nucleic acid sequence SEQ ID NO: 16.

FIG. 12 illustrates the amino acid sequence SEQ ID NO: 11 of swine MG53 S255A mutant and its encoding nucleic acid sequence SEQ ID NO: 17.

FIG. 13 illustrates the amino acid sequence SEQ ID NO: 12 of dog MG53 S255A mutant and its encoding nucleic acid sequence SEQ ID NO: 18.

FIG. 16 illustrates that mouse MG53 S255A mutation inhibits MG53-mediated substrate degradation. The upper panel of FIG. 16A shows IRS1 protein content detected by Western Blot in plasmids overexpressing IRS1, mouse wild-type MG53, mouse MG53 S255A mutant, or mouse MG53-D-RING truncated mutant in HEK293T cell line, wherein CON represents an empty vector plasmid control without expression of mouse wild-type MG53, mouse MG53 S255A mutant, and mouse MG53-D-RING truncated mutant; MG53 represents a vector plasmid expressing mouse wild-type MG53; S255A represents a vector plasmid expressing mouse MG53 S255A mutant; D-RING represents a vector plasmid expressing mouse MG53 truncated mutant MG53-D-RING, in which mouse RING domain is truncated. The lower panel of FIG. 16A is a statistic diagram of the upper panel (n=5, *p<0.05; p<0.01). The upper panel of FIG. 16B shows IR protein content detected by Western Blot in plasmids overexpressing IR, mouse wild-type MG53, mouse MG53 S255A mutant, or mouse MG53-D-RING truncated mutant in HEK293T cell line, wherein CON represents an empty vector plasmid control without expression of mouse wild-type MG53, mouse MG53 S255A mutant, and mouse MG53-D-RING truncated mutant; MG53 represents a vector plasmid expressing mouse wild-type MG53; S255A represents a vector plasmid expressing mouse MG53 S255A mutant; D-RING represents a vector plasmid expressing mouse MG53-D-RING truncated mutant. The lower panel of FIG. 16B is a statistic diagram of the upper panel (n=5, p<0.01).

FIG. 18A shows the content of MG53-IRS1 complex detected by immunoprecipitating IRS1 protein and performing Western Blot after co-expressing mouse wild-type MG53 and MG53 substrate IRS1, or co-expressing mouse MG53 S255A mutant and MG53 substrate IRS1 in HEK293T cell line. In FIG. 18A, MG53 represents mouse wild-type MG53, MG53 S255A represents mouse MG53 S255A mutant, IRS1 represents mouse insulin receptor substrate. FIG. 18B shows the binding intensity of immobilized and purified protein IRS1 to purified protein mouse wild-type MG53 or mouse MG53 S255A mutant in the mobile phase during surface plasmon resonance (SPR) test, wherein MG53 represents mouse wild-type MG53, MG53-S255A represents mouse MG53 S255A mutant, and Rat IRS1 represents rat insulin receptor substrate.

FIG. 20 illustrates the amino acid sequence SEQ ID NO: 139 (which corresponds to NCBI number BAD18630.1) of a human MG53 subtype and its encoding nucleic acid sequence SEQ ID NO: 143.

FIG. 21 illustrates the amino acid sequence SEQ ID NO: 140 (which corresponds to NCBI Accession No. XP_016878743.1) of a human MG53 subtype and its encoding nucleic acid sequence in SEQ ID NO: 144.

FIG. 22 illustrates the amino acid sequence SEQ ID NO: 141 (which corresponds to NCBI BAC03506.1) of a human MG53 subtype and its encoding nucleic acid sequence SEQ ID NO: 145.

FIG. 23 illustrates the amino acid sequence SEQ ID NO: 142 (which corresponds to NCBI number AAH33211.1) of a human MG53 subtype and its encoding nucleic acid sequence SEQ ID NO: 146.

FIG. 24 illustrates the amino acid sequence SEQ ID NO: 147 of a human MG53 subtype S255A mutant and its encoding nucleic acid sequence SEQ ID NO: 151.

FIG. 25 illustrates the amino acid sequence SEQ ID NO: 148 of a human MG53 subtype S255A mutant and its encoding nucleic acid sequence SEQ ID NO: 152.

FIG. 26 illustrates the amino acid sequence SEQ ID NO: 149 of a human MG53 subtype S255A mutant and its encoding nucleic acid sequence SEQ ID NO: 153.

FIG. 27 illustrates the amino acid sequence SEQ ID NO: 150 of a human MG53 subtype S255A mutant and its encoding nucleic acid sequence in SEQ ID NO: 154.

FIG. 28 illustrates the nomenclature schematic of the amino acid positions of full-length MG53 proteins and fragments thereof for each species in the present invention.

DETAILED DESCRIPTION

Although various aspects and embodiments of the present invention will be disclosed in the following, a person skilled in the art can make various equivalent changes and modifications without departing from the spirit and scope of the subject matter of the application. The various aspects and embodiments disclosed herein are given by way of illustration only, and are not intended to limit the present invention. The actual protection scope of the present application is defined by the claims. Unless defined otherwise, all technical and scientific terms used herein have the same meaning as commonly understood by a person having ordinary skills in the art to which this invention pertains. All references, patents, patent applications cited in the present application are hereby incorporated by reference in their entireties.

In one aspect, the present invention relates to an MG53 mutant, wherein the MG53 mutant is identical to the amino acid sequence of a wild-type MG53 except for at least one serine in the coiled-coil-SPRY region of the wild-type MG53, which is deleted and/or mutated into any other non-serine or non-threonine amino acid(s).

Figure 1:
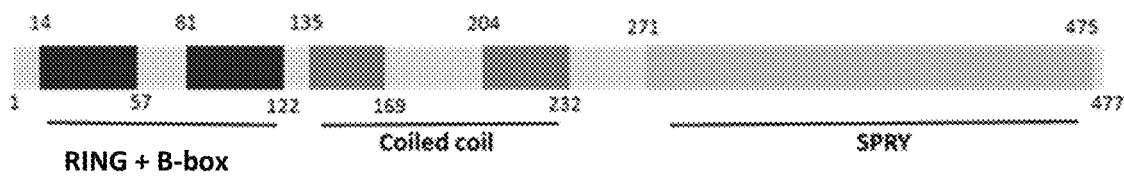
FIG. 1 illustrates the molecular structure of a wild-type MG53.

As used herein, the term "wild-type MG53" or "wild-type MG53 protein" refers to the natural sequence of a full-length MG53 protein or fragments thereof expressed in a subject. MG53 protein is a multi-functional protein with a structure shown in FIG. 1. The full-length MG53 proteins of different species are slightly different in length, but generally have about 477 amino acids, comprising a TRIM motif at the N-terminus and a SPRY motif at the C-terminus. The TRIM motif consists of successively linked Ring, B-box and coiled-coil domains (RBCC). MG53 protein is one of the important components for membrane repair, which plays an essential role in the pre-conditioning and post-conditioning protection of ischemia-reperfusion injury. Meanwhile, the high expression of MG53 protein may also cause insulin resistance and metabolic syndrome. The structure and function of MG53, as well as its interaction with other proteins have been reported in detail in the art (see, e.g., Chuanxi Cai et al., *Journal of Biological Chemistry*, 284 (5), 3314-3322, (2009); Xianhua Wang et al., *Circulation Research* 107, 76-83, (2010); Eun Young Park et al., *Proteins*, 790-795 (2009)).

As used herein, the term "subject" includes both human and non-human animals. Non-human animals include all vertebrates, such as mammals and non-mammals. The "subject" may also be a domestic animal such as cow, swine, sheep, poultry and horse; or rodent such as rat, mouse; or a primate such as ape, monkey; or domesticated animal such as dog or cat. "Subject" may be male or female, and may be elderly, adult, adolescent, child or infant. A human "subject" may be Caucasian, African, Asian, Semitic, or other races, or a mixture of the racial backgrounds above.

In certain embodiments, the wild-type MG53 is preferably derived from a mammal, e.g., human, ape, monkey, mouse, rat, swine, dog, etc. A person skilled in the art may, from an open channel (e.g., National Center for Biotechnology Information (NCBI)), obtain the amino acid sequence of wild-type MG53 of each species, which is incorporated herein by reference. In certain embodiments, the amino acid sequence of the wild-type MG53 is set forth in SEQ ID NO: 1, SEQ ID NO: 2, SEQ ID NO: 3, SEQ ID NO: 4, SEQ ID NO: 5 or SEQ ID NO: 6, which corresponds to the human, mouse, rat, monkey, swine, and dog wild-type MG53 full length protein, respectively.

As used herein, the terms "protein", "polypeptide" and "peptide" are used interchangeably to refer to a polymer of amino acids. The proteins, polypeptides or peptides described herein may contain natural amino acids, non-natural amino acids, or analogs or mimetics of amino acids. The proteins, polypeptides or peptides described herein may be obtained by any known method in the art, such as, but not limited to, by natural isolation, recombinant expression, chemical synthesis, etc.

As used herein, the term "coiled-coil-SPRY region" is a corresponding region of the amino acid sequence of a wild-type MG53. The coiled-coil domain, existing in most TRIM family proteins, mediates homologous or heterologous association between TRIM family members or between TRIM members and other proteins to form complexes such as dimers, polymers, etc., thereby eliciting cell membrane repair (see, e.g., Ozato et al., *Nature Review Immunology*, 8: 849-860 (2008); Sanchez S. et al., *PNAS*, 111: 2494-2499 (2014)). The SPRY domain is located at the C-terminus of the amino acid sequence of a wild-type MG53 and is typically located at positions 288-477 of the amino acid sequence of a wild-type MG53. In certain embodiments, the SPRY domain described herein includes a PRY motif and a SPRY motif. The SPRY domain is evolutionarily conserved and is expressed throughout fungi to higher animals (see, e.g., Ozato et al., *Nature Review Immunology*, 8: 849-860 (2008)). So far, about 60 TRIM family members are identified in different mammalian genomes, among which 15 members carry a similar SPRY domain after the TRIM domain (i.e., the Ring-B-box-Coiled-Coil domain), and MG53 exhibits a conserved primary structure with these TRIM subfamily proteins (see, e.g., WO2009/073808). The specific amino acid positions corresponding to the coiled-coil-SPRY region may be slightly different among different species, but a person skilled in the art may obtain the specific amino acid positions corresponding to the coiled-coil-SPRY region of wild-type MG53 of different species through the prior art (e.g., the information as disclosed in NCBI) and/or routine experimental methods. In certain embodiments, the coiled-coil-SPRY region as used herein refers to amino acid positions 122-477 of a wild-type MG53 or a structurally similar region. In certain embodiments, the structurally similar region may be a region comprising 70%, 80% or 90% contiguous amino acid sequence of amino acid positions 122-477. In certain embodiments, the N-terminal initiation site of the structurally similar region may have about 1, 2, 3, 4, 5, 6, 7, 8, 9, 10, 15 or 20 amino acids longer or shorter than the N-terminus of the amino acid positions 122-477, and/or the C-terminal termination site of the structurally similar region may have about 1, 2, 3, 4, 5, 6, 7, 8, 9, 10, 15 or 20 amino acids longer or shorter than the C-terminus of the amino acid positions 122-477. For example, in certain embodiments, the coiled-coil-SPRY region as used herein refers to the coiled-coil-SPRY region of human wild-type MG53 (i.e., SEQ ID NO: 1), which corresponds to amino acid positions 122-477 of SEQ ID NO: 1.

As used herein, the term "MG53 mutant" or "MG53 protein mutant" refers to an MG53 protein variant or fragment in which the natural amino acid sequence of a wild-type MG53 protein is modified. Such modifications include, but are not limited to, deletion and/or substitution of one or more amino acids. In certain embodiments, the MG53 mutant of the present invention is identical to the amino acid sequence of a wild-type MG53 except for at least one serine in the coiled-coil-SPRY region of the wild-type MG53, which is deleted and/or mutated into any other non-serine or non-threonine amino acid(s).

As used herein, "at least one serine" refers to one or more serine, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more serine within the coiled-coil-SPRY region of a wild-type MG53.

As used herein, "other non-serine or non-threonine amino acids" refers to any other natural amino acids, substituted natural amino acids, non-natural amino acids, substituted non-natural amino acids, or any combination thereof, that are not serine or threonine. The names of natural amino acids are represented as standard single letter or three-letter codes in the present application. Natural amino acids include non-polar amino acids and polar amino acids. Unless otherwise specified, any of the amino acids described herein may be in the D- or L-configuration.

In certain embodiments, at least one serine (Ser or S) within the coiled-coil-SPRY region of the wild-type MG53 is deleted or mutated into a non-polar amino acid. The non-polar amino acids include glycine (Gly or G), alanine (Ala or A), leucine (Leu or L), isoleucine (Ile or I), valine (Val or V), proline (Pro or P), phenylalanine (Phe or F), methionine (Met or M), tryptophan (Trp or W). In certain embodiments, at least one serine within the coiled-coil-SPRY region of the wild-type MG53 is deleted or mutated into glycine or alanine. Preferably, in certain embodiments, at least one serine within the coiled-coil-SPRY region of the wild-type MG53 is deleted or mutated into alanine. More preferably, in certain embodiments, at least one serine within the coiled-coil-SPRY region of the wild-type MG53 is mutated into alanine.

In certain embodiments, at least one serine within the coiled-coil-SPRY region of the wild-type MG53 is deleted or mutated into a polar amino acid. The polar amino acids include glutamine (Gln or Q), cysteine (Cys or C), asparagine (Asn or N), tyrosine (Tyr or Y), aspartic acid (Asp or D), glutamic acid (Glu or E), lysine (Lys or K), arginine (Arg or R), histidine (His or H). In certain embodiments, at least one serine within the coiled-coil-SPRY region of the wild-type MG53 is deleted or mutated into cysteine or histidine. Preferably, in certain embodiments, at least one serine within the coiled-coil-SPRY region of the wild-type MG53 is deleted or mutated into cysteine. More preferably, in certain embodiments, at least one serine within the coiled-coil-SPRY region of the wild-type MG53 is mutated into cysteine.

In certain embodiments, the serine mutations described herein include one serine is substituted with one or more other non-serine or non-threonine amino acids, for example, one serine may be substituted with 1, 2, 3, 4, 5, 6, 7, 8, 9 or 10 other non-serine or non-threonine amino acids. If two or more serine are substituted, then each serine may be independently substituted with one or more other non-serine or non-threonine amino acids, respectively.

The specific serine positions of the wild-type MG53 of each species may vary from species to species; however, once the amino acid sequence of the wild-type MG53 of a species and the amino acid region corresponding to its coiled-coil-SPRY region is known, a person skilled in the art can determine the specific amino acid positions to which the serine within the coiled-coil-SPRY region corresponds. For example, a person skilled in the art knows that the amino acid sequence of human wild-type MG53 is set forth in SEQ ID NO: 1 and its coiled-coil-SPRY region corresponds to amino acid positions 122-477 of SEQ ID NO: 1. Under such circumstances, a person skilled in the art can determine that the specific amino acid positions corresponding to serine within the coiled-coil-SPRY region of human wild-type MG53 are positions 150, 189, 211, 214, 246, 255, 269, 296, 297, 301, 305, 306, 307, 314, 341, 377, 405, 418, 425, 430 of SEQ ID NO: 1, respectively.

In certain embodiments, the deleted or mutated serine is located at one or more of the following positions of human wild-type MG53 amino acid sequence set forth in SEQ ID NO: 1: positions 150, 189, 211, 214, 246, 255, 269, 296, 297, 301, 305, 306, 307, 314, 341, 377, 405, 418, 425, 430.

In certain embodiments, the MG53 protein as described herein includes a full-length MG53 protein, or a truncated mutant thereof (i.e., a truncated fragment of the full-length MG53 protein) or a mutant having mutation, addition or deletion of one or more amino acids compared to the full-length MG53 protein or the truncated mutant thereof. In this case, in order to unify the nomenclature of amino acid positions for the amino acid sequences of different MG53 protein subtypes, when the amino acid position of a certain MG53 protein subtype is mentioned in the present invention, the amino acid sequence of the MG53 protein subtype shall be aligned with the amino acid sequence of the full-length MG53 protein (e.g., SEQ ID NO: 1) and if necessary, gaps shall be introduced into the relevant amino acid sequence so as to maximize the number of identical amino acids. The position No. of the first amino acid in the amino acid sequence of the MG53 subtype is designated as the position No. of the full-length MG53 protein that corresponds to said amino acid, so that when reference is made to the amino acid positions of the wild-type MG53 of a species, both the full-length MG53 protein and the truncated mutant thereof refer to the position No. in the amino acid sequence of the full-length MG53 protein.

For example, as shown in FIG. 28, the full-length MG53 protein of a species has n amino acids and the corresponding amino acid positions are positions 1–n. The amino acid sequence of MG53 subtype 1, compared to the amino acid sequence of the full-length MG53 protein, contains a truncated mutant corresponding to the amino acids located at positions m–n of the full-length sequence. Thus, the first amino acid position of the MG53 subtype 1 amino acid sequence is designated as position m, and the second amino acid position of the MG53 subtype 1 amino acid sequence is designated as position m+1, analogously, the last amino acid position of the MG53 subtype 1 amino acid sequence is designated as position n. For another example, the amino acid sequence of MG53 subtype 2, compared to the amino acid sequence of the full-length MG53 protein, contains a truncated mutant corresponding to the amino acids located at positions 1–s of the full-length sequence. Thus, the first amino acid position of the MG53 subtype 2 amino acid sequence is designated as position 1, and the second amino acid position of the MG53 subtype 2 amino acid sequence is designated as position 2, analogously, the last amino acid position of the MG53 subtype 2 amino acid sequence is designated as position s. For yet another example, the amino acid sequence of MG53 subtype 3, compared to the amino acid sequence of the full-length MG53 protein, contains a truncated mutant corresponding to the amino acids located at positions p–q of the full-length sequence. Thus, the first amino acid position of the MG53 subtype 3 amino acid sequence is designated as position p, and the second amino acid position of the MG53 subtype 3 amino acid sequence is designated as position p+1, analogously, the last amino acid position of the MG 53 subtype 3 amino acid sequence is designated as position q.

For example, SEQ ID NO: 140 is one of the human wild-type MG53 subtypes, having 333 amino acids corresponding to amino acid positions 145-477 of the human wild-type MG53 full-length sequence set forth in SEQ ID NO: 1. Under this circumstance, the first amino acid (methionine) position of the amino acid sequence SEQ ID NO: 140 is designated as position 145 of SEQ ID NO: 140, and the second amino acid position is designated as position 146 of SEQ ID NO: 140, analogously, the last amino acid position of the amino acid sequence SEQ ID NO: 140 is designated as position 477 of SEQ ID NO: 140. As another example, SEQ ID NO: 141 is one of the human wild-type MG53 subtypes, which also has 333 amino acids, and only one amino acid differs from amino acid positions 145-477 of the human wild-type MG53 full-length sequence set forth in SEQ ID NO: 1, that is, position 315 of SEQ ID NO: 1 is glutamic acid, while the corresponding position of SEQ ID NO: 141 is glycine. Under this circumstance, the first amino acid position (methionine) of the amino acid sequence set forth in SEQ ID NO: 141 is designated as position 145 of SEQ ID NO: 141, and the second amino acid position is designated as position 146 of SEQ ID NO: 141, analogously, the last amino acid position is designated as position 477 of SEQ ID NO: 141. As yet another example, SEQ ID NO: 142 is one of the human wild-type MG53 subtypes, having 269 amino acids corresponding to amino acid positions 1-269 of the human wild-type MG53 full-length sequence set forth in SEQ ID NO: 1. Under this circumstance, the first amino acid (methionine) position of the amino acid sequence SEQ ID NO: 142 is designated as position 1 of SEQ ID NO: 142, the second amino acid position of the amino acid sequence SEQ ID NO: 142 is designated as position 2 of SEQ ID NO: 142, analogously, the last amino acid position of the amino acid sequence SEQ ID NO: 142 is designated as position 269 of SEQ ID NO: 142.

In certain embodiments, the deleted or mutated serine is located at one or more of the following positions of human wild-type MG53 subtype amino acid sequence set forth in SEQ ID NO: 139: positions 150, 189, 211, 214, 246, 255, 269, 296, 297, 301, 305, 306, 307, 314, 341, 377, 405, 418, 425, or 430.

In certain embodiments, the deleted or mutated serine is located at one or more of the following positions of human wild-type MG53 subtype amino acid sequence set forth in SEQ ID NO: 140: positions 150, 189, 211, 214, 246, 255, 269, 296, 297, 301, 305, 306, 307, 314, 341, 377, 405, 418, 425, or 430.

In certain embodiments, the deleted or mutated serine is located at one or more of the following positions of human wild-type MG53 subtype amino acid sequence set forth in SEQ ID NO: 141: positions 150, 189, 211, 214, 246, 255, 269, 296, 297, 301, 305, 306, 307, 314, 341, 377, 405, 418, 425, or 430.

In certain embodiments, the deleted or mutated serine is located at one or more of the following positions of human wild-type MG53 subtype amino acid sequence set forth in SEQ ID NO: 142: positions 150, 189, 211, 214, 246, 255, or 269.

In certain embodiments, the deleted or mutated serine is located at one or more of the following positions of mouse wild-type MG53 amino acid sequence set forth in SEQ ID NO: 2: positions 188, 189, 210, 211, 214, 246, 253, 255, 269, 296, 297, 301, 305, 306, 307, 314, 341, 367, 377, 418, 430, or 440.

In certain embodiments, the deleted or mutated serine is located at one or more of the following positions of rat wild-type MG53 amino acid sequence set forth in SEQ ID NO: 3: positions 150, 188, 189, 210, 211, 214, 246, 253, 255, 269, 296, 297, 301, 305, 307, 314, 341, 367, 377, 418, 430, 440, 464, or 474.

In certain embodiments, the deleted or mutated serine is located at one or more of the following positions of monkey wild-type MG53 amino acid sequence set forth in SEQ ID NO: 4: positions 150, 189, 211, 214, 246, 255, 269, 296, 297, 301, 305, 306, 307, 341, 377, 405, 418, 425, 430, or 464.

In certain embodiments, the deleted or mutated serine is located at one or more of the following positions of swine wild-type MG53 amino acid sequence set forth in SEQ ID NO: 5: positions 150, 189, 211, 214, 246, 255, 269, 296, 301, 305, 307, 314, 341, 377, 411, 418, 425, 430, or 474.

In certain embodiments, the deleted or mutated serine is located at one or more of the following positions of dog wild-type MG53 amino acid sequence set forth in SEQ ID NO: 6: positions 150, 189, 211, 214, 246, 255, 269, 296, 297, 301, 305, 307, 314, 341, 367, 377, 418, 425, or 430.

The specific positions of the deleted or mutated serine may vary from species to species, however, the serine position of wild-type MG53 protein is highly conserved among various species. For example, positions 189, 211, 214, 246, 255, 269, 296, 301, 305, 307, 341, 377, 418, and 430 of amino acid sequences of the human, mouse, rat, monkey, swine and dog wild-type MG53 proteins are all serine. In some embodiments, the deleted or mutated serine is located at one or more of the following positions of a wild-type MG53 amino acid sequence (e.g., SEQ ID NOs: 1-6): positions 189, 211, 214, 246, 255, 269, 296, 301, 305, 307, 341, 377, 418, or 430.

In certain embodiments, the deleted or mutated serine is located at one or more of the following positions of a wild-type MG53 amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142): positions 150, 188-189, 210-211, 214, 246, 253-255, 269, 296-297, 301, 305-307, 314, 341, 367, 377, 405, 411, 418, 425, 430, 440, 464, or 474.

In certain embodiments, the deleted or mutated serine is located at one or more of the following positions of a wild-type MG53 amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142): positions 189, 211, 214, 246, 253-255, 269, 296, 301, 305, 307, 341, 377, 418, or 430.

In certain embodiments, the deleted or mutated serine is located at one or more of the following positions of a wild-type MG53 amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142): positions 211, 214, 246, 253-255, 269, 296, or 297.

In certain embodiments, the deleted or mutated serine is located at one or more of the following positions of a wild-type MG53 amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142): positions 211, 214, 246, 255, 269, 296, or 297.

In certain embodiments, the deleted or mutated serine is located at one or more of positions 253-255 of a wild-type MG53 amino acid sequence (e.g., SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142). In certain embodiments, the deleted or mutated serine is located at position 253 of a wild-type MG53 amino acid sequence. In certain embodiments, the deleted or mutated serine is located at position 255 of a wild-type MG53 amino acid sequence. In certain embodiments, the deleted or mutated serine is located at position 255 of the wild-type MG53 amino acid sequence SEQ ID NO: 1. In certain embodiments, the deleted or mutated serine is located at position 255 of the wild-type MG53 amino acid sequence SEQ ID NO: 139, SEQ ID NO: 140, SEQ ID NO: 141, or SEQ ID NO: 142.

In certain embodiments, the MG53 mutant has two or more serine mutations. In certain embodiments, two or more serine mutations of the MG53 mutant include serine mutation at one or more of positions 253-255. In certain embodiments, two or more serine mutations of the MG53 mutant include serine mutation at position 253. In certain embodiments, two or more serine mutations of the MG53 mutant include serine mutation at position 255. In certain embodiments, two or more serine mutations of the MG53 mutant include serine mutation at positions 253 and 255.

A person skilled in the art will comprehend that serine residues among the wild-type MG53 proteins of different species may be located at different positions, and thus the positions of the deleted or mutated serine may also differ. In certain embodiments, the deleted or mutated serine is within 1 to 10 amino acids, 1 to 5 amino acids, or 1 to 3 amino acids upstream or downstream of the corresponding serine position in the amino acid sequence of the wild-type MG53 set forth in SEQ ID NO: 1.

In certain embodiments, the amino acid sequence of the MG53 mutant is the amino acid sequence set forth in SEQ ID NO: 7, SEQ ID NO: 8, SEQ ID NO: 9, SEQ ID NO: 10, SEQ ID NO: 11, SEQ ID NO: 12, SEQ ID NO: 147, SEQ ID NO: 148, SEQ ID NO: 149, or SEQ ID NO: 150. More preferably, in certain embodiments, the amino acid sequence of the MG53 mutant is the amino acid sequence set forth in SEQ ID NO: 7. In certain embodiments, the amino acid sequence of the MG53 mutant has at least 70%, at least 75%, at least 80%, at least 85%, at least 90%, at least 95%, at least 98%, or at least 99% amino acid sequence homology to one of the amino acid sequences set forth in SEQ ID NO: 7, SEQ ID NO: 8, SEQ ID NO: 9, SEQ ID NO: 10, SEQ ID NO:11, SEQ ID NO: 12, SEQ ID NO: 147, SEQ ID NO: 148, SEQ ID NO: 149, SEQ ID NO:150, and the MG53 mutant avoids metabolic side effects caused by wild-type MG53 while still retaining cell membrane repair function and/or cardioprotective function.

As used herein, the percent (%) "sequence homology to" refers to, for amino acid sequences, the percentage of identity between two amino acid sequences after aligning the candidate and the reference sequences, and if necessary introducing gaps, to achieve the maximum number of identical amino acids; for nucleotide sequence, the percentage of identity between two nucleotide sequences after aligning the candidate and the reference sequences, and if necessary introducing gaps, to achieve the maximum number of identical nucleotides.

The percentage of homology can be determined by various well-known methods in the art. For example, the comparison of sequences can be achieved by the following publically available tools: BLASTp software (available from the website of National Center for Biotechnology Information (NCBI): http://blast.ncbi.nlm.nih.gov/Blast.cgi, also see, Altschul S F et al., *J. Mol. Biol.,* 215: 403-410 (1990); Stephen F. et al., *Nucleic Acids Res.,* 25: 3389-3402 (1997)), ClustalW2 (available from the website of European Bioinformatics Institute: http://www.ebi.ack.uk/Tools/msa/clustalw2/, see Higgins D G et al., *Methods in Enzymology,* 266: 383-402 (1996); Larkin M A et al., *Bioinformatics* (Oxford, England), 23 (21): 2947-8 (2007)), and TCoffee (available from the Swiss Institute of Bioinformatics website, also see Poirot O. et al., *Nucleic Acids Res.,* 31 (13): 3503-6 (2003); Notredame C. et al., *J. Mol. Boil.,* 302 (1): 205-17 (2000)). If the alignment of the sequences is performed using software, the default parameters available in the software may be used, or otherwise the parameters may be customized to suit the alignment purpose. All of these are within the scope of knowledge of a person skilled in the art.

In certain embodiments, SEQ ID NOs: 7-12, SEQ ID NOs: 147-150 and the MG53 mutants that have amino acid sequence homology to SEQ ID NOs: 7-12 and SEQ ID NOs: 147-150 avoid metabolic side effects caused by wild-type MG53, while still retaining cell membrane repair function and/or cardioprotective function.

The inventors of the present invention have found that when at least one serine in the coiled-coil-SPRY region of a wild-type MG53 is deleted or mutated into any other non-serine or non-threonine amino acid(s), the metabolic side effects caused by the wild-type MG53 can be avoided or reduced, without any impact on the cell membrane repair function and/or cardioprotective function of MG53. While not wishing to be bound by any theory, the above results may be due to the fact that the phosphorylation of serine within the coiled-coil-SPRY region of a wild-type MG53 may significantly regulate the E3 ubiquitin ligase activity of MG53 and modulate the regulation function of MG53 on insulin signaling system through substrates IRβ and IRS1. However, the phosphorylation of serine within this region does not regulate the cell membrane repair function and/or cardioprotective function of MG53.

As used herein, "cell membrane repair function" refers to the ability of wild-type MG53 or MG53 mutants to repair and restore the damaged cell membrane during cell injury, especially acute cell injury, through activating relevant signaling pathways (e.g. the RISK pathway) to reduce cell death, promote cell survival, and thereby restore cellular functions. In certain embodiments, the wild-type MG53 or MG53 mutants of the present invention can repair viable cells, cells in vitro, or cells in vivo. The wild-type MG53 or MG53 mutants of the present invention can also repair different types of cells, such as, but not limited to, cardiomyocytes, striated muscle cells, skeletal muscle cells, renal proximal tubular epithelial cells, alveolar epithelial cells, gastrointestinal epithelial cells (e.g., oral epithelial cells, esophageal epithelial cells, gastric epithelial cells, duodenal epithelial cells, small intestinal epithelial cells, jejunal epithelial cells, ileum epithelial cells, colonic epithelial cells), mucosal cells (e.g., oral mucosal cells, nasal mucosal cells, gastric mucosal cells, small intestinal mucosal cells, colonic mucosal cells, duodenal mucosal cells), skin cells (e.g., epidermal cells, epithelial cells, dermal cells, endothelial cells), vascular cells (e.g., vascular parietal cells, vascular endothelial cells, vascular endothelial cells, vascular smooth muscle cells), etc. In certain embodiments, the wild-type MG53 or MG53 mutants of the present invention can repair cardiomyocytes, skeletal muscle cells, striated muscle cells, proximal renal tubular epithelial cells, alveolar epithelial cells, etc.

The cell membrane repair function of the MG53 mutants as described herein can be determined using methods well known in the art. For example, the cell membrane repair function of the MG53 mutants of the present invention can be determined by overexpressing wild-type MG53 and the MG53 mutants of the present invention using adenovirus in neonatal rat ventricular myocytes (NRVMs), using hypoxia to stimulate cells and detecting the survival of cells (for example, by MTT method, ATP and LDH concentration measurements in medium, TUNEL staining (for detailed steps please refer to Zhang. T et al., *Nature Medicine,* 175-184 (2016)), etc.), and then comparing the indicators (e.g. intracellular ATP level, LDH releasing level, etc.) of control groups (e.g. empty vector negative control groups without the expression of wild-type MG53 and MG53 mutants, positive control group overexpressing wild-type MG53) and test group (i.e. the group overexpressing the MG53 mutants of the present invention).

As used herein, "cardioprotective function" refers that the wild-type MG53 or MG53 mutants can repair myocardial cell membrane damage during myocardial injury, especially acute myocardial injury, optionally, through activating myocardial cell-related signaling pathways (e.g., the RISK pathway) to achieve the protection of cardiomyocyte and thereby enhance the cardiac protection. The cardioprotective function of the MG53 mutants as described herein can be determined using methods well known in the art. For example, the cardioprotective function of the MG53 mutants of the present invention can be determined by overexpressing wild-type MG53 and the MG53 mutants of the present invention using adenovirus in neonatal rat ventricular myocytes (NRVMs), using hypoxia to stimulate cells and detecting the survival of cells (for example, by MTT method, ATP and LDH concentration measurements in medium, TUNEL staining (for detailed steps please refer to Zhang. T et al., *Nature Medicine*, 175-184 (2016)), etc.), and then comparing the indicators (e.g. intracellular ATP level, LDH releasing level, etc.) of control groups (e.g. empty vector negative control groups without the expression of wild-type MG53 and MG53 mutants, positive control group overexpressing wild-type MG53) and test group (i.e. the group overexpressing the MG53 mutants of the present invention). For another example, cardiomyocytes are incubated with wild-type MG53 and the MG53 mutants as described herein, respectively, various stimuli (e.g., hypoxia, $H_2O_2$) are used to lead to cell death, and the cardioprotective function of the MG53 mutants as described herein are evaluated by comparing the survival rates in control groups (e.g., negative control group that is neither incubated with wild-type MG53 nor MG53 mutants, positive control group overexpressing wild-type MG53) and test group (i.e., the group incubated with MG53 mutants of the present invention). The cell survival rate can be determined by MTT cell count, LDH, ATP, or TUNEL staining measurements.

As used herein, "metabolic side effects" refers to diseases or discomforts due to metabolic disorders that are outside of the therapeutic purpose after administration of a therapeutic amount of a drug, including, but not limited to, insulin resistance, obesity, diabetes, high blood pressure, dyslipidemia, etc. Without wishing to be bound by any theory, it is believed that the severity of metabolic side effects can be assessed by measuring E3 ubiquitin ligase activity of MG53. In certain embodiments, when at least one serine in the coiled-coil-SPRY region of the wild-type MG53 is deleted and/or mutated into any other non-serine or non-threonine amino acid(s), at least 40%, at least 50%, at least 60%, at least 70%, at least 75%, at least 80%, at least 85%, at least 90%, at least 95%, at least 98%, at least 99%, or even 100% of the E3 ubiquitin ligase activity of a wild-type MG53 would be inhibited, thereby avoiding or reducing the metabolic side effects caused by wild-type MG53 without having any impact on the cell membrane repair function and/or cardioprotective function of MG53. "Avoiding or reducing the metabolic side effects caused by wild-type MG53" refers to the absence of metabolic side effects caused by wild-type MG53 or the reduction in severity of metabolic side effects caused by wild-type MG53 by at least 40%, at least 50%, at least 60%, at least 70%, at least 75%, at least 80%, at least 85%, at least 90%, at least 95%, at least 98%, at least 99%, or even 100% compared to the corresponding wild-type MG53. "Without having any impact on the cell membrane repair function and/or cardioprotective function of MG53" refers the complete retention of cell membrane repair function and/or cardioprotective function of MG53, or the reduction of cell membrane repair function and/or cardioprotective function of MG53 by up to 5%, up to 10%, up to 15%, up to 20%, up to 25%, up to 30%, etc.

In certain embodiments, the MG53 mutants provided herein comprises their analogs. The MG53 mutant analog refers to a polypeptide having a functional or structural characteristic that is substantially similar to all or part of the MG53 mutant provided herein, however, the amino acid sequence of the MG53 mutant analog differs from the amino acid sequence of the wild-type MG53 by at least one amino acid position. The MG53 mutant analog may be a partial fragment, derivative or variant of the MG53 mutant, and may comprise chemical or biological modifications. The MG53 mutant analog may have conservative substitutions, additions, deletions, insertions, truncations, modifications (e.g., phosphorylation, glycosylation, labeling, etc.) or any combination thereof on one or more amino acids of the MG53 mutant. The MG53 mutant analog may include naturally-occurring variants and artificially-produced variants of the MG53 mutant, such as artificial polypeptide sequences obtained by recombinant methods or chemical synthesis. The MG53 mutant analogs may comprise non-naturally occurring amino acid residues. A person skilled in the art will comprehend that the MG53 mutant analogs described herein still retain substantially similar functions as the MG53 mutants, for example, the MG53 mutant analogs may avoid or reduce the metabolic side effects caused by wild-type MG53, such as insulin resistance, obesity, diabetes, hypertension, dyslipidemia, etc., while still retaining cell membrane repair function and/or cardioprotective function.

Conservative substitutions of amino acid residues refer to substitutions between amino acids with similar characteristics, such as substitutions between polar amino acids (e.g. substitutions between glutamine and asparagine), substitutions between hydrophobic amino acids (e.g. substitution among arginine, isoleucine, methionine and valine), and substitutions between amino acids with the same charge (e.g. substitutions among arginine, lysine and histidine, or between glutamine and aspartate), etc. In certain embodiments, the sequence of the MG53 mutant described herein has conservative substitution at only one or more non-serine positions compared to the sequence set forth in SEQ ID NOs: 7-12, or SEQ ID NOs: 147-150. In certain embodiments, the sequence of the MG53 mutant described herein has conservative substitution at 2, 3, 4, 5, 6, 7, 8, 9, 10, 15, or 20 non-serine positions compared to the sequence set forth in SEQ ID NOs: 7-12, or SEQ ID NOs: 147-150.

The MG53 mutants described herein may also contain non-natural amino acids, on the premises that the activity is not affected. Non-natural amino acids include, for example, β-fluoroalanine, 1-methylhistidine, γ-methylene glutamate, α-methyl leucine, 4,5-dehydrolysine, hydroxyproline, 3-fluorophenylalanine, 3-aminotyrosine, 4-methyltryptophan, etc.

MG53 mutants of the present invention also can be modified using methods well known in the art. For example, but not limited to, PEGylation, glycosylation, amino-terminal modification, fatty acylation, carboxyl-terminal modification, phosphorylation, methylation, etc.

A person skilled in the art will comprehend that the MG53 mutants of the present invention still retain functions substantially similar to the MG53 mutants after being modified by methods well known in the art. For example, the modified MG53 mutants may avoid or reduce metabolic side effects caused by wild-type MG53, such as insulin resistance, obesity, diabetes, hypertension, dyslipidemia, etc., while still retaining cell membrane repair function and/or cardioprotective function.

In another aspect, the present invention relates to a pharmaceutical composition comprising the MG53 mutant described herein and a pharmaceutically acceptable carrier.

As used herein, the term "pharmaceutically acceptable carrier" refers to a pharmaceutically acceptable solvent, suspending agent, or any other pharmacologically inert vehicles used to deliver MG53 mutants to a subject without interfering the structure and properties of MG53 mutants. Some of such carriers may enable MG53 mutants to be formulated, for example, as tablets, pills, capsules, liquids, gels, syrups, slurries, suspensions and troches for oral administration to the subject. Some of such carriers enable MG53 mutants to be formulated as injections, infusions or topical administration.

The pharmaceutically acceptable carriers for use in the pharmaceutical compositions of the present invention may include, but are not limited to, for example, pharmaceutically acceptable liquids, gels, or solid carriers, aqueous vehicles (e.g., sodium chloride injection, Ringer's injection, isotonic glucose injection, sterile water injection, or Ringer's injection of glucose and lactate), non-aqueous vehicles (e.g., fixed oils of vegetable origin, cottonseed oil, corn oil, sesame oil, or peanut oil), antimicrobial agents, isotonic agents (such as sodium chloride or dextrose), buffers (such as phosphate or citrate buffers), antioxidants (such as sodium bisulfate), anesthetics (such as procaine hydrochloride), suspending/dispending agents (such as sodium carboxymethylcellulose, hydroxypropyl methylcellulose, or polyvinylpyrrolidone), chelating agents (such as EDTA (ethylenediamine tetraacetic acid) or EGTA (ethylene glycol tetraacetic acid)), emulsifying agents (such as Polysorbate 80 (TWEEN-80)), diluents, adjuvants, excipients, or non-toxic auxiliary substances, other components known in the art, or various combinations thereof. Suitable components may include, for example, fillers, binders, disintegrants, buffers, preservatives, lubricants, flavorings, thickeners, coloring agents, or emulsifiers.

In certain embodiments, the pharmaceutical composition is an oral formulation. The oral formulations include, but are not limited to, capsules, cachets, pills, tablets, troches (for taste substrates, usually sucrose and acacia or tragacanth), powders, granules, or aqueous or non-aqueous solutions or suspensions, or water-in-oil or oil-in-water emulsions, or elixirs or syrups, or confectionery lozenges (for inert bases, such as gelatin and glycerin, or sucrose or acacia) and/or mouthwash and its analogs.

In certain embodiments, the oral solid formulation (e.g., capsules, tablets, pills, dragees, powders, granules, etc.) includes the MG53 mutant and one or more pharmaceutically acceptable carriers, such as sodium citrate or dicalcium phosphate, and/or the followings: (1) fillers or extenders such as starch, lactose, sucrose, glucose, mannitol and/or silicic acid; (2) binders such as, carboxymethylcellulose, alginates, gelatin, polyvinylpyrrolidone, sucrose, and/or acacia; (3) humectants such as glycerol; (4) cleaving agents such as agar, calcium carbonate, potato or tapioca starch, alginic acid, certain silicates, and sodium carbonate; (5) retarder solutions such as paraffin; (6) accelerating absorbers such as quaternary ammonium compounds; (7) lubricants such as acetyl alcohol and glycerol monostearate; (8) absorbents such as kaolin and bentonite; (9) lubricants such as talc, calcium stearate, magnesium stearate, solid polyethylene glycol, sodium sulfate, and mixtures thereof; and (10) colorants.

In certain embodiments, the oral liquid formulation includes pharmaceutically acceptable emulsions, microemulsions, solutions, suspensions, syrups and elixirs, etc. In addition to the MG53 mutant, the liquid dosage forms may also contain conventional inert diluents such as water or other solvents, solubilizers and emulsifiers such as ethanol, isopropanol, ethyl carbonate, ethyl acetate, benzyl alcohol, benzene (meth) acrylate, propylene glycol, 1,3-butylene glycol, oils (in particular, cottonseed, groundnut, corn, olive, castor and sesame oils), glycerol, tetrahydrofurfuryl alcohol, polyethylene glycol and fatty acid sorbitol esters, and mixtures thereof. Besides inert diluents, the oral compositions may also contain adjuvants such as wetting agents, emulsifying and suspending agents, sweetening, flavoring, coloring, flavoring and preserving agents.

In certain embodiments, the pharmaceutical composition may be an injectable formulation, including sterile aqueous solutions or dispersions, suspensions or emulsions. In all cases, the injectable formulation should be sterile and should be liquid to facilitate injections. It should be stable under the conditions of manufacture and storage, and should be resistant to the infection of microorganisms (such as bacteria and fungi). The carrier may be a solvent or dispersion medium containing, for example, water, ethanol, polyols (e.g., glycerol, propylene glycol, and liquid polyethylene glycols, etc.) and suitable mixtures and/or vegetable oils thereof. The injectable formulation should maintain proper fluidity, which may be maintained in a variety of ways, for example, using a coating such as lecithin, using a surfactant, etc. Antimicrobial contamination can be achieved by the addition of various antibacterial and antifungal agents (e.g., parabens, chlorobutanol, phenol, sorbic acid, thimerosal, etc.).

In certain embodiments, the pharmaceutical composition is an oral spray formulation or nasal spray formulation. Such spray formulations include, but are not limited to, aqueous aerosols, non-aqueous suspensions, liposomal formulations, or solid particulate formulations, etc. Aqueous aerosols are formulated by combining an aqueous solution or suspension of the agent with a conventional pharmaceutically acceptable carrier and stabilizer. The carrier and stabilizer may vary according to the needs of specific compounds, but generally include nonionic surfactants (Tweens, or polyethylene glycol), oleic acid, lecithin, amino acids such as glycine, buffers, salts, sugar or sugar alcohol. Aerosols are usually prepared from isotonic solutions and can be delivered by nebulizers.

In certain embodiments, the pharmaceutical compositions may be used in combination with one or more other drugs. In certain embodiments, the composition comprises at least one other drug. In certain embodiments, the other drugs are cardiovascular drugs, drugs for treating kidney diseases, drugs for cell membrane repair, etc.

In certain embodiments, the pharmaceutical compositions may be delivered to the subject by suitable routes including, but not limited to, the oral route, injection route (e.g., intravenous injection, intramuscular injection, subcutaneous injection, intradermal injection, intracardiac injection, intrathecal injection, intrapleural injection, intraperitoneal injection, etc.), mucosal route (e.g., intranasal administration, oral administration, etc.), sublingual route, rectal route, transdermal route, intraocular route, pulmonary route. In certain embodiments, the pharmaceutical compositions can be administered by injection route.

In another aspect, the present invention relates to an isolated nucleic acid comprising a nucleic acid sequence encoding the amino acid sequence of the MG53 mutant described herein.

As used herein, the term "isolated" refers to a substance (such as a polypeptide or a nucleic acid) is separated from the environment in which it is normally present in nature or in an environment different from the environment in which it is normally found in nature.

As used herein, the term "nucleic acid" or "polynucleotide" refers to ribonucleic acid (RNA), deoxyribonucleic acid (DNA), or a mixture of ribonucleoside-deoxyribonucleic acids such as DNA-RNA hybrids. The nucleic acids or polynucleotides can be single- or double-stranded DNA, RNA, or DNA-RNA hybrids. Nucleic acids or polynucleotides may be linear or cyclic. As used herein, the term "encoding" or "encoding for . . . " means capable of transcription into mRNA and/or translation into a peptide or protein. The term "encoding sequence" or "gene" refers to a polynucleotide sequence encoding an mRNA, peptide or protein. These two terms can be used interchangeably in the present application.

In certain embodiments, the isolated nucleic acid comprises any one of the nucleic acid sequences set forth in SEQ ID NOs: 13-18.

SEQ ID NO: 13 is a nucleic acid sequence encoding the amino acid sequence set forth in SEQ ID NO: 7, and its specific sequence is shown in FIG. 8.

SEQ ID NO: 14 is a nucleic acid sequence encoding the amino acid sequence set forth in SEQ ID NO: 8, and its specific sequence is shown in FIG. 9.

SEQ ID NO: 15 is a nucleic acid sequence encoding the amino acid sequence set forth in SEQ ID NO: 9, and its specific sequence is shown in FIG. 10.

SEQ ID NO: 16 is a nucleic acid sequence encoding the amino acid sequence set forth in SEQ ID NO: 10, and its specific sequence is shown in FIG. 11.

SEQ ID NO: 17 is a nucleic acid sequence encoding the amino acid sequence set forth in SEQ ID NO: 11, and its specific sequence is shown in FIG. 12.

SEQ ID NO: 18 is a nucleic acid sequence encoding the amino acid sequence set forth in SEQ ID NO: 12, and its specific sequence is shown in FIG. 13.

In certain embodiments, the isolated nucleic acid comprises any one of the nucleic acid sequences set forth in SEQ ID NOs: 151-154.

SEQ ID NO: 151 is a nucleic acid sequence encoding the amino acid sequence set forth in SEQ ID NO: 147, and its specific sequence is shown in FIG. 24.

SEQ ID NO: 152 is a nucleic acid sequence encoding the amino acid sequence set forth in SEQ ID NO: 148, and its specific sequence is shown in FIG. 25.

SEQ ID NO: 153 is a nucleic acid sequence encoding the amino acid sequence set forth in SEQ ID NO: 149, and its specific sequence is shown in FIG. 26.

SEQ ID NO: 154 is a nucleic acid sequence encoding the amino acid sequence set forth in SEQ ID NO: 150, and its specific sequence is shown in FIG. 27.

In certain embodiments, the isolated nucleic acids provided herein comprise the nucleic acid sequence that has at least 70% homology, e.g., at least 75%, at least 80%, at least 85%, at least 90%, at least 95%, or at least 99% homology to any one of the nucleic acid sequences set forth in SEQ ID NOs: 13-18, SEQ ID NOs: 151-154, and can still encode one of the amino acid sequences set forth in SEQ ID NOs: 7-12, SEQ ID NOs: 147-150.

In certain embodiments, the present invention provides nucleic acid sequences encoding SEQ ID NOs: 7-12, SEQ ID NOs: 147-150, but they are different from any one of the nucleic acid sequences set forth in SEQ ID NOs: 13-18, SEQ ID NOs: 151-154 due to the degeneracy of the genetic code.

As used herein, the term "degeneracy of the genetic code" refers to a phenomenon that one amino acid has two or more corresponding genetic codons. For example, proline has 4 synonymous codons CCU, CCC, CCA, and CCG. It is well-known in the art that due to the degeneracy of genetic codes, it is possible to replace nucleic acids in certain positions in a given nucleic acid sequence without changing the encoded amino acid sequence. It is trivial for a person skilled in the art to conduct the replacement of degeneracy of the genetic code by, for example, the site-directed mutagenesis of bases. Different organisms have developed different preferences for different codons. In order to express the polypeptide of the present invention in a selected biological cell, the preferred codon of the biological cell can be selected to obtain the corresponding coding sequence, and the MG53 mutant sequence (e.g., SEQ ID NOs: 7-12, SEQ ID NOs: 147-150) of the present invention can be obtained by recombinant expression.

In another aspect, the present invention related to an expression vector comprising the encoding sequence of the amino acid sequence of the MG53 mutant described herein.

The expression vector in the present invention may be, for example, a DNA plasmid, a bacterial plasmid, a virus, etc. Non-limiting examples of expression vectors are described in, e.g. Paul et al., 2002, *Nature Biotechnology*, 19, 505; Miyagishi and Taira, 2002, *Nature Biotechnology*, 19, 497; Lee et al., 2002, *Nature Biotechnology*, 19, 500; and Novina et al. 2002, *Nature Medicine*, advance online publication doi:10.1038/nm725. The expression vector may further contain a promoter operably linked to the encoding sequence of the amino acid sequence of the MG53 mutant, so that the promoter may initiate the expression of the encoding sequence after the expression vector enters the host cell. The expression vector can be introduced into the host cell by a suitable method such as, but not limited to, calcium phosphate transfection, lipofection transfection, electroporation transfection, bacterial heat shock, etc. For details, please refer to Sambrook et al. Molecular Cloning (a laboratory manual, Cold Spring Harbor, 1989). In certain embodiments, the expression vectors described herein comprise any one of the nucleic acid sequences set forth in SEQ ID NOs: 13-18.

In another aspect, the present invention relates to a host cell comprising the expression vector described herein.

The host cell described in the present invention can be a eukaryotic cell or a prokaryotic cell. Suitable eukaryotic cells may include, for example, mammalian cells such as Chinese hamster ovary cells (CHO). Suitable prokaryotic cells may include, for example, bacteria such as *E. coli*.

In another aspect, the present invention relates to a method for preparing the MG53 mutants, and the MG53 mutants provided herein can be prepared by techniques known in the art. For example, they can be prepared by chemical synthesis or genetic engineering.

Chemical synthesis methods mainly include solid-phase synthesis and liquid-phase synthesis. Solid-phase polypeptide synthesis methods include, for example, the Merrifield solid-phase synthesis method, which is described in detail in the literature "Merrifield, *J. Am. Chem. Soc.* 85: 2149-2154" and "M. Bodanszky et al., *Peptide Synthesis*, John Wiley & Sons, Second Edition, 1976" and "J. Meienhofer, *Hormonal Proteins and Peptides*, Vol. 2, p. 46, Academic Press (New York), 1983". The entire contents of these documents are hereby incorporated into this application as references. The Merrifield solid-phase synthesis mainly includes the following steps: attaching the protected C-terminal amino acid of the peptide to the resin based on the amino acid sequences of the target protein. After attachment the resin is filtered, washed and the protecting group (e.g. t-butyloxycarbonyl)

on the alpha amino group of the C-terminal amino acid is removed. The removal of this protecting group must take place, of course, without breaking the bond between that amino acid and the resin. The resulting resin peptide is then coupled to the penultimate C-terminal protected amino acid. This coupling takes place by the formation of an amide bond between the free carboxy group of the second amino acid and the amino group of the first amino acid attached to the resin. This sequence of events is repeated with successive amino acids until all amino acids of the peptide are attached to the resin. Finally, the protected peptide is cleaved from the resin and the protecting groups removed to obtain the desired peptide. The polypeptides disclosed herein can also be prepared by liquid-phase synthesis, for example, by the standard solution peptide synthesis, which has been described in "E. Schroder and K. Kubke, *The Peptides*, Vol. 1, Academic Press (New York), 1965" in detail, which is incorporated herein in its entirety by reference. Liquid-phase synthesis mainly includes coupling amino acids or peptide fragments step by step by chemical or enzymic methods that form amide bonds.

The genetic engineering method is a method of expressing a nucleic acid sequence encoding the corresponding MG53 mutant in a proper host cell to generate the corresponding mutant. For a detailed description of this method, see Sambrook et al. Molecular Cloning (a laboratory manual, Cold Spring Harbor, 1989). In certain embodiments, the method for preparing the MG53 mutant provided herein comprises determining one or more serine positions for mutation, performing site-directed mutagenesis at said position on the full-length sequence of a plasmid comprising a nucleic acid sequence encoding the amino acid sequence of a wild-type MG53, transfecting the plasmid with site-directed mutagenesis into a host cell, and inducing the host cell to produce the MG53 mutant.

As used herein, the term "site-directed mutagenesis" refers to the introduction of an interested change into a target DNA fragment, including additions, deletions, and substitutions of bases, etc. In certain embodiments, the target DNA fragment is the encoding sequence of a wild-type MG53, i.e. SEQ ID NOs: 19-24 and SEQ ID NOs: 143-146. The mutated position is located at one or more serine positions in the encoding sequence of the coiled-coil-SPRY region of the wild-type MG53.

SEQ ID NO: 19 is a nucleic acid sequence encoding the amino acid sequence set forth in SEQ ID NO: 1, and its specific sequence is shown in FIG. 2.

SEQ ID NO: 20 is a nucleic acid sequence encoding the amino acid sequence set forth in SEQ ID NO: 2, and its specific sequence is shown in FIG. 3.

SEQ ID NO: 21 is a nucleic acid sequence encoding the amino acid sequence set forth in SEQ ID NO: 3, and its specific sequence is shown in FIG. 4.

SEQ ID NO: 22 is a nucleic acid sequence encoding the amino acid sequence set forth in SEQ ID NO: 4, and its specific sequence is shown in FIG. 5.

SEQ ID NO: 23 is a nucleic acid sequence encoding the amino acid sequence set forth in SEQ ID NO: 5, and its specific sequence is shown in FIG. 6.

SEQ ID NO: 24 is a nucleic acid sequence encoding the amino acid sequence set forth in SEQ ID NO: 6, and its specific sequence is shown in FIG. 7.

SEQ ID NO: 143 is a nucleic acid sequence encoding the amino acid sequence set forth in SEQ ID NO: 139, and its specific sequence is shown in FIG. 20.

SEQ ID NO: 144 is a nucleic acid sequence encoding the amino acid sequence set forth in SEQ ID NO: 140, and its specific sequence is shown in FIG. 21.

SEQ ID NO: 145 is a nucleic acid sequence encoding the amino acid sequence set forth in SEQ ID NO: 141, and its specific sequence is shown in FIG. 22.

SEQ ID NO: 146 is a nucleic acid sequence encoding the amino acid sequence set forth in SEQ ID NO: 142, and its specific sequence is shown in FIG. 23.

In certain embodiments, the site-directed mutagenesis comprises the following steps:

(1) determining the corresponding nucleotide site of the amino acid targeted for site-directed mutagenesis in the cDNA sequence, modifying the nucleotide sequence at the mutation site according to the target amino acid, and designing primers by intercepting a sequence of 20-40 bp in length comprising the mutation site;

(2) performing PCR reaction by using the primers of step (1) and taking a wild type MG53 plasmid as a template, performing agarose gel electrophoresis for the PCR product, and purifying the PCR product;

(3) performing enzymatic reaction for the purified PCR product of step (2) by using restriction endonuclease, ligating the enzyme-digested product with a suitable plasmid expression vector, transforming and cultivating the ligation product in bacterial competent cells.

In certain embodiments, the site-directed mutagenesis further comprises the following step:

(4) selecting the clones of step (3) to perform colony PCR identification by using the primers of step (1), performing agarose gel electrophoresis for the PCR product, and then performing DNA sequencing identification to identify positive clones with the site-directed mutagenesis.

Site-directed mutagenesis of a wild-type MG53 can be carried out using a variety of commercially available site-directed mutagenesis kits, for example, with reference to the instructions for the Easy Mutagenesis System Kit from Beijing Transgen Biotech, which details the method and procedures for site-directed mutagenesis.

In another aspect, the present invention relates to use of the MG53 mutant in the manufacture of a medicament for treating heart diseases, diabetic cerebrovascular diseases, diabetic ocular complications, diabetic neuropathy, diabetic foot, kidney diseases, and diseases associated with cellular and/or tissue damage. In certain embodiments, the medicament may avoid or reduce metabolic side effects, such as insulin resistance, obesity, diabetes, hypertension, dyslipidemia, while treating heart diseases, diabetic cerebrovascular diseases, diabetic ocular complications, diabetic neuropathy, diabetic foot, kidney diseases, and diseases associated with cellular and/or tissue damage. In certain embodiments, the heart diseases are diseases associated with myocardial damage, including but not limited to, diabetic heart disease, myocardial ischemia, cardiac ischemia/reperfusion injury, myocardial infarction, heart failure, arrhythmia, heart rupture, angina, myocarditis, coronary heart disease, and pericarditis. In certain embodiments, the diabetic cerebrovascular diseases include, but are not limited to, cerebral arteriosclerosis, ischemic cerebrovascular disease, cerebral hemorrhage, cerebral atrophy, and cerebral infarction. In certain embodiments, the diabetic ocular complications include, but are not limited to, diabetic retinopathy, diabetic cataract, diabetic associated uveitis, and blindness. In certain embodiments, the diabetic neuropathy includes, but is not limited to, diabetic peripheral neuropathy. In certain embodiments, the kidney diseases include, but are not limited to, acute glomerulonephritis, chronic glomerulonephritis, nephrotic syndrome, acute kidney injury, diabetic nephropathy, etc. In certain embodiments, the diseases associated with cellular and/or tissue damage include, but are not limited to, diseases associated with the cellular and/or tissue damage of kidney, brain, lung, liver, heart, spleen, digestive tract, and skin, such as brain injury, lung injury, spleen injury, splenic rupture, gastric ulcer, gastritis, gastric perforation, gastrointestinal mucosal injury, trauma, burns, ulcers, mucositis, asthma, chronic obstructive pulmonary disease (COPD), stroke, skin aging, etc. In certain embodiments, the present invention relates to use of a polypeptide set forth in SEQ ID NO: 7 in the manufacture of a medicament for treating heart diseases, diabetic cerebrovascular diseases, diabetic ocular complications, diabetic neuropathy, diabetic foot, kidney diseases, and diseases associated with cellular and/or tissue damage. In certain embodiments, the present invention relates to use of a polypeptide set forth in SEQ ID NO: 147, SEQ ID NO: 148, SEQ ID NO: 149 or SEQ ID NO: 150 in the manufacture of a medicament for treating heart diseases, diabetic cerebrovascular diseases, diabetic ocular complications, diabetic neuropathy, diabetic foot, kidney diseases, and diseases associated with cellular and/or tissue damage.

In yet another aspect, the present invention relates to a method of treating heart diseases, diabetic cerebrovascular diseases, diabetic ocular complications, diabetic neuropathy, diabetic foot, kidney diseases, and diseases associated with cellular and/or tissue damage, comprising administering to a subject in need thereof a therapeutically effective amount of the MG53 mutant. In certain embodiments, the MG53 mutant may avoid or reduce metabolic side effects, such as insulin resistance, obesity, diabetes, hypertension, and dyslipidemia, while treating heart diseases, diabetic cerebrovascular diseases, diabetic ocular complications, diabetic neuropathy, diabetic foot, kidney diseases, and diseases associated with cellular and/or tissue damage. In certain embodiments, the heart diseases are diseases associated with myocardial damage, including but not limited to, diabetic heart disease, myocardial ischemia, cardiac ischemia/reperfusion injury, myocardial infarction, heart failure, arrhythmia, heart rupture, angina, myocarditis, coronary heart disease, and pericarditis. In certain embodiments, the diabetic cerebrovascular diseases include, but are not limited to, cerebral arteriosclerosis, ischemic cerebrovascular disease, cerebral hemorrhage, cerebral atrophy, and cerebral infarction. In certain embodiments, the diabetic ocular complications include, but are not limited to, diabetic retinopathy, diabetic cataract, diabetic associated uveitis, and blindness. In certain embodiments, the diabetic neuropathy includes, but is not limited to, diabetic peripheral neuropathy. In certain embodiments, the kidney diseases include, but are not limited to, acute glomerulonephritis, chronic glomerulonephritis, nephrotic syndrome, acute kidney injury, diabetic nephropathy, etc. In certain embodiments, the diseases associated with cellular and/or tissue damage include, but are not limited to, diseases associated with the cellular and/or tissue damage of kidney, brain, lung, liver, heart, spleen, digestive tract, and skin, such as brain injury, lung injury, spleen injury, splenic rupture, gastric ulcer, gastritis, gastric perforation, gastrointestinal mucosal injury, trauma, burns, ulcers, mucositis, asthma, chronic obstructive pulmonary disease (COPD), stroke, skin aging, etc. In certain embodiments, the present invention relates to a method of treating heart diseases, diabetic cerebrovascular diseases, diabetic ocular complications, diabetic neuropathy, diabetic foot, kidney diseases, and diseases associated with cellular and/or tissue damage, comprising administering to a subject in need thereof a therapeutically effective amount of the polypeptide set forth in SEQ ID NO: 7. In certain embodiments, the present invention relates to a method of treating heart diseases, diabetic cerebrovascular diseases, diabetic ocular complications, diabetic neuropathy, diabetic foot, kidney diseases, and diseases associated with cellular and/or tissue damage, comprising administering to a subject in need thereof a therapeutically effective amount of a polypeptide set forth in SEQ ID NO: 147, SEQ ID NO: 148, SEQ ID NO: 149, or SEQ ID NO: 150.

As used herein, the term "therapeutically effective amount" refers to the amount of a medicament which achieves a therapeutic effect by inhibiting or alleviating a disease and disorder of a subject, or by prophylactically inhibiting or preventing the onset of a disease or disorder. A therapeutically effective amount may be the amount of the medicament which relieves to some extent one or more symptoms of a disease or disorder in a subject; returns to normal either partially or completely one or more physiological or biochemical parameters associated with or causative of the disease or disorder; and/or reduces the likelihood of the onset of the disease or disorder.

In yet other aspect, the present invention relates to an MG53 mutant for use in treating heart diseases, diabetic cerebrovascular diseases, diabetic ocular complications, diabetic neuropathy, diabetic foot, kidney diseases, and diseases associated with cellular and/or tissue damage. In certain embodiments, the MG53 mutant may avoid or reduce metabolic side effects, such as insulin resistance, obesity, diabetes, hypertension, and dyslipidemia, while treating heart diseases, diabetic cerebrovascular diseases, diabetic ocular complications, diabetic neuropathy, diabetic foot, kidney diseases, and diseases associated with cellular and/or tissue damage. In certain embodiments, the heart diseases are diseases associated with myocardial damage, including but not limited to, diabetic heart disease, myocardial ischemia, cardiac ischemia/reperfusion injury, myocardial infarction, heart failure, arrhythmia, heart rupture, angina, myocarditis, coronary heart disease, and pericarditis. In certain embodiments, the diabetic cerebrovascular diseases include, but are not limited to, cerebral arteriosclerosis, ischemic cerebrovascular disease, cerebral hemorrhage, cerebral atrophy, and cerebral infarction. In certain embodiments, the diabetic ocular complications include, but are not limited to, diabetic retinopathy, diabetic cataract, diabetic associated uveitis, and blindness. In certain embodiments, the diabetic neuropathy includes, but is not limited to, diabetic peripheral neuropathy. In certain embodiments, the kidney diseases include, but are not limited to, acute glomerulonephritis, chronic glomerulonephritis, nephrotic syndrome, acute kidney injury, diabetic nephropathy, etc. In certain embodiments, the diseases associated with cellular and/or tissue damage include, but are not limited to, diseases associated with the cellular and/or tissue damage of kidney, brain, lung, liver, heart, spleen, digestive tract, and skin, such as brain injury, lung injury, spleen injury, splenic rupture, gastric ulcer, gastritis, gastric perforation, gastrointestinal mucosal injury, trauma, burns, ulcers, mucositis, asthma, chronic obstructive pulmonary disease (COPD), stroke, skin aging, etc. In certain embodiments, the present invention relates to a polypeptide set forth in SEQ ID NO: 7 for use in treating heart diseases, diabetic cerebrovascular diseases, diabetic ocular complications, diabetic neuropathy, diabetic foot, kidney diseases, and diseases associated with cellular and/or tissue damage. In certain embodiments, the present invention relates to a polypeptide set forth in SEQ ID NO: 147, SEQ ID NO: 148, SEQ ID NO: 149, or SEQ ID NO: 150 for use in treating heart diseases, diabetic cerebrovascular diseases, diabetic ocular complications, diabetic neuropathy, diabetic foot, kidney diseases, and diseases associated with cellular and/or tissue damage.

EMBODIMENTS

The biological materials used in all examples such as *E. Coli* strains, various clones and expression plasmids, media, enzymes, buffer solutions, and various culturing methods, protein extraction and purification methods, and the other molecular biological operation methods, are all well-known to persons skilled in the art. For more details, please refer to the "Molecular Cloning: A Laboratory Manual" edited by Sambrook, et al. (Cold Spring Harbor, 1989) and "Short Protocols in Molecular Biology" (Frederick M. Ausubel, et al., translated by Yan Ziying et al., Science Press (Beijing), 1998).

Example 1: Preparation of MG53 Mutants

1. Preparation of Human MG53 Mutants

Human MG53 S255A Mutant (1) Primer design: determining the corresponding nucleotide site of the amino acid targeted for site-directed mutagenesis in the cDNA sequence, modifying the nucleotide sequence at the mutation site according to the mutated amino acid, and designing primers by intercepting a sequence of 20 bp upstream and 10 bp downstream the mutation site. The sequences of the primers are as follows:

```
Forward primer of human MG53 S255A:
                            (SEQ ID NO: 25)
tgcagaagatcctggcagaggctcccccacccg Reverse primer of human MG53 S255A:
                            (SEQ ID NO: 26)
tccagacgggcgggtgggggagcctctgccagg
```

(2) Polymerase chain reaction (PCR) of plasmid full-length clone: performing PCR reaction by using the designed primers for site-directed mutagenesis, using Taq Polymerase High Fidelity, and taking the original gene expression plasmid as a template. The reaction system and conditions are as follows:

| template | $x$ μl |
|---|---|
| primer-$F$ | 0.5 μl |
| primer-$R$ | 0.5 μl |
| 2×Taq Mix | 10 μl |
| ddH2O | 9-$x$ μl |
| total | 20 μl |

95° C. 5 min
95° C. 5 min ⎫
55° C. 30 sec ⎬ 30 cycles
72° C. $Y$ min ⎭
72° C. 10 min
5° C. ∞

Agarose gel electrophoresis of the PCR product: performing agarose gel electrophoresis for the PCR product to identify its purity and quantity.

Ethanol precipitation of the PCR product: purifying the PCR product with correct size and a single band by the method of ethanol precipitation.

Dpn I digestion: performing enzymatic reaction for the purified PCR product by using restriction endonuclease Dpn I.

Transformation of enzyme-digested product: transforming the Dpn I-digested product in bacterial competent cells, coating onto an appropriate screen plate for cultivation.

Identification of positive clones: selecting the clones with proper size to perform colony PCR identification, performing agarose gel electrophoresis for the PCR product, performing small-volume shaking amplification cultivation for the clone with a clear band and correct size, and then performing sequencing identification.

The same method was used to prepare human MG53 S255G, S255L, S255V, S255P, S255F, S255W, S255Q, S255C, S255Y, S255D, S255R, S211A, S214A, S246A, S269A, S296A, S297A mutants. Except for the primers, all of the other steps are the same as the steps for preparing human MG53 S255A mutant. The primers of each mutant are as follows:

(i) the forward and reverse primers of human MG53 S255G, which represents an MG53 mutant in which serine at position 255 of human wild-type MG53 (i.e. SEQ ID NO: 1) is mutated into glycine.

```
Forward primer of human MG53 S255G:
                            (SEQ ID NO: 27)
tgcagaagatcctggcagagggtcccccacccg Reverse primer of human MG53 S255G:
                            (SEQ ID NO: 28)
tccagacgggcgggtgggggaccctctgccagg
```

(ii) the forward and reverse primers of human MG53 S255L, which represents an MG53 mutant in which serine at position 255 of human wild-type MG53 (i.e. SEQ ID NO: 1) is mutated into leucine.

```
Forward primer of human MG53 S255L:
                            (SEQ ID NO: 29)
tgcagaagatcctggcagagcttcccccacccg Reverse primer of human MG53 S255L:
                            (SEQ ID NO: 30)
tccagacgggcgggtgggggaagctctgccagg
```

(iii) the forward and reverse primers of human MG53 S255V, which represents an MG53 mutant in which serine at position 255 of human wild-type MG53 (i.e. SEQ ID NO: 1) is mutated into valine.

```
Forward primer of human MG53 S255V:
                            (SEQ ID NO: 31)
tgcagaagatcctggcagaggttcccccacccg Reverse primer of human MG53 S255V:
                            (SEQ ID NO: 32)
tccagacgggcgggtgggggaacctctgccagg
```

(iv) the forward and reverse primers of human MG53 S255P, which represents an MG53 mutant in which serine at position 255 of human wild-type MG53 (i.e. SEQ ID NO: 1) is mutated into proline.

```
Forward primer of human MG53 S255P:
                                    (SEQ ID NO: 33)
tgcagaagatcctggcagagcctcccccacccg Reverse primer of human MG53 S255P:
                                    (SEQ ID NO: 34)
tccagacgggcgggtgggggaggctctgccagg
```

(v) the forward and reverse primers of human MG53 S255F, which represents an MG53 mutant in which serine at position 255 of human wild-type MG53 (i.e. SEQ ID NO: 1) is mutated into phenylalanine.

```
Forward primer of human MG53 S255F:
                                    (SEQ ID NO: 35)
tgcagaagatcctggcagagtttcccccacccg Reverse primer of human MG53 S255F:
                                    (SEQ ID NO: 36)
tccagacgggcgggtgggggaaactctgccagg
```

(vi) the forward and reverse primers of human MG53 S255W, which represents an MG53 mutant in which serine at position 255 of human wild-type MG53 (i.e. SEQ ID NO: 1) is mutated into tryptophan.

```
Forward primer of human MG53 S255W:
                                    (SEQ ID NO: 37)
tgcagaagatcctggcagagtggcccccacccg Reverse primer of human MG53 S255W:
                                    (SEQ ID NO: 38)
tccagacgggcgggtgggggccactctgccagg
```

(vii) the forward and reverse primers of human MG53 S255Q, which represents an MG53 mutant in which serine at position 255 of human wild-type MG53 (i.e. SEQ ID NO: 1) is mutated into glutamine.

```
Forward primer of human MG53 S255Q:
                                    (SEQ ID NO: 39)
tgcagaagatcctggcagagcaaccccacccg Reverse primer of human MG53 S255Q:
                                    (SEQ ID NO: 40)
tccagacgggcgggtgggggttgctctgccagg
```

(viii) the forward and reverse primers of human MG53 S255C, which represents an MG53 mutant in which serine at position 255 of human wild-type MG53 (i.e. SEQ ID NO: 1) is mutated into cysteine.

```
Forward primer of human MG53 S255C:
                                    (SEQ ID NO: 41)
tgcagaagatcctggcagagtgtcccccacccg Reverse primer of human MG53 S255C:
                                    (SEQ ID NO: 42)
tccagacgggcgggtgggggacactctgccagg
```

(ix) the forward and reverse primers of human MG53 S255Y, which represents an MG53 mutant in which serine at position 255 of human wild-type MG53 (i.e. SEQ ID NO: 1) is mutated into tyrosine.

```
Forward primer of human MG53 S255Y:
                                    (SEQ ID NO: 43)
tgcagaagatcctggcagagtatcccccacccg Reverse primer of human MG53 S255Y:
                                    (SEQ ID NO: 44)
tccagacgggcgggtgggggatactctgccagg
```

(x) the forward and reverse primers of human MG53 S255D, which represents an MG53 mutant in which serine at position 255 of human wild-type MG53 (i.e. SEQ ID NO: 1) is mutated into aspartic acid.

```
Forward primer of human MG53 S255D:
                                    (SEQ ID NO: 45)
tgcagaagatcctggcagaggatcccccacccg Reverse primer of human MG53 S255D:
                                    (SEQ ID NO: 46)
tccagacgggcgggtgggggctactctgccagg
```

(xi) the forward and reverse primers of human MG53 S255R, which represents an MG53 mutant in which serine at position 255 of human wild-type MG53 (i.e. SEQ ID NO: 1) is mutated into arginine.

```
Forward primer of human MG53 S255R:
                                    (SEQ ID NO: 47)
tgcagaagatcctggcagagcgtcccccacccg Reverse primer of human MG53 S255R:
                                    (SEQ ID NO: 48)
tccagacgggcgggtgggggacgctctgccagg
```

(xii) the forward and reverse primers of human MG53 S255A, which represents an MG53 mutant in which serine at position 255 of human wild-type MG53 (i.e. SEQ ID NO: 1) is mutated into alanine.

```
Forward primer of human MG53 S211A:
                                    (SEQ ID NO: 49)
ccttgcgccgggagctgggggccctgaactctt Reverse primer of human MG53 S211A:
                                    (SEQ ID NO: 50)
gctgctccaggtaagagttcagggcccccagctcc
```

(xiii) the forward and reverse primers of human MG53 S214A, which represents an MG53 mutant in which serine at position 214 of human wild-type MG53 (i.e. SEQ ID NO: 1) is mutated into alanine.

```
Forward primer of human MG53 S214A:
                                    (SEQ ID NO: 51)
gggagctggggagcctgaacgcttacctggagc Reverse primer of human MG53 S214A:
                                    (SEQ ID NO: 52)
tgccgcagctgctccaggtaagcgttcaggctc
```

(xiv) the forward and reverse primers of human MG53 S246A, which represents an MG53 mutant in which serine at position 246 of human wild-type MG53 (i.e. SEQ ID NO: 1) is mutated into alanine.

```
Forward primer of human MG53 S246A:
                                    (SEQ ID NO: 53)
tgaaatactgcctggtgaccgccaggctgcaga
```

-continued

Reverse primer of human MG53 S246A:
(SEQ ID NO: 54)
gccaggatcttctgcagcctggcggtcaccagg (xv) the forward and reverse primers of human MG53 S269A, which represents an MG53 mutant in which serine at position 269 of human wild-type MG53 (i.e. SEQ ID NO: 1) is mutated into alanine.

Forward primer of human MG53 S269A:
(SEQ ID NO: 55)
aggagctgacctttgacccggcctctgcgcacc Reverse primer of human MG53 S296A:
(SEQ ID NO: 56)
accaggctcgggtgcgcagaggccgggtcaaag (xvi) the forward and reverse primers of human MG53 S297A, which represents an MG53 mutant in which serine at position 297 of human wild-type MG53 (i.e. SEQ ID NO: 1) is mutated into alanine.

Forward primer of human MG53 S297A:
(SEQ ID NO: 57)
agctgacctttgacccgagcgctgcgcacccga Reverse primer of human MG53 S297A:
(SEQ ID NO: 58)
accaccaggctcgggtgcgcagcgctcgggtca 2. Preparation of Mouse MG53 Mutants Mouse MG53 S255A, S255G, S255L, S255W, S255Q, S255Y, S255D, and S255R mutants were prepared according to the method for preparing human MG53 S255A mutant. Except for the primers, all of the other steps are the same as the steps for preparing human MG53 S255A mutant. The primers of each mutant are as follows:

(i) the forward and reverse primers of mouse MG53 S255A, which represents an MG53 mutant in which serine at position 255 of mouse wild-type MG53 (i.e. SEQ ID NO: 2) is mutated into alanine.

Forward primer of mouse MG53 S255A:
(SEQ ID NO: 59)
tgcagaagatcctgtcagaggcaccaccaccgg Reverse primer of mouse MG53 S255A:
(SEQ ID NO: 60)
tctagccttgccggtggtggtgcctctgacagg (ii) the forward and reverse primers of mouse MG53 S255G, which represents an MG53 mutant in which serine at position 255 of mouse wild-type MG53 (i.e. SEQ ID NO: 2) is mutated into glycine.

Forward primer of mouse MG53 S255G:
(SEQ ID NO: 61)
tgcagaagatcctgtcagagggaccaccaccgg Reverse primer of mouse MG53 S255G:
(SEQ ID NO: 62)
tctagccttgccggtggtggtccctctgacagg (iii) the forward and reverse primers of mouse MG53 S255L, which represents an MG53 mutant in which serine at position 255 of mouse wild-type MG53 (i.e. SEQ ID NO: 2) is mutated into leucine.

Forward primer of mouse MG53 S255L:
(SEQ ID NO: 63)
tgcagaagatcctgtcagagttaccaccaccgg Reverse primer of mouse MG53 S255L:
(SEQ ID NO: 64)
tctagccttgccggtggtggtaactctgacagg (iv) the forward and reverse primers of mouse MG53 S255W, which represents an MG53 mutant in which serine at position 255 of mouse wild-type MG53 (i.e. SEQ ID NO: 2) is mutated into tryptophan.

Forward primer of mouse MG53 S255W:
(SEQ ID NO: 65)
tgcagaagatcctgtcagagtggccaccaccgg Reverse primer of mouse MG53 S255W:
(SEQ ID NO: 66)
tctagccttgccggtggtggccactctgacagg (v) the forward and reverse primers of mouse MG53 S255Q, which represents an MG53 mutant in which serine at position 255 of mouse wild-type MG53 (i.e. SEQ ID NO: 2) is mutated into glutamine.

Forward primer of mouse MG53 S255Q:
(SEQ ID NO: 67)
tgcagaagatcctgtcagagcaaccaccaccgg Reverse primer of mouse MG53 S255Q:
(SEQ ID NO: 68)
tctagccttgccggtggtggttgctctgacagg (vi) the forward and reverse primers of mouse MG53 S255Y, which represents an MG53 mutant in which serine at position 255 of mouse wild-type MG53 (i.e. SEQ ID NO: 2) is mutated into tyrosine.

Forward primer of mouse MG53 S255Y:
(SEQ ID NO: 69)
tgcagaagatcctgtcagagtatccaccaccgg Reverse primer of mouse MG53 S255Y:
(SEQ ID NO: 70)
tctagccttgccggtggtggatactctgacagg (vii) the forward and reverse primers of mouse MG53 S255D, which represents an MG53 mutant in which serine at position 255 of mouse wild-type MG53 (i.e. SEQ ID NO: 2) is mutated into aspartic acid.

Forward primer of mouse MG53 S255D:
(SEQ ID NO: 71)
tgcagaagatcctgtcagaggatccaccaccgg Reverse primer of mouse MG53 S255D:
(SEQ ID NO: 72)
tctagccttgccggtggtggatcctctgacagg (viii) the forward and reverse primers of mouse MG53 S255R, which represents an MG53 mutant in which serine at position 255 of mouse wild-type MG53 (i.e. SEQ ID NO: 2) is mutated into arginine.

```
Forward primer of mouse MG53 S255R:
                                        (SEQ ID NO: 73)
tgcagaagatcctgtcagagcgaccaccaccgg Reverse primer of mouse MG53 S255R:
                                        (SEQ ID NO: 74)
tctagccttgccggtggtggtcgctctgacagg
```

3. Preparation of Rat MG53 Mutants

Rat MG53 S255A, S255G, S255L, S255W, S255Q, S255Y, S255D, and S255R mutants were prepared according to the method for preparing human MG53 S255A mutant. Except for the primers, all of the other steps are the same as the steps for preparing human MG53 S255A mutant. The primers of each mutant are as follows:

(i) the forward and reverse primers of rat MG53 S255A, which represents an MG53 mutant in which serine at position 255 of rat wild-type MG53 (i.e. SEQ ID NO: 3) is mutated into alanine.

```
Forward primer of rat MG53 S255A:
                                        (SEQ ID NO: 75)
tgcagaagattctgtcagaggcaccaccccag Reverse primer of rat MG53 S255A:
                                        (SEQ ID NO: 76)
tctagccttgctgggggtggtgcctctgacaga
```

(ii) the forward and reverse primers of rat MG53 S255G, which represents an MG53 mutant in which serine at position 255 of rat wild-type MG53 (i.e. SEQ ID NO: 3) is mutated into glycine.

```
Forward primer of rat MG53 S255G:
                                        (SEQ ID NO: 77)
tgcagaagattctgtcagagggaccaccccag Reverse primer of rat MG53 5255G:
                                        (SEQ ID NO: 78)
tctagccttgctgggggtggtccctctgacaga
```

(iii) the forward and reverse primers of rat MG53 S255L, which represents an MG53 mutant in which serine at position 255 of rat wild-type MG53 (i.e. SEQ ID NO: 3) is mutated into leucine.

```
Forward primer of rat MG53 S255L:
                                        (SEQ ID NO: 79)
tgcagaagattctgtcagagttaccaccccag Reverse primer of rat MG53 S255L:
                                        (SEQ ID NO: 80)
tctagccttgctgggggtggtaactctgacaga
```

(iv) the forward and reverse primers of rat MG53 S255W, which represents an MG53 mutant in which serine at position 255 of rat wild-type MG53 (i.e. SEQ ID NO: 3) is mutated into tryptophan.

```
Forward primer of rat MG53 S255W:
                                        (SEQ ID NO: 81)
tgcagaagattctgtcagagtggccaccccag Reverse primer of rat MG53 S255W:
                                        (SEQ ID NO: 82)
tctagccttgctgggggtggccactctgacaga
```

(v) the forward and reverse primers of rat MG53 S255Q, which represents an MG53 mutant in which serine at position 255 of rat wild-type MG53 (i.e. SEQ ID NO: 3) is mutated into glutamine.

```
Forward primer of rat MG53 S255Q:
                                        (SEQ ID NO: 83)
tgcagaagattctgtcagagcaaccaccccag Reverse primer of rat MG53 S255Q:
                                        (SEQ ID NO: 84)
tctagccttgctgggggtggttgctctgacaga
```

(vi) the forward and reverse primers of rat MG53 S255Y, which represents an MG53 mutant in which serine at position 255 of rat wild-type MG53 (i.e. SEQ ID NO: 3) is mutated into tyrosine.

```
Forward primer of rat MG53 S255Y:
                                        (SEQ ID NO: 85)
tgcagaagattctgtcagagtatccaccccag Reverse primer of rat MG53 S255Y:
                                        (SEQ ID NO: 86)
tctagccttgctgggggtggatactctgacaga
```

(vii) the forward and reverse primers of rat MG53 S255D, which represents an MG53 mutant in which serine at position 255 of rat wild-type MG53 (i.e. SEQ ID NO: 3) is mutated into aspartic acid.

```
Forward primer of rat MG53 S255D:
                                        (SEQ ID NO: 87)
tgcagaagattctgtcagaggatccaccccag Reverse primer of rat MG53 S255D:
                                        (SEQ ID NO: 88)
tctagccttgctgggggtggatcctctgacaga
```

(viii) the forward and reverse primers of rat MG53 S255R, which represents an MG53 mutant in which serine at position 255 of rat wild-type MG53 (i.e. SEQ ID NO: 3) is mutated into arginine.

```
Forward primer of rat MG53 S255R:
                                        (SEQ ID NO: 89)
tgcagaagattctgtcagagcgaccaccccag Reverse primer of rat MG53 S255R:
                                        (SEQ ID NO: 90)
tctagccttgctgggggtggtcgctctgacaga
```

4. Preparation of Monkey MG53 Mutants

Monkey MG53 S255A, S255G, S255L, S255W, S255Q, S255Y, S255D, and S255R mutants were prepared according to the method for preparing human MG53 S255A mutant. Except for the primers, all of the other steps are the same as the steps for preparing human MG53 S255A mutant. The primers of each mutant are as follows:

(i) the forward and reverse primers of monkey MG53 S255A, which represents an MG53 mutant in which serine at position 255 of monkey wild-type MG53 (i.e. SEQ ID NO: 4) is mutated into alanine.

```
Forward primer of monkey MG53 S255A:
                                     (SEQ ID NO: 91)
aagatcctggcagaggctcccccacccgcccgtctg Reverse primer of monkey MG53 S255A:
                                     (SEQ ID NO: 92)
cagacgggcgggtgggggagcctctgccaggatctt
```

(ii) the forward and reverse primers of monkey MG53 S255G, which represents an MG53 mutant in which serine at position 255 of monkey wild-type MG53 (i.e. SEQ ID NO: 4) is mutated into glycine.

```
Forward primer of monkey MG53 S255G:
                                     (SEQ ID NO: 93)
aagatcctggcagagggtcccccacccgcccgtctgg Reverse primer of monkey MG53 S255G:
                                     (SEQ ID NO: 94)
ccagacgggcgggtgggggaccctctgccaggatctt
```

(iii) the forward and reverse primers of monkey MG53 S255L, which represents an MG53 mutant in which serine at position 255 of monkey wild-type MG53 (i.e. SEQ ID NO: 4) is mutated into leucine.

```
Forward primer of monkey MG53 S255L:
                                     (SEQ ID NO: 95)
agatcctggcagagttaccccacccgcccgtctgga Reverse primer of monkey MG53 S255L:
                                     (SEQ ID NO: 96)
tccagacgggcgggtgggggtaactctgccaggatct
```

(iv) the forward and reverse primers of monkey MG53 S255W, which represents an MG53 mutant in which serine at position 255 of monkey wild-type MG53 (i.e. SEQ ID NO: 4) is mutated into tryptophan.

```
Forward primer of monkey MG53 S255W:
                                     (SEQ ID NO: 97)
agatcctggcagagtggccccacccgcccgtctgga Reverse primer of monkey MG53 S255W:
                                     (SEQ ID NO: 98)
tccagacgggcgggtgggggccactctgccaggatct
```

(v) the forward and reverse primers of monkey MG53 S255Q, which represents an MG53 mutant in which serine at position 255 of monkey wild-type MG53 (i.e. SEQ ID NO: 4) is mutated into glutamine.

```
Forward primer of monkey MG53 S255Q:
                                     (SEQ ID NO: 99)
aagatcctggcagagcaaccccacccgcccgtctgga Reverse primer of monkey MG53 S255Q:
                                     (SEQ ID NO: 100)
tccagacgggcgggtgggggttgctctgccaggatctt
```

(vi) the forward and reverse primers of monkey MG53 S255Y, which represents an MG53 mutant in which serine at position 255 of monkey wild-type MG53 (i.e. SEQ ID NO: 4) is mutated into tyrosine.

```
Forward primer of monkey MG53 S255Y:
                                     (SEQ ID NO: 101)
agatcctggcagagtatccccacccgcccgtctgg Reverse primer of monkey MG53 S255Y:
                                     (SEQ ID NO: 102)
ccagacgggcgggtgggggatactctgccaggatct
```

(vii) the forward and reverse primers of monkey MG53 S255D, which represents an MG53 mutant in which serine at position 255 of monkey wild-type MG53 (i.e. SEQ ID NO: 4) is mutated into aspartic acid.

```
Forward primer of monkey MG53 S255D:
                                     (SEQ ID NO: 103)
aagatcctggcagaggatcccccacccgcccgtctgg Reverse primer of monkey MG53 S255D:
                                     (SEQ ID NO: 104)
ccagacgggcgggtgggggatcctctgccaggatctt
```

(viii) the forward and reverse primers of monkey MG53 S255R, which represents an MG53 mutant in which serine at position 255 of monkey wild-type MG53 (i.e. SEQ ID NO: 4) is mutated into arginine.

```
Forward primer of monkey MG53 S255R:
                                     (SEQ ID NO: 105)
aagatcctggcagagcgtcccccacccgcccgtctgg Reverse primer of monkey MG53 S255R:
                                     (SEQ ID NO: 106)
ccagacgggcgggtgggggacgctctgccaggatctt
```

5. Preparation of Swine MG53 Mutants

Swine MG53 S255A, S255G, S255L, S255W, S255Q, S255Y, S255D, and S255R mutants were prepared according to the method for preparing human MG53 S255A mutant. Except for the primers, all of the other steps are the same as the steps for preparing human MG53 S255A mutant. The primers of each mutant are as follows:

(i) the forward and reverse primers of swine MG53 S255A, which represents an MG53 mutant in which serine at position 255 of swine wild-type MG53 (i.e. SEQ ID NO: 5) is mutated into alanine.

```
Forward primer of swine MG53 S255A:
                                     (SEQ ID NO: 107)
aagatcctggcagaggcgcccccacctgcccgcctg Reverse primer of swine MG53 S255A:
                                     (SEQ ID NO: 108)
caggcgggcaggtgggggcgcctctgccaggatctt
```

(ii) the forward and reverse primers of swine MG53 S255G, which represents an MG53 mutant in which serine at position 255 of swine wild-type MG53 (i.e. SEQ ID NO: 5) is mutated into glycine.

```
Forward primer of swine MG53 S255G:
                                  (SEQ ID NO: 109)
aagatcctggcagagggggccccacctgcccgcctgg Reverse primer of swine MG53 S255G:
                                  (SEQ ID NO: 110)
ccaggcgggcaggtgggggcccctctgccaggatctt
```

(iii) the forward and reverse primers of swine MG53 S255L, which represents an MG53 mutant in which serine at position 255 of swine wild-type MG53 (i.e. SEQ ID NO: 5) is mutated into leucine.

```
Forward primer of swine MG53 S255L:
                                  (SEQ ID NO: 111)
agatcctggcagagttgccccacctgcccgcctgg Reverse primer of swine MG53 S255L:
                                  (SEQ ID NO: 112)
ccaggcgggcaggtgggggcaactctgccaggatct
```

(iv) the forward and reverse primers of swine MG53 S255W, which represents an MG53 mutant in which serine at position 255 of swine wild-type MG53 (i.e. SEQ ID NO: 5) is mutated into tryptophan.

```
Forward primer of swine MG53 S255W:
                                  (SEQ ID NO: 113)
agatcctggcagagtggccccacctgcccgcctgg Reverse primer of swine MG53 S255W:
                                  (SEQ ID NO: 114)
ccaggcgggcaggtgggggccactctgccaggatct
```

(v) the forward and reverse primers of swine MG53 S255Q, which represents an MG53 mutant in which serine at position 255 of swine wild-type MG53 (i.e. SEQ ID NO: 5) is mutated into glutamine.

```
Forward primer of swine MG53 S255Q:
                                  (SEQ ID NO: 115)
aagatcctggcagagcagccccacctgcccgcctgg Reverse primer of swine MG53 S255Q:
                                  (SEQ ID NO: 116)
ccaggcgggcaggtgggggctgctctgccaggatctt
```

(vi) the forward and reverse primers of swine MG53 S255Y, which represents an MG53 mutant in which serine at position 255 of swine wild-type MG53 (i.e. SEQ ID NO: 5) is mutated into tyrosine.

```
Forward primer of swine MG53 S255Y:
                                  (SEQ ID NO: 117)
agatcctggcagagtatccccacctgcccgcctgga Reverse primer of swine MG53 S255Y:
                                  (SEQ ID NO: 118)
tccaggcgggcaggtgggggatactctgccaggatct
```

(vii) the forward and reverse primers of swine MG53 S255D, which represents an MG53 mutant in which serine at position 255 of swine wild-type MG53 (i.e. SEQ ID NO: 5) is mutated into aspartic acid.

```
Forward primer of swine MG53 S255D:
                                  (SEQ ID NO: 119)
aagatcctggcagaggatccccacctgcccgcctgga Reverse primer of swine MG53 S255D:
                                  (SEQ ID NO: 120)
tccaggcgggcaggtgggggatcctctgccaggatctt
```

(viii) the forward and reverse primers of swine MG53 S255R, which represents an MG53 mutant in which serine at position 255 of swine wild-type MG53 (i.e. SEQ ID NO: 5) is mutated into arginine.

```
Forward primer of swine MG53 S255R:
                                  (SEQ ID NO: 121)
aagatcctggcagagcggccccacctgcccgcctgg Reverse primer of swine MG53 S255R:
                                  (SEQ ID NO: 122)
ccaggcgggcaggtgggggccgctctgccaggatctt
```

6. Preparation of Dog MG53 Mutants

Dog MG53 S255A, S255G, S255L, S255W, S255Q, S255Y, S255D, and S255R mutants were prepared according to the method for preparing human MG53 S255A mutant. Except for the primers, all of the other steps are the same as the steps for preparing human MG53 S255A mutant. The primers of each mutant are as follows:

(i) the forward and reverse primers of dog MG53 S255A, which represents an MG53 mutant in which serine at position 255 of dog wild-type MG53 (i.e. SEQ ID NO: 6) is mutated into alanine.

```
Forward primer of dog MG53 S255A:
                                  (SEQ ID NO: 123)
aagatcctggcagaagcaccaccgcctgcccgtttg Reverse primer of dog MG53 S255A:
                                  (SEQ ID NO: 124)
caaacgggcaggcggtggtgcttctgccaggatctt
```

(ii) the forward and reverse primers of dog MG53 S255G, which represents an MG53 mutant in which serine at position 255 of dog wild-type MG53 (i.e. SEQ ID NO: 6) is mutated into glycine.

```
Forward primer of dog MG53 S255G:
                                  (SEQ ID NO: 125)
aagatcctggcagaaggaccaccgcctgcccgtttgg Reverse primer of dog MG53 S255G:
                                  (SEQ ID NO: 126)
ccaaacgggcaggcggtggtccttctgccaggatctt
```

(iii) the forward and reverse primers of dog MG53 S255L, which represents an MG53 mutant in which serine at position 255 of dog wild-type MG53 (i.e. SEQ ID NO: 6) is mutated into leucine.

```
Forward primer of dog MG53 S255L:
                                    (SEQ ID NO: 127)
agatcctggcagaattaccaccgcctgcccgtttgg Reverse primer of dog MG53 S255L:
                                    (SEQ ID NO: 128)
ccaaacgggcaggcggtggtaattctgccaggatct
```

(iv) the forward and reverse primers of dog MG53 S255W, which represents an MG53 mutant in which serine at position 255 of dog wild-type MG53 (i.e. SEQ ID NO: 6) is mutated into tryptophan.

```
Forward primer of dog MG53 S255W:
                                    (SEQ ID NO: 129)
agatcctggcagaatggccaccgcctgcccgtttgga Reverse primer of dog MG53 S255W:
                                    (SEQ ID NO: 130)
tccaaacgggcaggcggtggccattctgccaggatct
```

(v) the forward and reverse primers of dog MG53 S255Q, which represents an MG53 mutant in which serine at position 255 of dog wild-type MG53 (i.e. SEQ ID NO: 6) is mutated into glutamine.

```
Forward primer of dog MG53 S255Q:
                                    (SEQ ID NO: 131)
aagatcctggcagaacaaccaccgcctgcccgtttgg Reverse primer of dog MG53 S255Q:
                                    (SEQ ID NO: 132)
ccaaacgggcaggcggtggttgttctgccaggatctt
```

(vi) the forward and reverse primers of dog MG53 S255Y, which represents an MG53 mutant in which serine at position 255 of dog wild-type MG53 (i.e. SEQ ID NO: 6) is mutated into tyrosine.

```
Forward primer of dog MG53 S255Y:
                                    (SEQ ID NO: 133)
agatcctggcagaatatccaccgcctgcccgtttgga Reverse primer of dog MG53 S255Y:
                                    (SEQ ID NO: 134)
tccaaacgggcaggcggtggatattctgccaggatct
```

(vii) the forward and reverse primers of dog MG53 S255D, which represents an MG53 mutant in which serine at position 255 of dog wild-type MG53 (i.e. SEQ ID NO: 6) is mutated into aspartic acid.

```
Forward primer of dog MG53 S255D:
                                    (SEQ ID NO: 135)
aagatcctggcagaagatccaccgcctgcccgtttgga Reverse primer of dog MG53 S255D:
                                    (SEQ ID NO: 136)
tccaaacgggcaggcggtggatcttctgccaggatctt
```

(viii) the forward and reverse primers of dog MG53 S255R, which represents an MG53 mutant in which serine at position 255 of dog wild-type MG53 (i.e. SEQ ID NO: 6) is mutated into arginine.

```
Forward primer of dog MG53 S255R:
                                    (SEQ ID NO: 137)
aagatcctggcagaacgaccaccgcctgcccgtttgg Reverse primer of dog MG53 S255R:
                                    (SEQ ID NO: 138)
ccaaacgggcaggcggtggtcgttctgccaggatctt
```

MG53 mutants of various species with serine deletion and/or mutation at each serine position may be prepared according to the method for preparing human MG53 S255A mutant. Except for the primers, all of the other steps are the same as the steps for preparing human MG53 S255A mutant. A person skilled in the art may design the primers of each mutant by conventional technical means in the art.

Example 2: Impact of Mouse MG53 S255A Mutant on the Cell Membrane Repair Function and Cardioprotective Function of Mouse Wild-Type MG53

Figure 14:
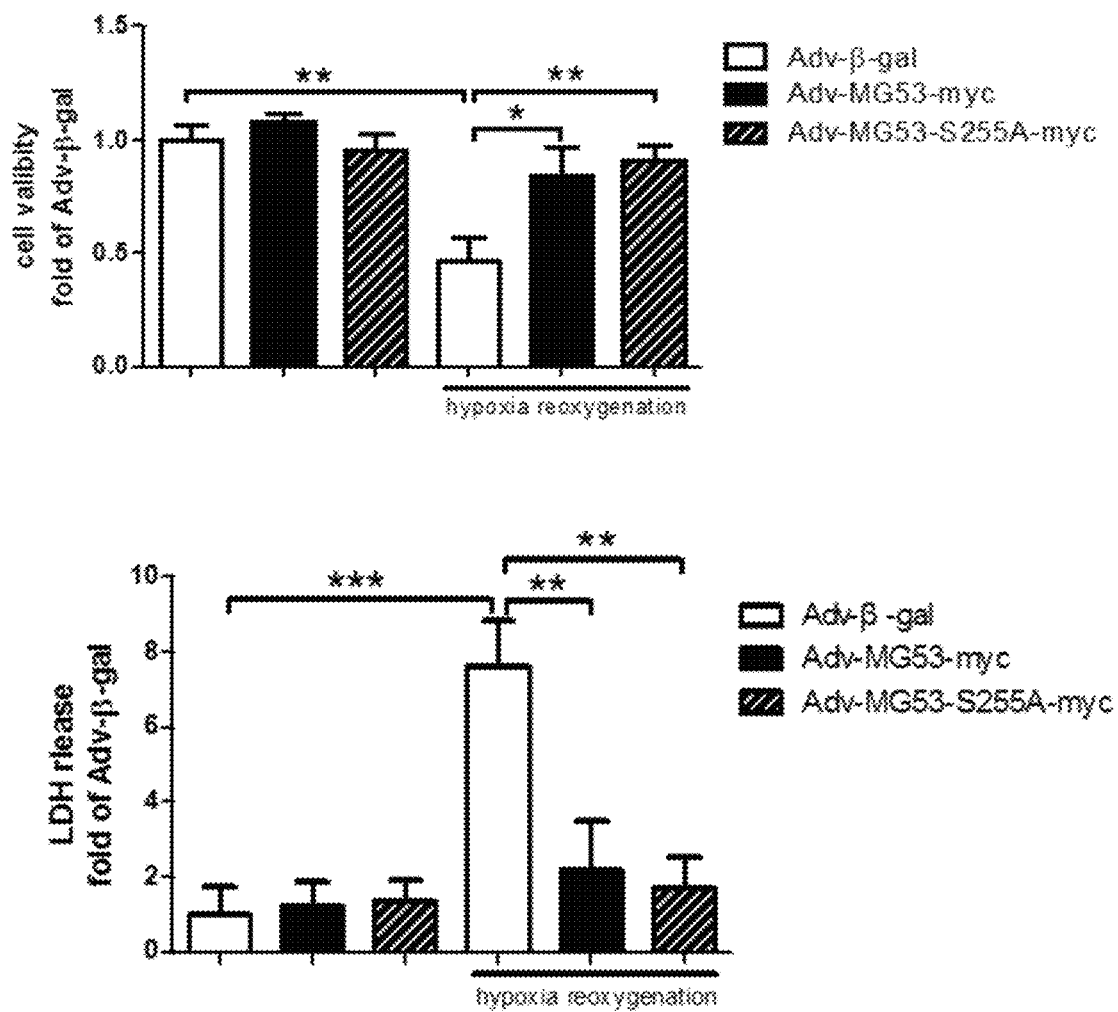
FIG. 14 illustrates the amounts of intracellular ATP and LDH release after adenovirus is used to overexpress mouse wild-type MG53 and mouse MG53 S255A mutant in primarily cultured cardiomyocytes of neonatal rats. The upper panel shows the detected amount of intracellular ATP after hypoxia and reoxygenation treatment when adenovirus is used to overexpress mouse wild-type MG53 and mouse MG53 S255A mutant in primarily cultured cardiomyocytes of neonatal rats, wherein Adv-β-gal represents a control virus expressing galactosidase, but not expressing mouse wild-type MG53 or mouse MG53 S255A mutant; Adv-MG53-myc represents adenovirus expressing mouse wild-type MG53; Adv-MG53-S255A-myc represents adenovirus expressing mouse MG53 S255A mutant (n=7, *p<0.05, p<0.01). The lower panel shows the detected amount of LDH release after hypoxia and reoxygenation treatment when adenovirus is used to overexpress mouse wild-type MG53 and mouse MG53 S255A mutant in primarily cultured cardiomyocytes of neonatal rats, wherein Adv-β-gal represents a control virus expressing galactosidase, but not expressing mouse wild-type MG53 or mouse MG53 S255A mutant; Adv-MG53-myc represents adenovirus expressing mouse wild-type MG53; Adv-MG53-S255A-myc represents adenovirus expressing mouse MG53 S255A mutant (n=7, p<0.01, ***p<0.005).

In order to evaluate the impact of mouse MG53 S255A mutant (its amino acid sequence is set forth in SEQ ID NO: 8) on the cell membrane repair function and cardioprotective function of mouse wild-type MG53, the inventors overexpressed mouse wild-type MG53 and mouse MG53 mutant using adenovirus in neonatal rat ventricular myocytes (NRVMs) that were primarily cultured, and detected the survival rate of cells. The results are shown in FIG. 14, which indicates that hypoxia/reoxygenation-simulating ischemia-reperfusion injury result in the massive release of lactate dehydrogenase (LDH) and decreased intracellular ATP in NRVMs, the over-expression of mouse wild-type MG53 and mouse MG53 S255A mutant can similarly inhibit LDH release and ATP reduction. This suggests that mouse wild-type MG53 has a protective effect on ischemia-reperfusion induced apoptosis and necrosis, while the mouse MG53 S255A mutant does not affect the cell membrane repair function and cardioprotective function of the mouse wild-type MG53, i.e. the phosphorylation of mouse MG53 S255 position does not regulate the cell membrane repair function and cardioprotective function of MG53.

Mouse MG53 S255A Mutation does not Affect MG53's Activation on the RISK Signaling Pathway.

Figure 15:
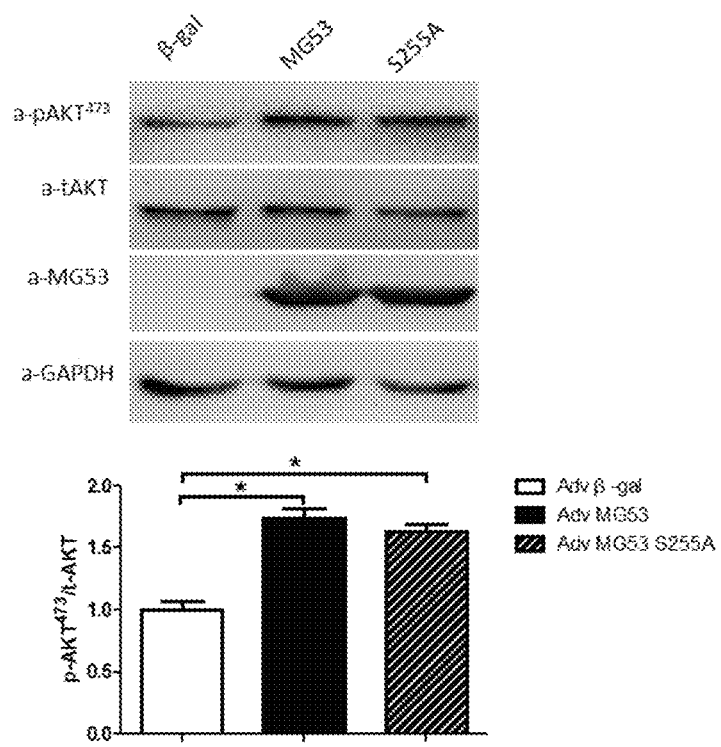
FIG. 15 illustrates that mouse MG53 S255A mutation does not affect the activation of AKT by mouse wild-type MG53. The upper panel shows the amount of intracellular p-AKT$^{473}$ detected by Western Blot when adenovirus is used to overexpress mouse wild-type MG53 and mouse MG53 S255A mutant in primarily cultured cardiomyocytes of neonatal rats, wherein β-gal represents control adenovirus expressing galactosidase, but not expressing mouse wild-type MG53 or mouse MG53 S255A mutant; MG53 represents adenovirus expressing mouse wild-type MG53; S255A represents adenovirus expressing mouse MG53 S255A mutant. The lower panel is a statistic diagram of the upper panel, wherein Adv β-gal represents control adenovirus expressing galactosidase, but not expressing mouse wild-type MG53 or MG53 S255A mutant; Adv MG53 represents adenovirus expressing mouse wild-type MG53; Adv MG53 S255A represents adenovirus expressing mouse MG53 S255A mutant (n=5, * p<0.05).

The mechanism of MG53's cardioprotective function is as follows: MG53 is an essential component in the RISK signaling pathway of cardiac protection, and mediates the interaction between caveolin-3 and p85-PI3K proteins to activate the RISK signaling pathway, for example, an important downstream signaling molecule AKT (see Zhang Y. et al., *Cardiovascular Research* 91, 108-115 (2011)). Therefore, the inventors further studied the mechanism by which the mouse MG53 S255A mutation does not affect MG53's cardioprotective function to identify whether it is related to the fact that mouse MG53 S255A mutant and mouse wild-type MG53 can similarly activate the RISK signaling pathway. The experimental results are shown in FIG. 15, which indicates that the over-expression of mouse wild-type MG53 in NRVMs enhances the phosphorylation of serine at position 473 of AKT, which is a downstream signaling molecule of the RISK signaling pathway, i.e. can activate AKT. The mouse MG53 S255A mutant and mouse wild-type MG53 can similarly enhance the phosphorylation of serine at position 473 of AKT, i.e. can activate AKT. This suggests that the mouse MG53 S255A mutant does not affect mouse wild-type MG53's activation of the RISK signaling pathway, i.e. the regulation on the phosphorylation of mouse MG53 S255 does not affect the RISK signaling cardioprotective pathway.

Example 3: Impact of Human or Mouse MG53 S255A Mutant on E3 Ubiquitin Ligase Activity of Wild-Type MG53

Figure 19:
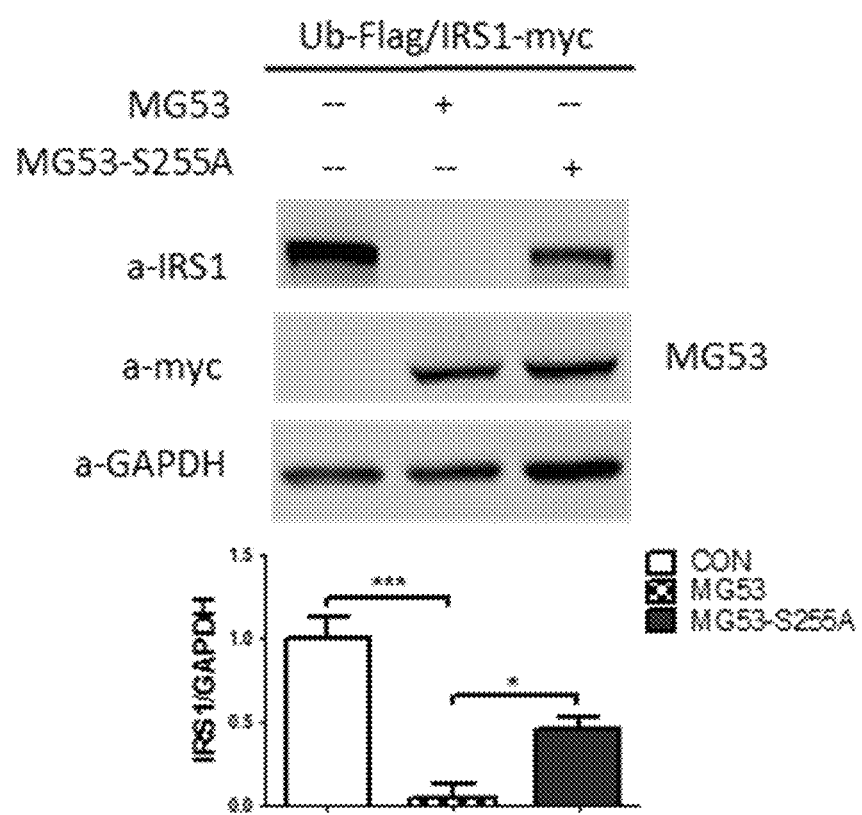
FIG. 19 illustrates the effect of mouse MG53 S255A mutant on the amount of protein IRS1. The upper panel shows the content of protein IRS1 detected by Western Blot in plasmids overexpressing IRS1, Ub, MG53, or MG53 S255A mutant in HEK293T cell line, wherein Ub represents ubiquitin, MG53 represents mouse wild-type MG53, and MG53-S255A represents mouse MG53 S255A mutant. The lower panel is a statistic diagram of the upper panel, wherein CON represents an empty vector plasmid control without expression of mouse wild-type MG53 and mouse MG53 S255A mutant, MG53-S255A represents a vector plasmid expressing mouse MG53 S255A mutant (n=3, *p<0.05; ***p<0.005).

The repression of insulin signaling pathway induced by high-expression of MG53 is one of the important mechanisms for the development of insulin resistance and metabolic syndrome, and it is also one of the important functions of MG53. First, the inventors constructed the expression plasmid of serine mutation of mouse wild-type MG53—mouse MG53 S255A (its amino acid sequence is set forth in SEQ ID NO: 8). In addition, the inventors also constructed the expression plasmids of IRS1, ubiquitin, and mouse wild-type MG53. Second, the inventors' previous study suggests that, MG53 is an E3 ubiquitin ligase of insulin substrate IRS1, and mediates proteasomal pathway degradation of proteins (Song, R. et al., Nature 494, 375-379, (2013)). Therefore, the inventors co-transfected HEK293T cell line with the expression plasmids of IRS1, ubiquitin, and the plasmid of mouse wild-type MG53 or mouse MG53 S255A mutant, and evaluated the impact of mouse MG53 S255A mutation on MG53 functions through the changes in IRS1 protein contents. The experimental results are shown in FIG. 19, which suggests that mouse wild-type MG53 can significantly reduce IRS1 expression, while mouse MG53 S255A mutant can significantly inhibit MG53-mediated IRS1 protein reduction. This suggests that, in the co-expression system of HEK293T cell line, the mouse wild-type MG53 can exert normal E3 ubiquitin ligase activity, and mediate the ubiquitin degradation of IRS1. This also suggests that the detected mouse MG53 S255A mutant inhibited the E3 ubiquitin ligase activity of MG53, i.e. the phosphorylation status of MG53 S255 position can regulate the E3 ubiquitin ligase activity of MG53.

Human or Mouse MG53 S255A Mutant Inhibits MG53-Mediated Substrate Degradation

Figure 17:
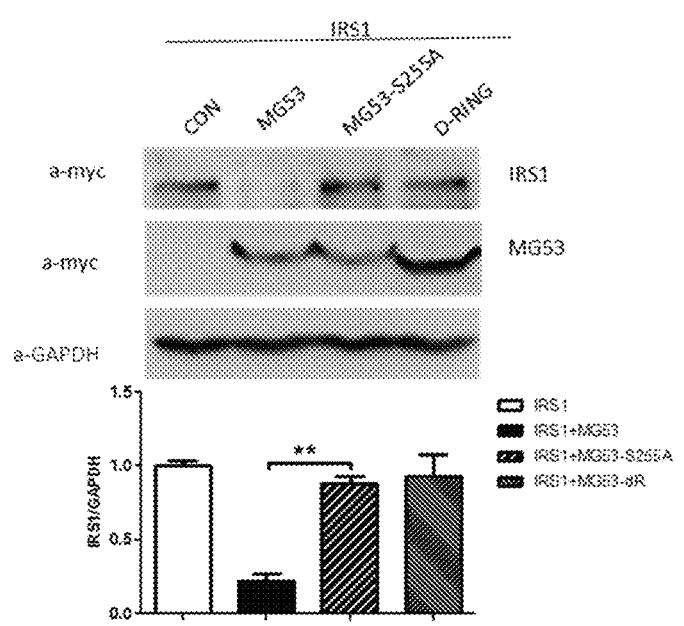
FIG. 17 illustrates that human MG53 S255A mutant inhibits MG53-mediated substrate degradation. The upper panel shows IRS1 protein content detected by Western Blot in plasmids overexpressing IRS1, human wild-type MG53, human MG53 S255A mutant, or human MG53-D-RING truncated mutant in HEK293T cell line, wherein CON represents an empty vector plasmid control without expression of human wild-type MG53, human MG53 S255A mutant, and human MG53-D-RING truncated mutant; MG53 represents a vector plasmid expressing human wild-type MG53; MG53-dR represents a vector plasmid expressing human MG53-D-RING truncated mutant. The lower panel is a statistic diagram of the upper panel (n=5, **p<0.01).

MG53 is an E3 ubiquitin ligase with a RING domain, which is associated with E2 ubiquitin conjugating enzyme to mediate the ubiquitination of substrate and further proteasomal degradation. Therefore, the MG53-D-RING truncated mutant, which is without the RING domain, loses the E3 ubiquitin ligase activity of MG53. Further, in order to quantitatively evaluate the impact of human MG53 S255A mutant (its amino acid sequence is set forth in SEQ ID NO: 7) and mouse MG53 S255A mutant (its amino acid sequence is set forth in SEQ ID NO: 8) on the E3 ubiquitin ligase activity of human or mouse wild-type MG53, the inventors, by taking human or mouse MG53-D-RING as a positive control, co-expressed human or mouse wild-type MG53, MG53 S255A mutant, or MG53-D-RING truncated mutant, and the substrate IRS1 of MG53 or insulin receptor IR in human embryonic kidney epithelial cell line HEK293T, and detected the impact of different mutations on MG53-mediated substrate degradation. The results are shown in FIG. 16 (mouse) and FIG. 17 (human), which indicate that human or mouse wild-type MG53 can significantly mediate IRS1 degradation, human or mouse MG53-D-RING truncated mutant can hardly mediate IRS1 degradation, while mouse MG53 S255A mutant can only mediate about 40% degradation of IRS1, and human MG53 S255A mutant can only mediate about 10% degradation of IRS1. Mouse wild-type MG53 can mediate about 50% degradation of IRβ, mouse MG53-D-RING truncated mutant and mouse MG53 S255A mutant can hardly mediate IRβ degradation. In addition, in HEK293T co-expression system, mouse wild-type MG53 can mediate the degradation of precursor protein of IRβ, while mouse MG53-D-RING truncated mutant and mouse MG53 S255A mutant almost completely inhibited MG53-mediated degradation. This study suggests that human or mouse MG53-D-RING truncated mutant significantly inhibit the E3 ubiquitin ligase activity of MG53, while human or mouse MG53 S255A mutant inhibits about at least 50% E3 ubiquitin ligase activity of MG53.

Figure 18:
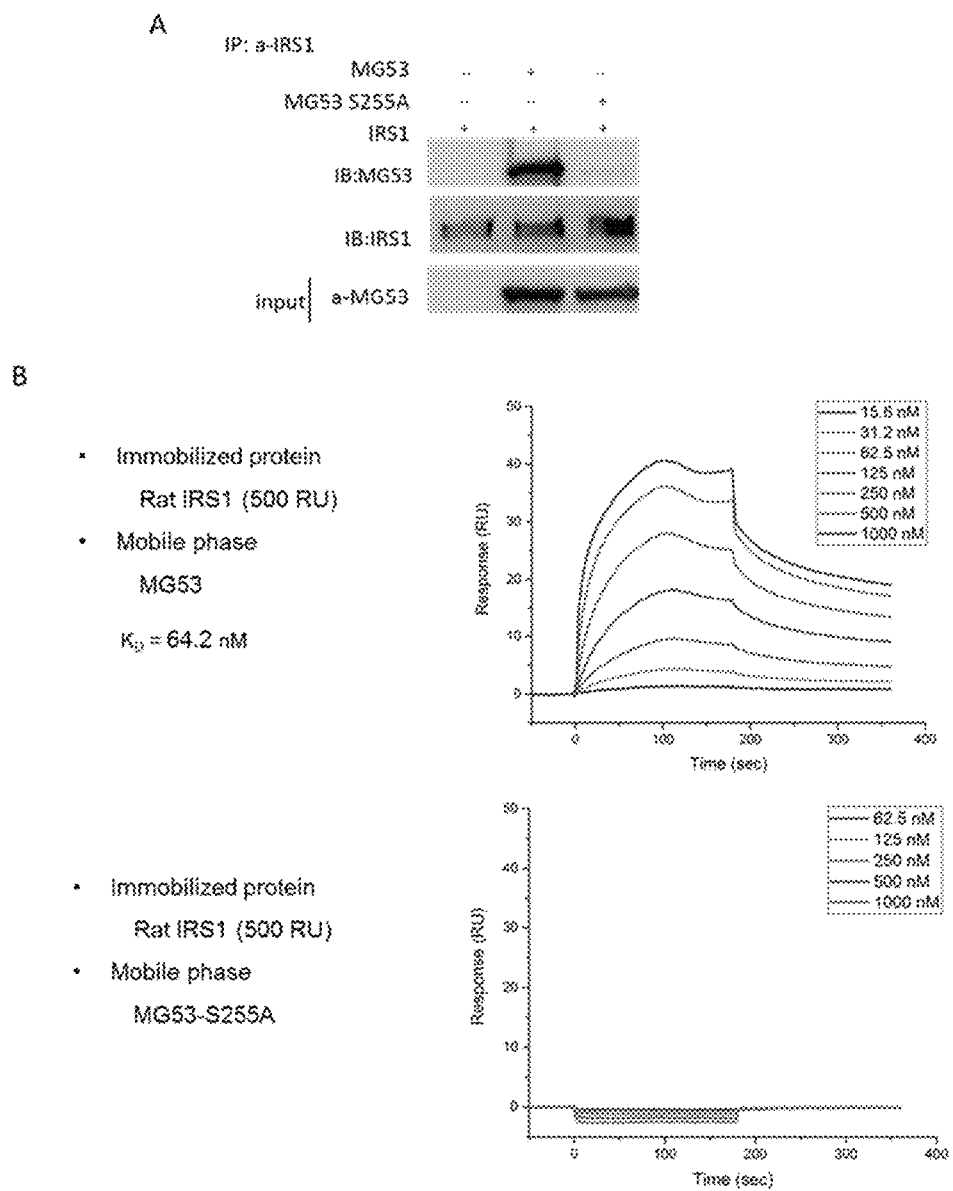
FIG. 18 illustrates that mouse MG53 S255A mutant inhibits the binding of MG53 to substrate IRS1.

Mouse MG53 S255A Mutant Inhibits the Binding of MG53 to the Substrate IRS1 Protein In order to study whether mouse MG53 S255A mutant (its amino acid sequence is set forth in SEQ ID NO: 8) may affect the recognition and binding of MG53 to the substrate IRS1 protein, the inventors, in one aspect, detected the binding intensity of substrate IRS1 and mouse wild-type MG53 or mouse MG53 S255A mutant under active status in ex vivo HEK293T cell line through co-immunoprecipitation, in another aspect, detected the direct binding intensity of purified protein IRS1 and mouse wild-type MG53 or mouse MG53 S255A mutant through surface plasmon resonance (SPR) test. The experimental results are shown in FIG. 18. FIG. 18A shows that IRS1 can physically bind to mouse wild-type MG53, while the same amount of IRS1 can only bind to extremely small amount of mouse MG53 S255A mutant; FIG. 18B shows that mouse wild-type MG53 protein can bind to IRS1 protein very well, with a KD of 64.2 nM, while mouse MG53 S255A mutant cannot bind to IRS1 protein. In light of the above, mouse MG53 S255A mutation inhibited the recognition and binding of MG53 to the substrate IRS1 protein, so as to inhibit the E3 ubiquitin ligase activity of MG53.

Example 4: The In Vivo Activity of Human MG53 S255A Mutant

In order to validate whether human MG53 S255A mutant (its amino acid sequence is set forth in SEQ ID NO: 7) in vivo may still avoid or reduce metabolic side effects caused by wild-type MG53, while retaining cell membrane repair function and cardioprotective function, the inventors introduce human MG53 S255A mutant and human wild-type MG53 into the body of rats, respectively, to further analyze the in vivo activity of human MG53 S255A mutant. First, the inventors prepare human MG53 S255A mutant according to Example 1 of the present application. Second, 15 male Sprague-Dawley (SD) rats (about 250 g/rat, provided by Beijing Vital River Laboratory Animal Technology Co., Ltd.) are selected and grouped into three groups, i.e. test group, positive control group, and negative control group, 5 rats/group. The rats are anaesthetized via 30 mg/kg pentobartial sodium (intraperitoneal injection), and then thoracotomy is performed in the left third rib to expose the heart. Then, human MG53 S255A mutant protein (6 mg/kg, iv) is intravenously injected into the hearts of rats in the test group, human wild-type MG53 protein (its amino acid sequence is set forth in SEQ ID NO: 1) (6 mg/kg, iv) is intravenously injected into the hearts of rats in the positive control group, and bovine serum albumin (BSA) (6 mg/kg, iv) is intravenously injected into the hearts of rats in the negative control group. The ligation of the left anterior descending arteries of the rats in each group are conducted at 5 minutes after the intravenous injections of the proteins above, and lasted for 45 minutes. Before the ending of the ligation, the rats of each group are again intravenously injected with the corresponding human MG53 S255A mutant protein, human wild-type MG53 protein and BSA (6 mg/kg, iv), respectively, and then the coronary arteries are released. After a 24 hour reperfusion period, survival rates are compared between the test group, positive control group, and negative control group. Insulin is used to stimulate the rats in each group, and the rats are then sacrificed to compare the infarct size, serum LDH concentration, and TUNEL staining of myocardial sections of the rats in the test group, positive control group, and negative control group. Taken together, these indicators measure the level of cardiac injury of rats in each group. If the infarct size of the rats in the test group is significantly smaller than the infarct size of the rats in the negative control group, or the rats in test group demonstrate significantly inhibited LDH release compared to the rats in negative control group, or the TUNEL staining results of the myocardial sections of the rats in test group indicates decreased cell death compared to that of the rats in negative control group, then it suggests that human MG53 S255A mutant does not affect the cell membrane repair function and cardioprotective function of human wild-type MG53, and can be used for treating heart diseases, such as myocardial infarction, cardiac ischemia/reperfusion injury, etc. At last, p-AKT/t-AKT changes in each tissue (e.g. myocardium, skeletal muscle, liver, etc.) of the rats in test group, positive control group and negative control group are compared to evaluate the insulin responsiveness of each tissue of the rats in test group, positive control group and negative control group. If the ratio of p-AKT/t-AKT in the tissues of the rats in positive control group is decreased, then it suggests that human wild-type MG53 protein may induce the reduction of insulin sensitivity; if the ratio of p-AKT/t-AKT in the tissues of the rats in negative control group is normal, then it suggests that BSA has no effect on insulin sensitivity; if the ratio of p-AKT/t-AKT in the tissues of the rats in test group is higher than positive control group, then it suggests that human MG53 S255A mutant may eliminate or weaken the reduction of insulin sensitivity induced by human wild-type MG53 protein.

Example 5: Impact of Human MG53 S305/306/307A Mutant on E3 Ubiquitin Ligase Activity of Wild-Type MG53

Figure 29:
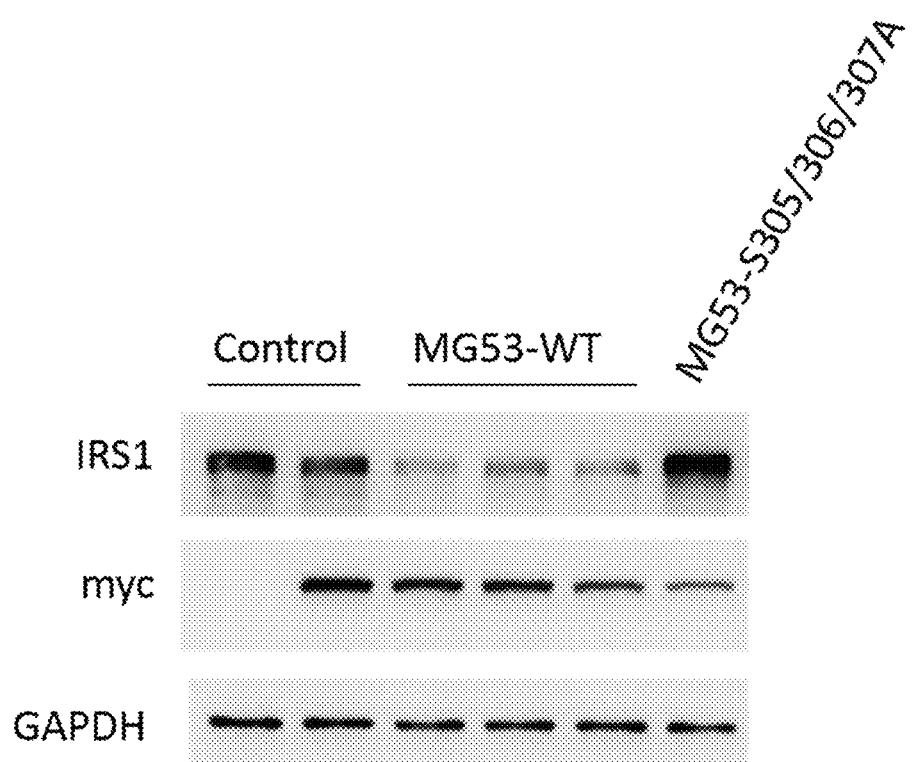
FIG. 29 illustrates the effect of human MG53 S305/306/307A mutant on the amount of protein IRS1. The Figure shows the content of protein IRS1 detected by Western Blot in plasmids overexpressing IRS1, MG53, or MG53 S305/306/307A mutant in HEK293T cell line, wherein MG53-WT represents human wild-type MG53, and MG53-S305/306/307A represents human MG53 S305/306/307A mutant.

The repression of insulin signaling pathway induced by high-expression of MG53 is one of the important mechanisms for the development of insulin resistance and metabolic syndrome, and it is also one of the important functions of MG53. First, the inventors constructed the expression plasmid of serine mutation of human wild-type MG53—human MG53 S305/306/307A (i.e. three serine residues at positions 305, 306 and 307 of SEQ ID NO: 1 were replaced with three alanines). In addition, the inventors also constructed the expression plasmids of IRS1 and human wild-type MG53. Second, the inventors' previous study suggests that, MG53 is an E3 ubiquitin ligase of insulin substrate IRS1, and mediates proteasomal pathway degradation of proteins (Song, R. et al., Nature 494, 375-379, (2013)). Therefore, the inventors co-transfected HEK293T cell line with the expression plasmids of IRS1 and the plasmid of human wild-type MG53 or human MG53 S305/306/307A mutant, and evaluated the impact of human MG53 S305/306/307A mutation on MG53 functions through the changes in IRS1 protein contents. The experimental results are shown in FIG. 29, which suggests that human wild-type MG53 can significantly reduce IRS1 expression, while human MG53 S305/306/307A mutant can significantly inhibit MG53-mediated IRS1 protein reduction. This suggests that, in the co-expression system of HEK293T cell line, the human wild-type MG53 can exert normal E3 ubiquitin ligase activity, and mediate the ubiquitin degradation of IRS1. This also suggests that the detected human MG53 S305/306/307A mutant inhibited the E3 ubiquitin ligase activity of MG53, i.e. the phosphorylation status of MG53 S305/306/307 positions can regulate the E3 ubiquitin ligase activity of MG53.

In summary, if at least one serine (especially serine at position 255) within the MG53 coiled-coil-SPRY region is deleted or mutated into any other non-serine or non-threonine (e.g. alanine) amino acid, the resulting MG53 mutant may avoid or reduce metabolic side effects, such as insulin resistance, caused by wild-type MG53, while still retaining cell repair function and/or cardioprotective function.

Although the present invention is disclosed and described by introducing specific embodiments, a person skilled in the art will comprehend that various formal and detailed modifications can be made to the contents above without departing from the spirit and scope of the subject matter of the present invention.

What is claimed is:

1. A Mitsugumin 53 (MG53) mutant, wherein the MG53 mutant is identical to the amino acid sequence of a wild-type MG53 except for at least one serine in the coiled-coil-SPRY region of the wild-type MG53, which is deleted and/or mutated into any other non-serine or non-threonine amino acid(s),
wherein the deleted or mutated serine(s) is(are) located at one or more of the following positions of the amino acid sequence of the wild-type MG53: positions 255, 305, 306, and 307, and
wherein the wild-type MG53 is a human, mouse, rat, monkey, swine, or dog wild-type MG53, the MG53 mutant has an amino acid sequence having at least 90% homology to any one of the amino acid sequences set forth in SEQ ID NOs: 7-12 or 147-150, and the MG53 mutant avoids or reduces metabolic side effects compared to the wild-type MG53, while still retaining cell repair function and/or cardioprotective function.

2. The MG53 mutant according to claim 1, wherein the coiled-coil-SPRY region is located at positions 122-477 of the amino acid sequence of the wild-type MG53.

3. The MG53 mutant according to claim 1, wherein the amino acid sequence of the wild-type MG53 is set forth in SEQ ID NO: 1, SEQ ID NO: 2, SEQ ID NO: 3, SEQ ID NO: 4, SEQ ID NO: 5, SEQ ID NO: 6, SEQ ID NO: 139, SEQ ID NO: 140, SEQ ID NO: 141, or SEQ ID NO: 142.

4. The MG53 mutant according to claim 1, wherein the serine is mutated into a non-polar amino acid.

5. The MG53 mutant according to claim 4, wherein the non-polar amino acid is selected from the group consisting of glycine, alanine, leucine, isoleucine, valine, proline, phenylalanine, methionine and tryptophan.

6. The MG53 mutant according to claim 1, wherein the serine is mutated into a non-serine or non-threonine polar amino acid.

7. The MG53 mutant according to claim 6, wherein the polar amino acid is selected from the group consisting of glutamine, cysteine, asparagine, tyrosine, aspartic acid, glutamic acid, lysine, arginine and histidine.

8. The MG53 mutant according to claim 1, wherein the deleted or mutated serine is located at position 255 of the amino acid sequence of the wild-type MG53, or the deleted or mutated serines are located at positions 305, 306 and 307 of the amino acid sequence of the wild-type MG53.

9. The MG53 mutant according to claim 1, wherein the MG53 mutant has an amino acid sequence having at least 95% homology to any one of the amino acid sequences set forth in SEQ ID NOs: 7-12 or 147-150.

10. A MG53 mutant, wherein the amino acid sequence of the MG53 mutant is any one of the amino acid sequences set forth in SEQ ID NOs: 7-12 or 147-150.

11. The MG53 mutant according to claim 10, wherein the amino acid sequence of the MG53 mutant is the amino acid sequence set forth in SEQ ID NO: 7.

12. A pharmaceutical composition comprising the MG53 mutant of claim 1 and a pharmaceutically acceptable carrier.

13. An isolated nucleic acid comprising a nucleic acid sequence encoding the amino acid sequence of the MG53 mutant of claim 1.

14. The nucleic acid according to claim 13 comprising any one of the nucleic acid sequences set forth in SEQ ID NOs: 13-18 or 151-154.

15. An expression vector comprising the nucleic acid sequence according to claim 13.

16. A host cell comprising the expression vector according to claim 15.

17. A method for preparing the MG53 mutant according to claim 1, comprising determining one or more serine positions for mutation, performing site-directed mutagenesis at the position on the full-length sequence of a plasmid comprising the nucleic acid sequence encoding the amino acid sequence of wild-type MG53, transfecting the plasmid with site-directed mutagenesis into a host cell, and inducing the host cell to produce the MG53 mutant.

18. A method for treating heart diseases, diabetic cerebrovascular diseases, diabetic ocular complications, diabetic neuropathy, diabetic foot, kidney diseases, and diseases associated with cellular and/or tissue damage, comprising administering to a subject in need thereof a therapeutically effective amount of the MG53 mutant of claim 1.

19. The method according to claim 18, wherein the MG53 mutant avoids metabolic side effects while treating heart diseases, diabetic cerebrovascular diseases, diabetic ocular complications, diabetic neuropathy, diabetic foot, kidney diseases, and diseases associated with cellular and/or tissue damage.

20. The method according to claim 18, wherein the amino acid sequence of the MG53 mutant is the amino acid sequence set forth in SEQ ID NO: 7.

* * * * *

SEQUENCE LISTING

```
<160> NUMBER OF SEQ ID NOS: 154

<210> SEQ ID NO 1
<211> LENGTH: 477
<212> TYPE: PRT
<213> ORGANISM: Homo sapiens

<400> SEQUENCE: 1

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
```

```
            50                  55                  60
Leu Ser Thr Asn Leu Gln Leu Ala Arg Leu Val Glu Gly Leu Ala Gln
 65                  70                  75                  80

Val Pro Gln Gly His Cys Glu His Leu Asp Pro Leu Ser Ile Tyr
                 85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
                115                 120                 125

Leu Lys Thr Gln Leu Pro Gln Gln Lys Leu Gln Leu Gln Glu Ala Cys
                130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
                180                 185                 190

Glu Ala Glu Arg Val Arg Gly Glu Ala Gly Val Ala Leu Arg Arg Glu
                195                 200                 205

Leu Gly Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
                260                 265                 270

Lys Phe Gln Val Trp Arg Lys Met Phe Arg Ala Leu Met Pro Ala Leu
                275                 280                 285

Glu Glu Leu Thr Phe Asp Pro Ser Ser Ala His Pro Ser Leu Val Val
                290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Asp Val Gly
                340                 345                 350

Asp Lys Pro Arg Trp Ala Leu Gly Val Ile Ala Ala Glu Ala Pro Arg
                355                 360                 365

Arg Gly Arg Leu His Ala Val Pro Ser Gln Gly Leu Trp Leu Leu Gly
                370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
                420                 425                 430

Asp Ala Leu Val Pro Leu Phe Ala Phe His Glu Arg Leu Pro Arg Pro
                435                 440                 445

Val Tyr Pro Phe Phe Asp Val Cys Trp His Asp Lys Gly Lys Asn Ala
                450                 455                 460

Gln Pro Leu Leu Leu Val Gly Pro Glu Gly Ala Glu Ala
465                 470                 475
```

<210> SEQ ID NO 2
<211> LENGTH: 477
<212> TYPE: PRT
<213> ORGANISM: Mus musculus

<400> SEQUENCE: 2

```
Met Ser Ala Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ile Arg Val Ala Gly Glu Pro Ala Ala Asp
        35                  40                  45

Gly Thr Val Ala Cys Pro Cys Cys Gln Ala Pro Thr Arg Pro Gln Ala
    50                  55                  60

Leu Ser Thr Asn Leu Gln Leu Ser Arg Leu Val Glu Gly Leu Ala Gln
65              70                  75                  80

Val Pro Gln Gly His Cys Glu Glu His Leu Asp Pro Leu Ser Ile Tyr
                85                  90                  95

Cys Glu Gln Asp Arg Thr Leu Val Cys Gly Val Cys Ala Ser Leu Gly
            100                 105                 110

Ser His Arg Gly His Arg Leu Leu Pro Ala Ala Glu Ala Gln Ala Arg
        115                 120                 125

Leu Lys Thr Gln Leu Pro Gln Gln Lys Met Gln Leu Gln Glu Ala Cys
    130                 135                 140

Met Arg Lys Glu Lys Thr Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Met Phe Leu Ala Ala Leu Glu Ser Ser Leu Asp Arg
            180                 185                 190

Glu Ala Glu Arg Val Arg Gly Asp Ala Gly Val Ala Leu Arg Arg Glu
        195                 200                 205

Leu Ser Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                245                 250                 255

Pro Pro Ala Arg Leu Asp Ile Gln Leu Pro Val Ile Ser Asp Asp Phe
            260                 265                 270

Lys Phe Gln Val Trp Lys Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Asp Gln Lys Ala Pro Pro
305                 310                 315                 320

Ala Gly Glu Asp Thr Arg Gln Phe Asp Lys Ala Val Ala Val Ala
                325                 330                 335

Gln Gln Leu Leu Ser Gln Gly Glu His Tyr Trp Glu Val Glu Val Gly
            340                 345                 350

Asp Lys Pro Arg Trp Ala Leu Gly Val Met Ala Ala Asp Ala Ser Arg
        355                 360                 365

Arg Gly Arg Leu His Ala Val Pro Ser Gln Gly Leu Trp Leu Leu Gly
```

```
            370                 375                 380
Leu Arg Asp Gly Lys Ile Leu Glu Ala His Val Glu Ala Lys Glu Pro
385                 390                 395                 400

Arg Ala Leu Arg Thr Pro Glu Arg Pro Ala Arg Ile Gly Leu Tyr
            405                 410                 415

Leu Ser Phe Ala Asp Gly Val Leu Ala Phe Tyr Asp Ala Ser Asn Pro
            420                 425                 430

Asp Val Leu Thr Pro Ile Phe Ser Phe His Glu Arg Leu Pro Gly Pro
            435                 440                 445

Val Tyr Pro Ile Phe Asp Val Cys Trp His Asp Lys Gly Lys Asn Ala
            450                 455                 460

Gln Pro Leu Leu Leu Val Gly Pro Glu Gln Glu Gln Ala
465                 470                 475

<210> SEQ ID NO 3
<211> LENGTH: 477
<212> TYPE: PRT
<213> ORGANISM: Rattus norvegicus

<400> SEQUENCE: 3

Met Ser Thr Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ile Arg Val Ala Gly Glu Pro Ala Asp Asp
        35                  40                  45

Gly Thr Val Ala Cys Pro Cys Cys Gln Ala Ser Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Thr Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Ala Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Met Phe Leu Ala Ala Leu Glu Ser Ser Leu Asp Arg
            180                 185                 190

Glu Ala Glu Arg Val Arg Gly Glu Ala Gly Val Ala Leu Arg Arg Glu
        195                 200                 205

Leu Ser Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                245                 250                 255

Pro Pro Ala Arg Leu Asp Ile Gln Leu Pro Val Ile Ser Asp Asp Phe
            260                 265                 270
```

```
Lys Phe Gln Val Trp Lys Lys Met Phe Arg Ala Leu Met Pro Glu Leu
            275                 280                 285

Glu Glu Leu Thr Phe Asp Pro Ser Ser Ala His Pro Ser Leu Val Val
    290                 295                 300

Ser Ala Ser Gly Arg Arg Val Glu Cys Ser Glu Gln Lys Ala Pro Pro
305                 310                 315                 320

Ala Gly Glu Asp Thr Cys Gln Phe Asp Lys Thr Val Ala Val Val Ala
                325                 330                 335

Lys Gln Leu Leu Ser Gln Gly Glu His Tyr Trp Glu Val Glu Val Gly
            340                 345                 350

Asp Lys Pro Arg Trp Ala Leu Gly Val Met Ala Ala Asp Ala Ser Arg
        355                 360                 365

Arg Gly Arg Leu His Ala Val Pro Ser Gln Gly Leu Trp Leu Leu Gly
    370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Ala Arg Ile Gly Leu Tyr
                405                 410                 415

Leu Ser Phe Ala Asp Gly Val Leu Thr Phe Tyr Asp Ala Ser Asn Thr
            420                 425                 430

Asp Ala Leu Thr Pro Leu Phe Ser Phe His Glu Arg Leu Pro Gly Pro
        435                 440                 445

Val Tyr Pro Met Phe Asp Val Cys Trp His Asp Lys Gly Lys Asn Ser
    450                 455                 460

Gln Pro Leu Leu Leu Val Gly Pro Asp Ser Glu Gln Ala
465                 470                 475

<210> SEQ ID NO 4
<211> LENGTH: 477
<212> TYPE: PRT
<213> ORGANISM: Macaca fascicularis

<400> SEQUENCE: 4

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175
```

```
Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Glu Val Gly
            340                 345                 350

Asp Lys Pro Arg Trp Ala Leu Gly Val Ile Ala Ala Glu Gly Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Gly Pro
        435                 440                 445

Val Tyr Pro Phe Phe Asp Val Cys Trp His Asp Lys Gly Lys Asn Ser
    450                 455                 460

Gln Pro Leu Leu Leu Val Gly Ser Glu Gly Ala Glu Ala
465                 470                 475

<210> SEQ ID NO 5
<211> LENGTH: 478
<212> TYPE: PRT
<213> ORGANISM: Sus scrofa

<400> SEQUENCE: 5

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Ser Cys Gln Ala Pro Thr Arg Pro Gln Ala
    50                  55                  60

Leu Ser Thr Asn Gln Gln Leu Ala Arg Leu Val Glu Gly Leu Ala Gln
```

-continued

```
                65                  70                  75                  80
        Val Pro Gln Gly His Cys Glu Glu His Leu Asp Pro Leu Ser Ile Tyr
                            85                  90                  95
        Cys Glu Gln Asp Arg Val Leu Val Cys Gly Val Cys Ala Ser Leu Gly
                        100                 105                 110
        Ser His Arg Gly His Arg Leu Leu Pro Ala Ala Glu Ala His Ala Arg
                    115                 120                 125
        Leu Lys Thr Gln Leu Pro Gln Gln Lys Leu Gln Leu Gln Glu Ala Cys
                130                 135                 140
        Met Arg Lys Glu Lys Ser Val Gly Val Leu Glu Gln Leu Val Glu
        145                 150                 155                 160
        Val Glu Glu Thr Val Arg Gln Phe Arg Gly Ala Val Gly Glu Gln Leu
                            165                 170                 175
        Gly Lys Met Arg Leu Phe Leu Ala Ala Leu Glu Gly Ser Leu Asp Arg
                        180                 185                 190
        Glu Ala Glu Arg Val Arg Gly Glu Ala Gly Val Ala Leu Arg Arg Glu
                    195                 200                 205
        Leu Gly Ser Leu Lys Ser Tyr Leu Glu Gln Leu Arg Gln Met Glu Lys
                210                 215                 220
        Val Leu Glu Glu Val Ala Asp Lys Pro Gln Thr Glu Phe Leu Met Lys
        225                 230                 235                 240
        Tyr Cys Leu Val Thr Ser Arg Leu Gln Lys Ile Leu Ala Glu Ser Pro
                            245                 250                 255
        Pro Pro Ala Arg Leu Asp Ile Gln Leu Pro Val Ile Ser Asp Asp Phe
                        260                 265                 270
        Lys Phe Gln Val Trp Arg Lys Met Phe Arg Ala Leu Met Pro Ala Met
                    275                 280                 285
        Gln Glu Leu Thr Phe Asp Pro Ser Thr Ala His Pro Ser Leu Val Leu
                290                 295                 300
        Ser Ala Ser Gly Arg Arg Val Glu Cys Ser Glu Gln Lys Ala Pro Pro
        305                 310                 315                 320
        Ala Gly Glu Asp Pro Arg Gln Phe Asp Lys Ala Val Ala Val Thr
                            325                 330                 335
        His Gln Leu Leu Ser Glu Gly Glu His Tyr Trp Glu Val Glu Val Gly
                        340                 345                 350
        Asp Lys Pro Arg Trp Ala Leu Gly Val Ile Gly Ala Gln Ala Gly Arg
                    355                 360                 365
        Arg Gly Arg Leu His Ala Val Pro Ser Gln Gly Leu Trp Leu Leu Gly
                370                 375                 380
        Leu Arg Glu Gly Lys Ile Leu Glu Ala His Val Glu Ala Lys Glu Pro
        385                 390                 395                 400
        Arg Ala Leu Arg Thr Pro Glu Arg Arg Pro Ser Arg Ile Gly Ile Tyr
                            405                 410                 415
        Leu Ser Phe Ala Asp Gly Val Leu Ser Phe Tyr Asp Ala Ser Asp Ala
                        420                 425                 430
        Asp Ala Leu Glu Leu Leu Phe Ala Phe His Glu Arg Leu Pro Gly Pro
                    435                 440                 445
        Val Tyr Pro Phe Phe Asp Val Cys Trp His Asp Lys Gly Lys Asn Ala
                450                 455                 460
        Gln Pro Leu Leu Leu Val Gly Pro Asp Ser Gly Glu Ala
        465                 470                 475

<210> SEQ ID NO 6
```

<211> LENGTH: 477
<212> TYPE: PRT
<213> ORGANISM: Canis lupus familiaris

<400> SEQUENCE: 6

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ser Arg Val Ala Gly Glu Pro Ala Ala Asp
        35                  40                  45

Gly Thr Val Pro Cys Pro Cys Cys Gln Ala Leu Thr Arg Pro Gln Ala
    50                  55                  60

Leu Ser Thr Asn Gln Gln Leu Ala Arg Leu Val Glu Gly Leu Ala Gln
65                  70                  75                  80

Val Pro Gln Gly His Cys Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Leu Leu Glu His Gln Leu Met Glu
145                 150                 155                 160

Val Glu Glu Met Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Val Ile Ser Asp Asp Phe
            260                 265                 270

Lys Phe Gln Val Trp Arg Lys Met Phe Arg Ala Leu Met Pro Val Thr
        275                 280                 285

Lys Glu Leu Thr Phe Asp Pro Ser Ser Ala His Pro Ser Leu Val Leu
    290                 295                 300

Ser Pro Ser Gly Arg Arg Val Glu Cys Ser Asp Gln Lys Ala Pro Pro
305                 310                 315                 320

Ala Gly Glu Asp Pro Cys Gln Phe Asp Lys Ala Val Ala Val Val Ala
                325                 330                 335

Gln Gln Val Leu Ser Asp Gly Glu His Tyr Trp Glu Val Gln Val Gly
            340                 345                 350

Glu Lys Pro Arg Trp Ala Leu Gly Val Ile Ala Ala Gln Ala Ser Arg
        355                 360                 365

Arg Gly Arg Leu His Ala Val Pro Ser Gln Gly Leu Trp Leu Leu Gly
    370                 375                 380

Leu Arg Asp Gly Lys Ile Leu Glu Ala His Val Glu Ala Lys Glu Pro
```

```
                385                 390                 395                 400
Arg Ala Leu Arg Thr Pro Glu Arg Arg Pro Thr Arg Ile Gly Ile Tyr
                    405                 410                 415

Leu Ser Phe Gly Asp Gly Val Leu Ser Phe Tyr Asp Ala Ser Asp Pro
            420                 425                 430

Asp Ala Leu Glu Leu Leu Phe Ala Phe His Glu Arg Leu Pro Gly Pro
        435                 440                 445

Val Tyr Pro Phe Phe Asp Val Cys Trp His Asp Lys Gly Lys Asn Ala
    450                 455                 460

Gln Pro Leu Leu Leu Val Gly Pro Asp Gly Glu Glu Ala
465                 470                 475

<210> SEQ ID NO 7
<211> LENGTH: 477
<212> TYPE: PRT
<213> ORGANISM: Artificial Sequence
<220> FEATURE:
<223> OTHER INFORMATION: Amino acid sequence of human MG53 S255A mutant

<400> SEQUENCE: 7

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ala Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
```

-continued

```
              275                 280                 285
Glu Glu Leu Thr Phe Asp Pro Ser Ser Ala His Pro Ser Leu Val Val
        290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Arg Pro
        435                 440                 445

Val Tyr Pro Phe Phe Asp Val Cys Trp His Asp Lys Gly Lys Asn Ala
    450                 455                 460

Gln Pro Leu Leu Leu Val Gly Pro Glu Gly Ala Glu Ala
465                 470                 475

<210> SEQ ID NO 8
<211> LENGTH: 477
<212> TYPE: PRT
<213> ORGANISM: Artificial Sequence
<220> FEATURE:
<223> OTHER INFORMATION: Amino acid sequence of mouse MG53 S255A mutant

<400> SEQUENCE: 8

Met Ser Ala Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ile Arg Val Ala Gly Glu Pro Ala Ala Asp
        35                  40                  45

Gly Thr Val Ala Cys Pro Cys Cys Gln Ala Pro Thr Arg Pro Gln Ala
    50                  55                  60

Leu Ser Thr Asn Leu Gln Leu Ser Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Thr Leu Val Cys Gly Val Cys Ala Ser Leu Gly
            100                 105                 110

Ser His Arg Gly His Arg Leu Leu Pro Ala Ala Glu Ala Gln Ala Arg
        115                 120                 125

Leu Lys Thr Gln Leu Pro Gln Gln Lys Met Gln Leu Glu Ala Cys
    130                 135                 140

Met Arg Lys Glu Lys Thr Val Ala Val Leu Glu His Gln Leu Val Glu
145                 150                 155                 160

Val Glu Glu Thr Val Arg Gln Phe Arg Gly Ala Val Gly Glu Gln Leu
```

```
            165                 170                 175
Gly Lys Met Arg Met Phe Leu Ala Ala Leu Glu Ser Ser Leu Asp Arg
            180                 185                 190

Glu Ala Glu Arg Val Arg Gly Asp Ala Gly Val Ala Leu Arg Arg Glu
            195                 200                 205

Leu Ser Ser Leu Asn Ser Tyr Leu Glu Gln Leu Arg Gln Met Glu Lys
            210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ala Pro
                245                 250                 255

Pro Pro Ala Arg Leu Asp Ile Gln Leu Pro Val Ile Ser Asp Asp Phe
                260                 265                 270

Lys Phe Gln Val Trp Lys Lys Met Phe Arg Ala Leu Met Pro Ala Leu
                275                 280                 285

Glu Glu Leu Thr Phe Asp Pro Ser Ser Ala His Pro Ser Leu Val Val
            290                 295                 300

Ser Ser Ser Gly Arg Arg Val Glu Cys Ser Asp Gln Lys Ala Pro Pro
305                 310                 315                 320

Ala Gly Glu Asp Thr Arg Gln Phe Asp Lys Ala Val Ala Val Val Ala
                325                 330                 335

Gln Gln Leu Leu Ser Gln Gly Glu His Tyr Trp Glu Val Glu Val Gly
            340                 345                 350

Asp Lys Pro Arg Trp Ala Leu Gly Val Met Ala Ala Asp Ala Ser Arg
                355                 360                 365

Arg Gly Arg Leu His Ala Val Pro Ser Gln Gly Leu Trp Leu Leu Gly
            370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Pro Ala Arg Ile Gly Leu Tyr
                405                 410                 415

Leu Ser Phe Ala Asp Gly Val Leu Ala Phe Tyr Asp Ala Ser Asn Pro
                420                 425                 430

Asp Val Leu Thr Pro Ile Phe Ser Phe His Glu Arg Leu Pro Gly Pro
                435                 440                 445

Val Tyr Pro Ile Phe Asp Val Cys Trp His Asp Lys Gly Lys Asn Ala
            450                 455                 460

Gln Pro Leu Leu Leu Val Gly Pro Glu Gln Glu Gln Ala
465                 470                 475

<210> SEQ ID NO 9
<211> LENGTH: 477
<212> TYPE: PRT
<213> ORGANISM: Artificial Sequence
<220> FEATURE:
<223> OTHER INFORMATION: Amino acid sequence of rat MG53 S255A mutant

<400> SEQUENCE: 9

Met Ser Thr Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
                20                  25                  30

Phe Cys Arg Ala Cys Leu Ile Arg Val Ala Gly Glu Pro Ala Asp Asp
            35                  40                  45

Gly Thr Val Ala Cys Pro Cys Cys Gln Ala Ser Thr Arg Pro Gln Ala
```

```
                 50                  55                  60
Leu Ser Thr Asn Leu Gln Leu Ala Arg Leu Val Glu Gly Leu Ala Gln
 65                      70                  75                  80

Val Pro Gln Gly His Cys Glu His Leu Asp Pro Leu Ser Ile Tyr
                 85                  90                  95

Cys Glu Gln Asp Arg Thr Leu Val Cys Gly Val Cys Ala Ser Leu Gly
                    100                 105                 110

Ser His Arg Gly His Arg Leu Leu Pro Ala Ala Glu Ala His Ala Arg
            115                 120                 125

Leu Lys Thr Gln Leu Pro Gln Gln Lys Ala Gln Leu Gln Glu Ala Cys
            130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                    165                 170                 175

Gly Lys Met Arg Met Phe Leu Ala Ala Leu Glu Ser Ser Leu Asp Arg
            180                 185                 190

Glu Ala Glu Arg Val Arg Gly Glu Ala Gly Val Ala Leu Arg Arg Glu
            195                 200                 205

Leu Ser Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ala Pro
                    245                 250                 255

Pro Pro Ala Arg Leu Asp Ile Gln Leu Pro Val Ile Ser Asp Asp Phe
            260                 265                 270

Lys Phe Gln Val Trp Lys Lys Met Phe Arg Ala Leu Met Pro Glu Leu
            275                 280                 285

Glu Glu Leu Thr Phe Asp Pro Ser Ser Ala His Pro Ser Leu Val Val
            290                 295                 300

Ser Ala Ser Gly Arg Arg Val Glu Cys Ser Glu Gln Lys Ala Pro Pro
305                 310                 315                 320

Ala Gly Glu Asp Thr Cys Gln Phe Asp Lys Thr Val Ala Val Val Ala
                    325                 330                 335

Lys Gln Leu Leu Ser Gln Gly Glu His Tyr Trp Glu Val Glu Val Gly
            340                 345                 350

Asp Lys Pro Arg Trp Ala Leu Gly Val Met Ala Ala Asp Ala Ser Arg
            355                 360                 365

Arg Gly Arg Leu His Ala Val Pro Ser Gln Gly Leu Trp Leu Leu Gly
    370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Pro Ala Arg Ile Gly Leu Tyr
                    405                 410                 415

Leu Ser Phe Ala Asp Gly Val Leu Thr Phe Tyr Asp Ala Ser Asn Thr
            420                 425                 430

Asp Ala Leu Thr Pro Leu Phe Ser Phe His Glu Arg Leu Pro Gly Pro
            435                 440                 445

Val Tyr Pro Met Phe Asp Val Cys Trp His Asp Lys Gly Lys Asn Ser
            450                 455                 460

Gln Pro Leu Leu Leu Val Gly Pro Asp Ser Glu Gln Ala
465                 470                 475
```

<210> SEQ ID NO 10
<211> LENGTH: 477
<212> TYPE: PRT
<213> ORGANISM: Artificial Sequence
<220> FEATURE:
<223> OTHER INFORMATION: Amino acid sequence of monkey MG53 S255A mutant

<400> SEQUENCE: 10

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
                20                  25                  30

Phe Cys Arg Ala Cys Leu Gly Arg Val Ala Gly Glu Pro Ala Ala Asp
            35                  40                  45

Gly Thr Val Leu Cys Pro Cys Cys Gln Ala Pro Thr Arg Pro Gln Ala
        50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Leu Gln Leu Gln Glu Ala Cys
        130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ala Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Glu Val Gly
            340                 345                 350

Asp Lys Pro Arg Trp Ala Leu Gly Val Ile Ala Ala Glu Gly Pro Arg
        355                 360                 365
```

-continued

```
Arg Gly Arg Leu His Ala Val Pro Ser Gln Gly Leu Trp Leu Gly
        370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Gly Pro
        435                 440                 445

Val Tyr Pro Phe Phe Asp Val Cys Trp His Asp Lys Gly Lys Asn Ser
    450                 455                 460

Gln Pro Leu Leu Leu Val Gly Ser Glu Gly Ala Glu Ala
465                 470                 475

<210> SEQ ID NO 11
<211> LENGTH: 478
<212> TYPE: PRT
<213> ORGANISM: Artificial Sequence
<220> FEATURE:
<223> OTHER INFORMATION: Amino acid sequence of swine MG53 S255A mutant

<400> SEQUENCE: 11

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Ser Cys Gln Ala Pro Thr Arg Pro Gln Ala
    50                  55                  60

Leu Ser Thr Asn Gln Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Val Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Gly Val Leu Glu Gln Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Leu Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Lys Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ala Pro
                245                 250                 255
```

Pro Pro Ala Arg Leu Asp Ile Gln Leu Pro Val Ile Ser Asp Asp Phe
        260                 265                 270

Lys Phe Gln Val Trp Arg Lys Met Phe Arg Ala Leu Met Pro Ala Met
        275                 280                 285

Gln Glu Leu Thr Phe Asp Pro Ser Thr Ala His Pro Ser Leu Val Leu
        290                 295                 300

Ser Ala Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Thr
                325                 330                 335

His Gln Leu Leu Ser Glu Gly Glu His Tyr Trp Glu Val Glu Val Gly
        340                 345                 350

Asp Lys Pro Arg Trp Ala Leu Gly Val Ile Gly Ala Gln Ala Gly Arg
        355                 360                 365

Arg Gly Arg Leu His Ala Val Pro Ser Gln Gly Leu Trp Leu Leu Gly
        370                 375                 380

Leu Arg Glu Gly Lys Ile Leu Glu Ala His Val Glu Ala Lys Glu Pro
385                 390                 395                 400

Arg Ala Leu Arg Thr Pro Glu Arg Arg Pro Ser Arg Ile Gly Ile Tyr
                405                 410                 415

Leu Ser Phe Ala Asp Gly Val Leu Ser Phe Tyr Asp Ala Ser Asp Ala
        420                 425                 430

Asp Ala Leu Glu Leu Leu Phe Ala Phe His Glu Arg Leu Pro Gly Pro
        435                 440                 445

Val Tyr Pro Phe Phe Asp Val Cys Trp His Asp Lys Gly Lys Asn Ala
        450                 455                 460

Gln Pro Leu Leu Leu Val Gly Pro Asp Ser Gly Gly Glu Ala
465                 470                 475

<210> SEQ ID NO 12
<211> LENGTH: 477
<212> TYPE: PRT
<213> ORGANISM: Artificial Sequence
<220> FEATURE:
<223> OTHER INFORMATION: Amino acid sequence of dog MG53 S255A mutant

<400> SEQUENCE: 12

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ser Arg Val Ala Gly Glu Pro Ala Ala Asp
        35                  40                  45

Gly Thr Val Pro Cys Pro Cys Cys Gln Ala Leu Thr Arg Pro Gln Ala
    50                  55                  60

Leu Ser Thr Asn Gln Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Leu Leu Glu His Gln Leu Met Glu
145                 150                 155                 160

Val Glu Glu Met Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ala Pro
                245                 250                 255

Pro Pro Ala Arg Leu Asp Ile Gln Leu Pro Val Ile Ser Asp Asp Phe
            260                 265                 270

Lys Phe Gln Val Trp Arg Lys Met Phe Arg Ala Leu Met Pro Val Thr
        275                 280                 285

Lys Glu Leu Thr Phe Asp Pro Ser Ser Ala His Pro Ser Leu Val Leu
    290                 295                 300

Ser Pro Ser Gly Arg Arg Val Glu Cys Ser Asp Gln Lys Ala Pro Pro
305                 310                 315                 320

Ala Gly Glu Asp Pro Cys Gln Phe Asp Lys Ala Val Ala Val Val Ala
                325                 330                 335

Gln Gln Val Leu Ser Asp Gly Glu His Tyr Trp Glu Val Gln Val Gly
            340                 345                 350

Glu Lys Pro Arg Trp Ala Leu Gly Val Ile Ala Ala Gln Ala Ser Arg
        355                 360                 365

Arg Gly Arg Leu His Ala Val Pro Ser Gln Gly Leu Trp Leu Leu Gly
    370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Arg Pro Thr Arg Ile Gly Ile Tyr
                405                 410                 415

Leu Ser Phe Gly Asp Gly Val Leu Ser Phe Tyr Asp Ala Ser Asp Pro
            420                 425                 430

Asp Ala Leu Glu Leu Leu Phe Ala Phe His Glu Arg Leu Pro Gly Pro
        435                 440                 445

Val Tyr Pro Phe Phe Asp Val Cys Trp His Asp Lys Gly Lys Asn Ala
    450                 455                 460

Gln Pro Leu Leu Leu Val Gly Pro Asp Gly Glu Glu Ala
465                 470                 475

<210> SEQ ID NO 13
<211> LENGTH: 1434
<212> TYPE: DNA
<213> ORGANISM: Artificial Sequence
<220> FEATURE:
<223> OTHER INFORMATION: Encoding sequence of human MG53 S255A mutant

<400> SEQUENCE: 13
atgtcggctg cgcccggcct cctgcaccag gagctgtcct gcccgctgtg cctgcagctg     60
ttcgacgcgc ccgtgacagc cgagtgcggc cacagtttct gccgcgcctg cctaggccgc    120
gtggccgggg agccggcggc ggatggcacc gttctctgcc cctgctgcca ggcccccacg    180

```
cggccgcagg cactcagcac caacctgcag ctggcgcgcc tggtggaggg gctggcccag      240
gtgccgcagg gccactgcga ggagcacctg gacccgctga gcatctactg cgagcaggac      300
cgcgcgctgg tgtgcggagt gtgcgcctca ctcggctcgc accgcggtca tcgcctcctg      360
cctgccgccg aggcccacgc acgcctcaag acacagctgc acagcagaa actgcagctg       420 caggaggcat gcatgcgcaa ggagaagagt gtggctgtgc tggagcatca gctggtggag      480
gtggaggaga cagtgcgtca gttccggggg gccgtggggg agcagctggg caagatgcgg      540
gtgttcctgg ctgcactgga gggctccttg accgcgagg cagagcgtgt acggggtgag       600
gcaggggtcg ccttgcgccg ggagctgggg agcctgaact cttacctgga gcagctgcgg      660
cagatggaga aggtcctgga ggaggtggcg gacaagccgc agactgagtt cctcatgaaa      720
tactgcctgt gaccagcag gctgcagaag atcctggcag aggctccccc acccgcccgt       780
ctggacatcc agctgccaat tatctcagat gacttcaaat tccaggtgtg gaggaagatg      840
ttccgggctc tgatgccagc gctggaggag ctgacctttg acccgagctc tgcgcacccg      900
agcctggtgg tgtcttcctc tggccgccgc gtggagtgct cggagcagaa ggcgccgccg      960
gccggggagg acccgcgcca gttcgacaag gcggtggcgg tggtgcgca ccagcagctc      1020 tccgagggcg agcactactg ggaggtggat gttggcgaca agccgcgctg ggcgctgggc     1080
gtgatcgcgg ccgaggcccc ccgccgcggg cgcctgcacg cggtgccctc gcagggcctg     1140
tggctgctgg ggctgcgcga gggcaagatc ctggaggcac acgtggaggc caaggagccg     1200
cgcgctctgc gcagccccga gaggcggccc acgcgcattg ccctttacct gagcttcggc     1260
gacggcgtcc tctccttcta cgatgccagc gacgccgacg cgctcgtgcc gcttttttgcc    1320 ttccacgagc gcctgcccag gcccgtgtac cccttcttcg acgtgtgctg gcacgacaag     1380
ggcaagaatg cccagccgct gctgctcgtg ggtcccgaag cgccgaggc ctga            1434

<210> SEQ ID NO 14
<211> LENGTH: 1434
<212> TYPE: DNA
<213> ORGANISM: Artificial Sequence
<220> FEATURE:
<223> OTHER INFORMATION: Encoding sequence of mouse MG53 S255A mutant

<400> SEQUENCE: 14
atgtcggctg cacccggcct tctgcgtcag gaactgtcct gcccactgtg cttgcagctg       60
ttcgatgcgc cagtgacggc tgagtgtggc cacagtttct gccgtgcctg cctgatccgg      120
gtggcagggg agcctgctgc ggacggcaca gttgcctgtc cctgttgtca ggcacctaca      180
cggccgcagg ctctaagcac taacctccag ttgtcacgcc ttgtggaggg tttggcgcaa      240 gtgcccaag gccactgcga ggaacacctg gatccactga gcatctactg cgagcaggac       300
cgcacacttg tgtgtggtgt gtgtgcctcg ctcggttctc accgtggtca tcgtctcctg      360
cctgccgctg aagcccaagc acgcctcaag acacagcttc acagcagaa gatgcagctg       420 caggaggcat gcatgcgcaa ggagaagact gtagcggtgc tggagcatca gctggtggag      480
gtggaggaga cagtgcgcca gttccgggga gctgtcgggg agcagctggg gaagatgcgg      540
atgttcctgg ctgccctaga aagttctctg accgtgaag cagaagggt tcggggtgat        600 gctgggggttg ccttgcgtcg ggagctgtca agcctgaact cttacctaga gcaactgagg     660
cagatggaga aggtgctgga ggaggtggct gacaagccac agacagaatt cctcatgaaa     720
ttctgcctgg taaccagcag gctgcagaag atcctgtcag aggcaccacc accggcaagg     780
```

| | |
|---|---|
| ctagatatcc agctgcctgt catctcagat gacttcaaat tccaggtgtg aagaagatg | 840 |
| ttccgggctc tgatgccagc gctggaggaa ctgacttttg accccagctc tgcgcacccg | 900 |
| agcctggtgg tgtcctcctc tggtcgccga gtggagtgct cagaccagaa ggcgccgcca | 960 |
| gcgggagaag acacgcgtca gttcgacaag gcagtagcgg tggtggcgca gcagctgctg | 1020 |
| tcacagggcg agcactattg ggaggtggag gtgggcgaca accacgctg ggccctggga | 1080 |
| gtgatggcgg ctgacgcttc ccgccgtggc cggctgcacg cggtgccctc acaggggctg | 1140 |
| tggctgctgg gtctgcgcga tggcaagatc ctggaggcgc acgtggaggc caaggagccg | 1200 |
| cgggcactgc gcaccccaga gaggcctccg gcgcgcattg gcctctacct aagcttcgca | 1260 |
| gatggcgtcc tggctttcta tgatgcgagc aaccccgacg tacttacgcc aatcttttct | 1320 |
| ttccacgagc gtctgcccgg gccggtgtac cccatctttg acgtgtgctg gcacgacaag | 1380 |
| ggcaagaatg cccagcccct gctgcttgtg gggccggagc aggaacaggc ctga | 1434 |

<210> SEQ ID NO 15
<211> LENGTH: 1434
<212> TYPE: DNA
<213> ORGANISM: Artificial Sequence
<220> FEATURE:
<223> OTHER INFORMATION: Encoding sequence of rat MG53 S255A mutant

<400> SEQUENCE: 15

| | |
|---|---|
| atgtcgactg caccaggcct tttgcgccag gaactgtctt gcccgctgtg cttgcagctg | 60 |
| ttcgatgcac cagtgaccgc tgagtgtggc cacagtttct gccgtgcctg cctgatccgt | 120 |
| gtggcagggg agcctgccga cgatggcacg gttgcctgtc cctgttgtca ggcatctact | 180 |
| cggccacagg cgctaagcac taacctccag ttggcacgcc ttgtggaggg tttggcacaa | 240 |
| gtgccccaag ccactgcga ggaacacctg gatccactga gcatctactg cgagcaggac | 300 |
| cgcacacttg tgtgtggtgt gtgtgcctct ctcggttcac accgtggtca ccgtcttctg | 360 |
| cctgccgcag aagcccatgc acgtctcaag acacagcttc cacaacagaa ggcccagctg | 420 |
| caggaggcat gcatgcgcaa ggagaagagt gtagcagtcc tggagcatca gctggtggag | 480 |
| gtggaggaga ccgtgcgtca gttccgggga gctgttgggg agcagctggg gaagatgcgg | 540 |
| atgttcctgg ctgccctaga aagttctttg gaccgtgaag cagaaagggt tcgaggtgag | 600 |
| gcagggggttg ccttgcggcg ggagctgtca agcctgaact cttacctgga gcaactgagg | 660 |
| cagatggaga aggtgctgga ggaggtggct gacaagccac agacagaatt cctcatgaaa | 720 |
| ttctgcctgg tgaccagcag gctgcagaag attctgtcag aggcaccacc cccagcaagg | 780 |
| ctagatatcc agctgcctgt catctcagat gacttcaaat tccaggtgtg aagaagatg | 840 |
| ttccgggctc tgatgccaga gttggaggaa ctgacttttg accccagctc tgcgcacccg | 900 |
| agcctggtgg tgtccgcctc tggtcgccga gtggagtgct cggagcagaa ggcgccgcca | 960 |
| gcaggagaag acacgtgcca gttcgacaag acgtagcgg tagtggcgaa gcagctgctg | 1020 |
| tcacaggggg agcactactg ggaggtggag gtgggcgaca agccacgctg ggccctgggt | 1080 |
| gtgatggcgg ctgacgcttc ccgtcgtggc cgcctgcacg cggtgccctc acaggggctg | 1140 |
| tggttgctcg gcctgcgcga tggcaagatc ctggaggcac acgtggaggc caaggagcca | 1200 |
| cgggcactgc gcaccccaga gaggccacca gcgcgcattg gcctctacct aagctttgca | 1260 |
| gatggcgtcc tgactttcta tgatgcaagc aacaccgacg cgcttacacc gctctttttct | 1320 |
| tttcatgagc gtctgcctgg gccggtgtac cccatgtttg acgtgtgctg gcacgacaag | 1380 |
| ggcaagaatt ctcagccgct gttgctcgtg gggccagaca gtgagcaggc ctga | 1434 |

<210> SEQ ID NO 16
<211> LENGTH: 1434
<212> TYPE: DNA
<213> ORGANISM: Artificial Sequence
<220> FEATURE:
<223> OTHER INFORMATION: Encoding sequence of monkey MG53 S255A mutant

<400> SEQUENCE: 16

```
atgtcggctg cgccgggcct cctgcaccag gagctgtcct gcccgctgtg cctgcagctg      60
ttcgacgcgc ccgtgacagc cgagtgcggc cacagtttct gtcgcgcctg cctgggccgc     120
gtggccgggg aaccggcggc ggatggcacc gttctctgcc cctgctgtca ggcccccacg     180
cggccgcagg cactcagcac caacctgcag ctggcgcgcc tggtggaggg gctggcccag     240
gtgccgcagg ccactgcgga ggagcacctg gaccgctga gcatctactg tgagcaggac     300
cgcgcgctgg tgtgcggagt gtgcgcctca ctcggctcgc accgcggtca tcgcctgctg     360
cccgccgccg aggcccacgc acgcctcaag acgcagctgc acagcagaa actgcagctg     420
caggaggcat gcatgcgcaa ggagaagagt gtagctgtgc tggagcatca gttggtggaa     480
gtggaggaga cagtgcgtca gttccggggg gccgtggggg agcagctggg caagatgcgg     540
gtgttcctgg ctgcactgga gggctccttg accgtgagg cagagcgtgt gcggggtgag     600
gcaggggtcg ccttgcgccg ggagctgggg agcctgaact cttacctgga gcagctgcgg     660
cagatggaga aggtgctgga ggaggtggcc gacaagccgc agactgagtt cctaatgaaa     720
tactgcctgg tgaccagcag gctgcagaag atcctggcag aggctccccc acccgcccgt     780
ctggacatcc agctgccaat catctcagat gacttcaaat tccaggtgtg gaggaagatg     840
ttccgggctc tgatgccagc gctggaggag ctgacctttg acccgagctc tgcgcacccc     900
agcctggtgg tgtcttcctc cggccgccgc gtggagtgct cggagcagaa ggcgccgccg     960
gcggggagg acccgcgcca gttcgacaag gcggtagcgg tggtggcgca ccagcagctc    1020
tccgagggcg aacactactg ggaggtggag gtgggcgaca gccgcgctg ggcgctgggt    1080
gtgatcgcgg ccgaggggcc ccgtcgcggg cgcctgcacg cggtgccctc gcagggcctg    1140
tggctgctgg ggctgcgtga gggcaagatc ctggaggctc acgtggaggc caaggagccg    1200
cgcgctctgc gcagccccga gcggcggccc acgcgcatcg gcctctacct gagcttcggc    1260
gacggcgtcc tctccttcta cgatgccagc gacgccgacg cgctcgtgcc gcttttgcc    1320
ttccacgagc gcctgcctgg gcccgtgtac cccttcttcg acgtgtgctg gcacgacaag    1380
ggcaagaact cccagccgct gctgctcgtg gggtccgaag cgccgaagc ctga          1434
```

<210> SEQ ID NO 17
<211> LENGTH: 1437
<212> TYPE: DNA
<213> ORGANISM: Artificial Sequence
<220> FEATURE:
<223> OTHER INFORMATION: Encoding sequence of swine MG53 S255A mutant

<400> SEQUENCE: 17

```
atgtcagctg cgcccggcct cctgcaccag gagctgtcct gtccgctgtg cctgcagctg      60
ttcgatgcgc cggtgacggc tgagtgcggc cacagcttct gccgcgcctg cctgggccgc     120
gtggcagggg agccagccgc ggatggcacg gtgctctgcc ccagctgcca gcacccacg     180
cggccgcagg cgctcagcac caaccagcag ctggcgcgcc tggtggaggg gctggcgcag     240
gtgccgcagg ccactgcgga ggagcaccta gaccgctca gcatctactg cgagcaggac     300
```

```
cgcgtgctcg tgtgcggcgt ctgcgcctcg ctgggttcgc accgcggcca ccgcctgctg    360
cccgccgccg aagcccatgc gcgccttaag acgcagctcc cgcagcagaa gctgcagctg    420
caggaggcgt gtatgcggaa ggagaagagc gtgggtgtgc tggagcaaca actggtggaa    480
gtggaggaga cggtgcgtca gttccggggg gcagtggggg agcagctggg caagatgcgg    540
ttgttcctgg ctgcactgga gggctccttg gaccgagaag cagagcgtgt gcggggtgag    600
gcggggtcg ccttgcggag ggagctgggg agcctgaagt cttacttgga gcagctgcgg    660
cagatggaga aggtgctgga ggaggtggca gacaagcccc agaccgagtt cctcatgaaa    720
tactgcctgg tgaccagcag gctgcagaag atcctggcag aggcgccccc acctgcccgc    780
ctggacattc agctgcctgt catctcagac gacttcaaat tccaggtgtg gagaaagatg    840
ttccgggccc tgatgccagc gatgcaggag ctgacctttg accccagcac ggcccacccg    900
agcctggtgc tgtcggcctc gggccgccgc gtggagtgct cggagcagaa ggcgccgccg    960
gccggagagg accgcgcca gttcgacaag gcggtggcgg tggtgacgca ccagctgctg   1020
tcggaaggcg agcactactg ggaggtggag gtgggcgaca agccacgctg ggcgctgggc   1080
gtgatcgggg cccaggccgg tcgccgcggc cggctgcacg ccgtgccctc gcagggcctc   1140
tggctgctcg ggctgcgcga gggcaagatc ctggaggctc acgtcgaggc caaggagccg   1200
cgcgccctgc gcaccccgga gaggcggccg tcgcgcatcg ggatctacct gagcttcgcg   1260
gatggcgtcc tctcgttcta cgacgccagc gacgccgacg cgctggagct gctcttcgcc   1320
ttccacgaac gcctgccggg ccccgtgtac cccttcttcg acgtgtgctg gcacgacaag   1380
ggcaagaacg ctcagccgct cctgctggtg gggcccgaca gcggcgggga ggcctga     1437

<210> SEQ ID NO 18
<211> LENGTH: 1434
<212> TYPE: DNA
<213> ORGANISM: Artificial Sequence
<220> FEATURE:
<223> OTHER INFORMATION: Encoding sequence of dog MG53 S255A mutant

<400> SEQUENCE: 18
atgtcggccg cgccgggcct cctgcaccag gagctgtcct gccgctctg cctgcagctg     60
tttgacgcgc cggtgaccgc cgagtgcggc cacagtttct gccgcgcctg cctgagccgc    120
gtggctgggg agcggcggc ggacggcacc gtgccctgcc cgtgctgcca ggcactcacg    180
cggccacagg cgctcagcac caaccagcag ctggcgcgcc tggtggaggg gctggcgcag    240
gtgccgcagg gccactgcga ggagcaccta gacccgctca gcatctactg cgagcaggat    300
cgagcgctcg tgtgcggcgt gtgcgcctcg ctcggctcgc accgcggcca ccgcctgctg    360
cccgccgccg aagcccacgc gcgcctcaag acacagctgc acagcagaa actgcagctg    420
caggaggcat gtatgcgcaa ggagaagagt gtggctctgc tggagcatca gctcatggaa    480
gtggaggaga tggtgcgtca gttccggggg gctgtagggg agcagctggg caagatgcgg    540
gtgttcctgg ctgcactgga gggctccttg gaccgtgagg cagagcgcgt gcggggagag    600
gcaggggttg ccctgcggcg ggagctgggg agcctgaact cttacctgga gcagttgcgt    660
cagatggaga aggtgctgga ggaggtggcc gacaagccac agactgagtt cctcatgaaa    720
tactgcctgg tgaccagcag gctacagaag atcctggcag aagcaccacc gcctgcccgt    780
ttggacatcc agctgcctgt catctcagat gacttcaaat tccaggtgtg gaggaagatg    840
ttccgggctc tgatgccagt tacaaaggag ctgacctttg acccgagctc tgcgcacccg    900
agcctggtgc tgtctccctc cggtcgccgc gtggagtgct cggaccagaa ggcgccgccg    960
```

-continued

```
gccggggagg atccgtgcca gttcgacaag gccgtggcgg tggtggcgca gcaggtgctg      1020
tccgacggcg agcactactg ggaggtgcag gtgggcgaga agccgcgctg ggccctcggc      1080
gtgatcgcgg cccaggccag ccgccgcggc cggctgcacg ccgtcccctc gcagggcctc      1140
tggctgctcg ggctgcggga cggcaagatc ctggaggcgc acgtcgaagc caaggagccg      1200
cgcgcgctgc gcaccccgga gaggcggccc acgcgcatcg ggatctacct aagcttcggc      1260 gacgagtcc  tctccttta  tgatgccagt  gaccccgacg  ccctcgagct  gctctttgcc    1320
ttccacgagc gcctgcccgg gcccgtgtac cccttcttcg acgtatgctg gcacgacaag      1380
ggcaaaaatg ctcagccgct gctgctggtg gggcctgatg gcgaggaggc ctga            1434
```

<210> SEQ ID NO 19
<211> LENGTH: 1434
<212> TYPE: DNA
<213> ORGANISM: Homo sapiens

<400> SEQUENCE: 19

```
atgtcggctg cgcccggcct cctgcaccag gagctgtcct gcccgctgtg cctgcagctg      60
ttcgacgcgc ccgtgacagc cgagtgcggc cacagtttct gccgcgcctg cctaggccgc      120
gtggccgggg agccggcggc ggatggcacc gttctctgcc cctgctgcca ggcccccacg      180
cggccgcagg cactcagcac caacctgcag ctggcgcgcc tggtggaggg gctgcccag      240 gtgccgcagg gccactgcga ggagcacctg gacccgctga gcatctactg cgagcaggac      300 cgcgcgctg  tgtgcggagt  gtgcgcctca  ctcggctcgc  accgcggtca  tcgcctcctg    360
cctgccgccg aggcccacgc acgcctcaag acacagctgc acagcagaa  actgcagctg      420 caggaggcat gcatgcgcaa ggagaagagt gtggctgtgc tggagcatca gctggtggag      480
gtggaggaga cagtgcgtca gttccggggg gccgtggggg agcagctggg caagatgcgg      540
gtgttcctgg ctgcactgga gggctccttg gaccgcgagg cagagcgtgt acggggtgag      600
gcaggggtcg ccttgcgccg ggagctgggg agcctgaact cttacctgga gcagctgcgg      660
cagatggaga aggtcctgga ggaggtggcg gacaagccgc agactgagtt cctcatgaaa      720
tactgcctgg tgaccagcag gctgcagaag atcctggcag agtctccccc acccgcccgt      780
ctggacatcc agctgccaat tatctcagat gacttcaaat tccaggtgtg gaggaagatg      840
ttccgggctc tgatgccagc gctggaggag ctgaccttg acccgagctc tgcgcacccg      900
agcctggtgg tgtcttcctc tggccgccgc gtggagtgct cggagcagaa ggcgccgccg      960
gccggggagg acccgcgcca gttcgacaag gcggtggcgg tggtggcgca ccagcagctc      1020
tccgagggcg agcactactg ggaggtggat gttggcgaca agccgcgctg ggcgctgggc      1080
gtgatcgcgg ccgaggcccc ccgccgcggg cgcctgcacg cggtgccctc gcagggcctg      1140
tggctgctgg ggctgcgcga gggcaagatc ctggaggcac acgtggaggc caaggagccg      1200
cgcgctctgc gcagccccga gaggcggccc acgcgcattg cctttacct  gagcttcggc      1260 gacggcgtcc tctccttcta cgatgccagc gacgccgacg cgctcgtgcc gctttttgcc      1320
ttccacgagc gcctgcccag gcccgtgtac cccttcttcg acgtgtgctg gcacgacaag      1380
ggcaagaatg cccagccgct gctgctcgtg ggtcccgaag gcgccgaggc ctga            1434
```

<210> SEQ ID NO 20
<211> LENGTH: 1434
<212> TYPE: DNA
<213> ORGANISM: Mus musculus

<400> SEQUENCE: 20

```
atgtcggctg cacccggcct tctgcgtcag gaactgtcct gcccactgtg cttgcagctg      60
ttcgatgcgc cagtgacggc tgagtgtggc cacagtttct gccgtgcctg cctgatccgg     120
gtggcagggg agcctgctgc ggacggcaca gttgcctgtc cctgttgtca ggcacctaca     180
cggccgcagg ctctaagcac taacctccag ttgtcacgcc ttgtggaggg tttggcgcaa     240
gtgcccaag gccactgcga ggaacacctg gatccactga gcatctactg cgagcaggac     300
cgcacacttg tgtgtggtgt gtgtgcctcg ctcggttctc accgtggtca tcgtctcctg     360
cctgccgctg aagcccaagc acgcctcaag acacagcttc cacagcagaa gatgcagctg     420
caggaggcat gcatgcgcaa ggagaagact gtagcggtgc tggagcatca gctggtggag     480
gtggaggaga cagtgcgcca gttccgggga gctgtcgggg agcagctggg gaagatgcgg     540
atgttcctgg ctgccctaga aagttctctg gaccgtgaag cagaaagggt tcggggtgat     600
gctggggttg ccttgcgtcg ggagctgtca agcctgaact cttacctaga gcaactgagg     660
cagatggaga aggtgctgga ggaggtggct gacaagccac agacagaatt cctcatgaaa     720
ttctgcctgg taaccagcag gctgcagaag atcctgtcag agtcaccacc accggcaagg     780
ctagatatcc agctgcctgt catctcagat gacttcaaat tccaggtgtg aagaagatg     840
ttccgggctc tgatgccagc gctggaggaa ctgacttttg accccagctc tgcgcacccg     900
agcctggtgg tgtcctcctc tggtcgccga gtggagtgct cagaccagaa ggcgccgcca     960
gcgggagaag acacgcgtca gttcgacaag gcagtagcgg tggtggcgca gcagctgctg    1020
tcacagggcg agcactattg ggaggtggag gtgggcgaca aaccacgctg ggccctggga    1080
gtgatggcgg ctgacgcttc ccgccgtggc cggctgcacg cggtgccctc acaggggctg    1140
tggctgctgg gtctgcgcga tggcaagatc ctggaggcgc acgtggaggc caaggagccg    1200
cgggcactgc gcaccccaga gaggcctccg gcgcgcattg gcctctacct aagcttcgca    1260
gatggcgtcc tggctttcta tgatgcgagc aaccccgacg tacttacgcc aatctttttct    1320
ttccacgagc gtctgcccgg gccggtgtac cccatctttg acgtgtgctg gcacgacaag    1380
ggcaagaatg cccagcccct gctgcttgtg gggccggagc aggaacaggc ctga          1434
```

<210> SEQ ID NO 21  
<211> LENGTH: 1434  
<212> TYPE: DNA  
<213> ORGANISM: Rattus norvegicus

<400> SEQUENCE: 21

```
atgtcgactg caccaggcct tttgcgccag gaactgtctt gcccgctgtg cttgcagctg      60
ttcgatgcac cagtgaccgc tgagtgtggc cacagtttct gccgtgcctg cctgatccgt     120
gtggcagggg agcctgccga cgatggcacg gttgcctgtc cctgttgtca ggcatctact     180
cggccacagg cgctaagcac taacctccag ttggcacgcc ttgtggaggg tttggcacaa     240
gtgcccaag gccactgcga ggaacacctg gatccactga gcatctactg cgagcaggac     300
cgcacacttg tgtgtggtgt gtgtgcctct ctcggttcac accgtggtca ccgtcttctg     360
cctgccgcag aagcccatgc acgtctcaag acacagcttc cacaacagaa ggcccagctg     420
caggaggcat gcatgcgcaa ggagaagagt gtagcagtcc tggagcatca gctggtggag     480
gtggaggaga ccgtcgtca gttccgggga gctgttgggg agcagctggg gaagatgcgg     540
atgttcctgg ctgccctaga aagttctttg gaccgtgaag cagaaagggt tcgaggtgag     600
gcaggggttg ccttgcggcg ggagctgtca agcctgaact cttacctgga gcaactgagg     660
```

```
cagatggaga aggtgctgga ggaggtggct gacaagccac agacagaatt cctcatgaaa      720
ttctgcctgg tgaccagcag gctgcagaag attctgtcag agtcaccacc cccagcaagg      780
ctagatatcc agctgcctgt catctcagat gacttcaaat tccaggtgtg aagaagatg       840 ttccgggctc tgatgccaga gttggaggaa ctgacttttg accccagctc tgcgcacccg      900
agcctggtgg tgtccgcctc tggtcgccga gtggagtgct cggagcagaa ggcgccgcca      960
gcaggagaag acacgtgcca gttcgacaag acggtagcgg tagtggcgaa gcagctgctg     1020 tcacagggg agcactactg ggaggtggag gtgggcgaca agccacgctg ggccctgggt      1080
gtgatgcgct gacgcttc ccgtcgtggc cgcctgcacg cggtgccctc acaggggctg       1140
tggttgctcg gcctgcgcga tgcaagatc ctggaggcac acgtggaggc caaggagcca      1200
cgggcactgc gcaccccaga gaggccacca gcgcgcattg gcctctacct aagctttgca     1260
gatggcgtcc tgactttcta tgatgcaagc aacaccgacg cgcttacacc gctctttcct     1320
tttcatgagc gtctgcctgg gccggtgtac cccatgtttg acgtgtgctg gcacgacaag     1380
ggcaagaatt ctcagccgct gttgctcgtg gggccagaca gtgagcaggc ctga           1434
```

<210> SEQ ID NO 22
<211> LENGTH: 1434
<212> TYPE: DNA
<213> ORGANISM: Macaca fascicularis

<400> SEQUENCE: 22

```
atgtcggctg cgccgggcct cctgcaccag gagctgtcct gcccgctgtg cctgcagctg       60
ttcgacgcgc ccgtgacagc cgagtgcggc cacagtttct gtcgcgcctg cctgggccgc      120
gtggccgggg aaccgcggc ggatggcacc gttctctgcc cctgctgtca ggcccccacg       180
cggccgcagg cactcagcac caacctgcag ctggcgcgcc tggtggaggg gctggcccag      240
gtgccgcagg gccactgcga ggagcacctg accccgctga gcatctactg tgagcaggac      300
cgcgcgctgg tgtgcggagt gtgcgcctca ctcggctcgc accgcggtca tcgcctgctg      360
cccgccgccg aggcccacgc acgcctcaag acgcagctgc acagcagaa actgcagctg       420 caggaggcat gcatgcgcaa ggagaagagt gtagctgtgc tggagcatca gttggtggaa      480
gtggaggaga cagtgcgtca gttccggggg gccgtggggg agcagctggg caagatgcgg      540
gtgttcctgg ctgcactgga gggctccttg accgtgagg cagagcgtgt gcggggtgag       600 gcagggtcg ccttgcgccg ggagctgggg agcctgaact cttacctgga gcagctgcgg       660
cagatggaga aggtgctgga ggaggtggcc gacaagccgc agactgagtt cctaatgaaa      720
tactgcctgg tgaccagcag gctgcagaag atcctggcag agtctccccc acccgcccgt      780
ctggacatcc agctgccaat catctcagat gacttcaaat tccaggtgtg aggaagatg       840 ttccgggctc tgatgccagc gctggaggag ctgacctttg acccgagctc tgcgcacccc      900
agcctggtgg tgtcttcctc cggcgccgcg gtggagtgct cggagcagaa ggcgccgccg      960 gcggggagg acccgcgcca gttcgacaag gcggtagcgg tggtggcgca ccagcagctc     1020
tccgagggcg aacactactg ggaggtggag gtgggcgaca agccgcgctg ggcgctgggt     1080
gtgatcgcgc cgaggggcc ccgtcgcggg cgcctgcacg cggtgccctc gcagggcctg      1140
tggctgctgg ggctgcgtga ggcaagatc ctggaggctc acgtggaggc caaggagccg      1200
cgcgctctgc gcagccccga gcggcggccc acgcgcatcg gcctctacct gagcttcggc     1260
gacggcgtcc tctccttcta cgatgccagc gacgccgacg cgctcgtgcc gcttttgcc      1320
```

-continued

| | |
|---|---|
| ttccacgagc gcctgcctgg gcccgtgtac cccttcttcg acgtgtgctg gcacgacaag | 1380 |
| ggcaagaact cccagccgct gctgctcgtg gggtccgaag gcgccgaagc ctga | 1434 |

<210> SEQ ID NO 23
<211> LENGTH: 1437
<212> TYPE: DNA
<213> ORGANISM: Sus scrofa

<400> SEQUENCE: 23

| | |
|---|---|
| atgtcagctg cgcccggcct cctgcaccag gagctgtcct gtccgctgtg cctgcagctg | 60 |
| ttcgatgcgc cggtgacggc tgagtgcggc cacagcttct gccgcgcctg cctgggccgc | 120 |
| gtggcagggg agccagccgc ggatggcacg gtgctctgcc ccagctgcca ggcacccacg | 180 |
| cggccgcagg cgctcagcac caaccagcag ctggcgcgcc tggtggaggg gctggcgcag | 240 |
| gtgccgcagg gccactgcga ggagcaccta gacccgctca gcatctactg cgagcaggac | 300 |
| cgcgtgctcg tgtgcggcgt ctgcgcctcg ctgggttcgc accgcggcca ccgcctgctg | 360 |
| cccgccgccg aagcccatgc gcgccttaag acgcagctcc gcagcagaa gctgcagctg | 420 |
| caggaggcgt gtatgcggaa ggagaagagc gtgggtgtgc tggagcaaca actggtggaa | 480 |
| gtggaggaga cggtgcgtca gttccggggg gcagtggggg agcagctggg caagatgcgg | 540 |
| ttgttcctgg ctgcactgga gggctccttg gaccgagaag cagagcgtgt gcggggtgag | 600 |
| gcggggtcg ccttgcggag ggagctgggg agcctgaagt cttacttgga gcagctgcgg | 660 |
| cagatggaga aggtgctgga ggaggtggca gacaagcccc agaccgagtt cctcatgaaa | 720 |
| tactgcctgt tgaccagcag gctgcagaag atcctggcag agtcgccccc acctgcccgc | 780 |
| ctggacattc agctgcctgt catctcagac gacttcaaat tccaggtgtg gagaaagatg | 840 |
| ttcccgggccc tgatgccagc gatgcaggag ctgacctttg accccagcac ggcccacccg | 900 |
| agcctggtgc tgtcggcctc gggccgccgc gtggagtgct cggagcagaa ggcgccgccg | 960 |
| gccgagagg acccgcgcca gttcgacaag gcggtggcgg tggtgacgca ccagctgctg | 1020 |
| tcggaaggcg agcactactg ggaggtggag gtgggcgaca agccacgctg ggcgctgggc | 1080 |
| gtgatcgggg cccaggccgg tcgccgcggc cggctgcacg ccgtgccctc gcagggcctc | 1140 |
| tggctgctcg ggctgcgcga gggcaagatc ctggaggctc acgtcgaggc caaggagccg | 1200 |
| cgcgccctgc gcaccccgga gaggcggccg tcgcgcatcg ggatctacct gagcttcgcg | 1260 |
| gatggcgtcc tctcgttcta cgacgccagc gacgccgacg cgctggagct gctcttcgcc | 1320 |
| ttccacgaac gcctgccggg ccccgtgtac cccttcttcg acgtgtgctg gcacgacaag | 1380 |
| ggcaagaacg ctcagccgct cctgctggtg gggcccgaca gcggcgggga ggcctga | 1437 |

<210> SEQ ID NO 24
<211> LENGTH: 1434
<212> TYPE: DNA
<213> ORGANISM: Canis lupus familiaris

<400> SEQUENCE: 24

| | |
|---|---|
| atgtcggccg cgccgggcct cctgcaccag gagctgtcct gcccgctctg cctgcagctg | 60 |
| tttgacgcgc cggtgaccgc cgagtgcggc cacagtttct gccgcgcctg cctgagccgc | 120 |
| gtggctgggg agccggcggc ggacggcacc gtgccctgcc cgtgctgcca ggcactcacg | 180 |
| cggccacagg cgctcagcac caaccagcag ctggcgcgcc tggtggaggg gctggcgcag | 240 |
| gtgccgcagg gccactgcga ggagcaccta gacccgctca gcatctactg cgagcaggat | 300 |
| cgagcgctcg tgtgcggcgt gtgcgcctcg ctcggctcgc accgcggcca ccgcctgctg | 360 |

```
cccgccgccg aagcccacgc gcgcctcaag acacagctgc cacagcagaa actgcagctg    420
caggaggcat gtatgcgcaa ggagaagagt gtggctctgc tggagcatca gctcatggaa    480
gtggaggaga tggtgcgtca gttccggggg gctgtagggg agcagctggg caagatgcgg    540
gtgttcctgg ctgcactgga gggctccttg gaccgtgagg cagagcgcgt gcggggagag    600
gcaggggttg ccctgcggcg ggagctgggg agcctgaact cttacctgga gcagttgcgt    660
cagatgagaa aggtgctgga ggaggtggcc gacaagccac agactgagtt cctcatgaaa    720
tactgcctgg tgaccagcag gctacagaag atcctggcag aatcaccacc gcctgcccgt    780
ttggacatcc agctgcctgt catctcagat gacttcaaat ccaggtgtg gaggaagatg    840 ttccgggctc tgatgccagt tacaaaggag ctgacctttg acccgagctc tgcgcacccg    900
agcctggtgc tgtctccctc cggtcgccgc gtggagtgct cggaccagaa ggcgccgccg    960
gccggggagg atccgtgcca gttcgacaag gccgtggcgg tggtggcgca gcaggtgctg   1020
tccgacggcg agcactactg ggaggtgcag gtgggcgaga agccgcgctg ggccctcggc   1080
gtgatcgcgg cccaggccag ccgccgcggc cggctgcacg ccgtcccctc gcagggcctc   1140
tggctgctcg gcctgcggga cggcaagatc ctggaggcgc acgtcgaagc caaggagccg   1200
cgcgcgctgc gcaccccgga gaggcggccc acgcgcatcg ggatctacct aagcttcggc   1260
gacggagtcc tctccttta tgatgccagt gaccccgacg ccctgagctg ctctttgcc    1320 ttccacgagc gcctgcccgg gccgtgtac cccttcttcg acgtatgctg gcacgacaag   1380
ggcaaaaatg ctcagccgct gctgctggtg gggcctgatg gcgaggaggc ctga        1434

<210> SEQ ID NO 25
<211> LENGTH: 33
<212> TYPE: DNA
<213> ORGANISM: Artificial Sequence
<220> FEATURE:
<223> OTHER INFORMATION: Forward primer of human MG53 S255A mutant

<400> SEQUENCE: 25
tgcagaagat cctggcagag gctcccccac ccg                                33

<210> SEQ ID NO 26
<211> LENGTH: 33
<212> TYPE: DNA
<213> ORGANISM: Artificial Sequence
<220> FEATURE:
<223> OTHER INFORMATION: Reverse primer of human MG53 S255A mutant

<400> SEQUENCE: 26
tccagacggg cgggtggggg agcctctgcc agg                                33

<210> SEQ ID NO 27
<211> LENGTH: 33
<212> TYPE: DNA
<213> ORGANISM: Artificial Sequence
<220> FEATURE:
<223> OTHER INFORMATION: Forward primer of human MG53 S255G mutant

<400> SEQUENCE: 27
tgcagaagat cctggcagag ggtcccccac ccg                                33

<210> SEQ ID NO 28
<211> LENGTH: 33
<212> TYPE: DNA
<213> ORGANISM: Artificial Sequence
<220> FEATURE:
```

<223> OTHER INFORMATION: Reverse primer of human MG53 S255G mutant

<400> SEQUENCE: 28
tccagacggg cgggtggggg accctctgcc agg                                    33

<210> SEQ ID NO 29
<211> LENGTH: 33
<212> TYPE: DNA
<213> ORGANISM: Artificial Sequence
<220> FEATURE:
<223> OTHER INFORMATION: Forward primer of human MG53 S255L mutant

<400> SEQUENCE: 29
tgcagaagat cctggcagag cttcccccac ccg                                    33

<210> SEQ ID NO 30
<211> LENGTH: 33
<212> TYPE: DNA
<213> ORGANISM: Artificial Sequence
<220> FEATURE:
<223> OTHER INFORMATION: Reverse primer of human MG53 S255L mutant

<400> SEQUENCE: 30
tccagacggg cgggtggggg aagctctgcc agg                                    33

<210> SEQ ID NO 31
<211> LENGTH: 33
<212> TYPE: DNA
<213> ORGANISM: Artificial Sequence
<220> FEATURE:
<223> OTHER INFORMATION: Forward primer of human MG53 S255V mutant

<400> SEQUENCE: 31
tgcagaagat cctggcagag gttcccccac ccg                                    33

<210> SEQ ID NO 32
<211> LENGTH: 33
<212> TYPE: DNA
<213> ORGANISM: Artificial Sequence
<220> FEATURE:
<223> OTHER INFORMATION: Reverse primer of human MG53 S255V mutant

<400> SEQUENCE: 32
tccagacggg cgggtggggg aacctctgcc agg                                    33

<210> SEQ ID NO 33
<211> LENGTH: 33
<212> TYPE: DNA
<213> ORGANISM: Artificial Sequence
<220> FEATURE:
<223> OTHER INFORMATION: Forward primer of human MG53 S255P mutant

<400> SEQUENCE: 33
tgcagaagat cctggcagag cctcccccac ccg                                    33

<210> SEQ ID NO 34
<211> LENGTH: 33
<212> TYPE: DNA
<213> ORGANISM: Artificial Sequence
<220> FEATURE:
<223> OTHER INFORMATION: Reverse primer of human MG53 S255P mutant

<400> SEQUENCE: 34
tccagacggg cgggtggggg aggctctgcc agg                                    33

```
<210> SEQ ID NO 35
<211> LENGTH: 33
<212> TYPE: DNA
<213> ORGANISM: Artificial Sequence
<220> FEATURE:
<223> OTHER INFORMATION: Forward primer of human MG53 S255F mutant

<400> SEQUENCE: 35
tgcagaagat cctggcagag tttcccccac ccg                                    33

<210> SEQ ID NO 36
<211> LENGTH: 33
<212> TYPE: DNA
<213> ORGANISM: Artificial Sequence
<220> FEATURE:
<223> OTHER INFORMATION: Reverse primer of human MG53 S255F mutant

<400> SEQUENCE: 36
tccagacggg cgggtggggg aaactctgcc agg                                    33

<210> SEQ ID NO 37
<211> LENGTH: 33
<212> TYPE: DNA
<213> ORGANISM: Artificial Sequence
<220> FEATURE:
<223> OTHER INFORMATION: Forward primer of human MG53 S255W mutant

<400> SEQUENCE: 37
tgcagaagat cctggcagag tggcccccac ccg                                    33

<210> SEQ ID NO 38
<211> LENGTH: 33
<212> TYPE: DNA
<213> ORGANISM: Artificial Sequence
<220> FEATURE:
<223> OTHER INFORMATION: Reverse primer of human MG53 S255W mutant

<400> SEQUENCE: 38
tccagacggg cgggtggggg ccactctgcc agg                                    33

<210> SEQ ID NO 39
<211> LENGTH: 33
<212> TYPE: DNA
<213> ORGANISM: Artificial Sequence
<220> FEATURE:
<223> OTHER INFORMATION: Forward primer of human MG53 S255Q mutant

<400> SEQUENCE: 39
tgcagaagat cctggcagag caacccccac ccg                                    33

<210> SEQ ID NO 40
<211> LENGTH: 33
<212> TYPE: DNA
<213> ORGANISM: Artificial Sequence
<220> FEATURE:
<223> OTHER INFORMATION: Reverse primer of human MG53 S255Q mutant

<400> SEQUENCE: 40
tccagacggg cgggtggggg ttgctctgcc agg                                    33

<210> SEQ ID NO 41
<211> LENGTH: 33
<212> TYPE: DNA
<213> ORGANISM: Artificial Sequence
<220> FEATURE:
<223> OTHER INFORMATION: Forward primer of human MG53 S255C mutant
```

<400> SEQUENCE: 41
tgcagaagat cctggcagag tgtcccccac ccg					33

<210> SEQ ID NO 42
<211> LENGTH: 33
<212> TYPE: DNA
<213> ORGANISM: Artificial Sequence
<220> FEATURE:
<223> OTHER INFORMATION: Reverse primer of human MG53 S255C mutant

<400> SEQUENCE: 42
tccagacggg cgggtggggg acactctgcc agg					33

<210> SEQ ID NO 43
<211> LENGTH: 33
<212> TYPE: DNA
<213> ORGANISM: Artificial Sequence
<220> FEATURE:
<223> OTHER INFORMATION: Forward primer of human MG53 S255Y mutant

<400> SEQUENCE: 43
tgcagaagat cctggcagag tatcccccac ccg					33

<210> SEQ ID NO 44
<211> LENGTH: 33
<212> TYPE: DNA
<213> ORGANISM: Artificial Sequence
<220> FEATURE:
<223> OTHER INFORMATION: Reverse primer of human MG53 S255Y mutant

<400> SEQUENCE: 44
tccagacggg cgggtggggg atactctgcc agg					33

<210> SEQ ID NO 45
<211> LENGTH: 33
<212> TYPE: DNA
<213> ORGANISM: Artificial Sequence
<220> FEATURE:
<223> OTHER INFORMATION: Forward primer of human MG53 S255D mutant

<400> SEQUENCE: 45
tgcagaagat cctggcagag gatcccccac ccg					33

<210> SEQ ID NO 46
<211> LENGTH: 33
<212> TYPE: DNA
<213> ORGANISM: Artificial Sequence
<220> FEATURE:
<223> OTHER INFORMATION: Reverse primer of human MG53 S255D mutant

<400> SEQUENCE: 46
tccagacggg cgggtggggg ctactctgcc agg					33

<210> SEQ ID NO 47
<211> LENGTH: 33
<212> TYPE: DNA
<213> ORGANISM: Artificial Sequence
<220> FEATURE:
<223> OTHER INFORMATION: Forward primer of human MG53 S255R mutant

<400> SEQUENCE: 47
tgcagaagat cctggcagag cgtcccccac ccg					33

<210> SEQ ID NO 48
<211> LENGTH: 33

```
<212> TYPE: DNA
<213> ORGANISM: Artificial Sequence
<220> FEATURE:
<223> OTHER INFORMATION: Reverse primer of human MG53 S255R mutant

<400> SEQUENCE: 48
tccagacggg cgggtggggg acgctctgcc agg                                   33

<210> SEQ ID NO 49
<211> LENGTH: 33
<212> TYPE: DNA
<213> ORGANISM: Artificial Sequence
<220> FEATURE:
<223> OTHER INFORMATION: Forward primer of human MG53 S211A mutant

<400> SEQUENCE: 49
ccttgcgccg ggagctgggg gccctgaact ctt                                   33

<210> SEQ ID NO 50
<211> LENGTH: 35
<212> TYPE: DNA
<213> ORGANISM: Artificial Sequence
<220> FEATURE:
<223> OTHER INFORMATION: Reverse primer of human MG53 S211A mutant

<400> SEQUENCE: 50
gctgctccag gtaagagttc agggccccca gctcc                                 35

<210> SEQ ID NO 51
<211> LENGTH: 33
<212> TYPE: DNA
<213> ORGANISM: Artificial Sequence
<220> FEATURE:
<223> OTHER INFORMATION: Forward primer of human MG53 S214A mutant

<400> SEQUENCE: 51
gggagctggg gagcctgaac gcttacctgg agc                                   33

<210> SEQ ID NO 52
<211> LENGTH: 33
<212> TYPE: DNA
<213> ORGANISM: Artificial Sequence
<220> FEATURE:
<223> OTHER INFORMATION: Reverse primer of human MG53 S214A mutant

<400> SEQUENCE: 52
tgccgcagct gctccaggta agcgttcagg ctc                                   33

<210> SEQ ID NO 53
<211> LENGTH: 33
<212> TYPE: DNA
<213> ORGANISM: Artificial Sequence
<220> FEATURE:
<223> OTHER INFORMATION: Forward primer of human MG53 S246A mutant

<400> SEQUENCE: 53
tgaaatactg cctggtgacc gccaggctgc aga                                   33

<210> SEQ ID NO 54
<211> LENGTH: 33
<212> TYPE: DNA
<213> ORGANISM: Artificial Sequence
<220> FEATURE:
<223> OTHER INFORMATION: Reverse primer of human MG53 S246A mutant

<400> SEQUENCE: 54
```

```
gccaggatct tctgcagcct ggcggtcacc agg                                33
```

<210> SEQ ID NO 55
<211> LENGTH: 33
<212> TYPE: DNA
<213> ORGANISM: Artificial Sequence
<220> FEATURE:
<223> OTHER INFORMATION: Forward primer of human MG53 S269A mutant

<400> SEQUENCE: 55

```
aggagctgac ctttgacccg gcctctgcgc acc                                33
```

<210> SEQ ID NO 56
<211> LENGTH: 33
<212> TYPE: DNA
<213> ORGANISM: Artificial Sequence
<220> FEATURE:
<223> OTHER INFORMATION: Reverse primer of human MG53 S296A mutant

<400> SEQUENCE: 56

```
accaggctcg ggtgcgcaga ggccgggtca aag                                33
```

<210> SEQ ID NO 57
<211> LENGTH: 33
<212> TYPE: DNA
<213> ORGANISM: Artificial Sequence
<220> FEATURE:
<223> OTHER INFORMATION: Forward primer of human MG53 S297A mutant

<400> SEQUENCE: 57

```
agctgacctt tgacccgagc gctgcgcacc cga                                33
```

<210> SEQ ID NO 58
<211> LENGTH: 33
<212> TYPE: DNA
<213> ORGANISM: Artificial Sequence
<220> FEATURE:
<223> OTHER INFORMATION: Reverse primer of human MG53 S297A mutant

<400> SEQUENCE: 58

```
accaccaggc tcgggtgcgc agcgctcggg tca                                33
```

<210> SEQ ID NO 59
<211> LENGTH: 33
<212> TYPE: DNA
<213> ORGANISM: Artificial Sequence
<220> FEATURE:
<223> OTHER INFORMATION: Forward primer of mouse MG53 S255A mutant

<400> SEQUENCE: 59

```
tgcagaagat cctgtcagag gcaccaccac cgg                                33
```

<210> SEQ ID NO 60
<211> LENGTH: 33
<212> TYPE: DNA
<213> ORGANISM: Artificial Sequence
<220> FEATURE:
<223> OTHER INFORMATION: Reverse primer of mouse MG53 S255A mutant

<400> SEQUENCE: 60

```
tctagccttg ccggtggtgg tgcctctgac agg                                33
```

<210> SEQ ID NO 61
<211> LENGTH: 33
<212> TYPE: DNA
<213> ORGANISM: Artificial Sequence
<220> FEATURE:
<223> OTHER INFORMATION: Forward primer of mouse MG53 S255G mutant

<400> SEQUENCE: 61
tgcagaagat cctgtcagag ggaccaccac cgg         33

<210> SEQ ID NO 62
<211> LENGTH: 33
<212> TYPE: DNA
<213> ORGANISM: Artificial Sequence
<220> FEATURE:
<223> OTHER INFORMATION: Reverse primer of mouse MG53 S255G mutant

<400> SEQUENCE: 62
tctagccttg ccggtggtgg tccctctgac agg         33

<210> SEQ ID NO 63
<211> LENGTH: 33
<212> TYPE: DNA
<213> ORGANISM: Artificial Sequence
<220> FEATURE:
<223> OTHER INFORMATION: Forward primer of mouse MG53 S255L mutant

<400> SEQUENCE: 63
tgcagaagat cctgtcagag ttaccaccac cgg         33

<210> SEQ ID NO 64
<211> LENGTH: 33
<212> TYPE: DNA
<213> ORGANISM: Artificial Sequence
<220> FEATURE:
<223> OTHER INFORMATION: Reverse primer of mouse MG53 S255L mutant

<400> SEQUENCE: 64
tctagccttg ccggtggtgg taactctgac agg         33

<210> SEQ ID NO 65
<211> LENGTH: 33
<212> TYPE: DNA
<213> ORGANISM: Artificial Sequence
<220> FEATURE:
<223> OTHER INFORMATION: Forward primer of mouse MG53 S255W mutant

<400> SEQUENCE: 65
tgcagaagat cctgtcagag tggccaccac cgg         33

<210> SEQ ID NO 66
<211> LENGTH: 33
<212> TYPE: DNA
<213> ORGANISM: Artificial Sequence
<220> FEATURE:
<223> OTHER INFORMATION: Reverse primer of mouse MG53 S255W mutant

<400> SEQUENCE: 66
tctagccttg ccggtggtgg ccactctgac agg         33

<210> SEQ ID NO 67
<211> LENGTH: 33
<212> TYPE: DNA
<213> ORGANISM: Artificial Sequence
<220> FEATURE:
<223> OTHER INFORMATION: Forward primer of mouse MG53 S255Q mutant

<400> SEQUENCE: 67
tgcagaagat cctgtcagag caaccaccac cgg         33

```
<210> SEQ ID NO 68
<211> LENGTH: 33
<212> TYPE: DNA
<213> ORGANISM: Artificial Sequence
<220> FEATURE:
<223> OTHER INFORMATION: Reverse primer of mouse MG53 S255Q mutant

<400> SEQUENCE: 68
tctagccttg ccggtggtgg ttgctctgac agg                                     33

<210> SEQ ID NO 69
<211> LENGTH: 33
<212> TYPE: DNA
<213> ORGANISM: Artificial Sequence
<220> FEATURE:
<223> OTHER INFORMATION: Forward primer of mouse MG53 S255Y mutant

<400> SEQUENCE: 69
tgcagaagat cctgtcagag tatccaccac cgg                                     33

<210> SEQ ID NO 70
<211> LENGTH: 33
<212> TYPE: DNA
<213> ORGANISM: Artificial Sequence
<220> FEATURE:
<223> OTHER INFORMATION: Reverse primer of mouse MG53 S255Y mutant

<400> SEQUENCE: 70
tctagccttg ccggtggtgg atactctgac agg                                     33

<210> SEQ ID NO 71
<211> LENGTH: 33
<212> TYPE: DNA
<213> ORGANISM: Artificial Sequence
<220> FEATURE:
<223> OTHER INFORMATION: Forward primer of mouse MG53 S255D mutant

<400> SEQUENCE: 71
tgcagaagat cctgtcagag gatccaccac cgg                                     33

<210> SEQ ID NO 72
<211> LENGTH: 33
<212> TYPE: DNA
<213> ORGANISM: Artificial Sequence
<220> FEATURE:
<223> OTHER INFORMATION: Reverse primer of mouse MG53 S255D mutant

<400> SEQUENCE: 72
tctagccttg ccggtggtgg atcctctgac agg                                     33

<210> SEQ ID NO 73
<211> LENGTH: 33
<212> TYPE: DNA
<213> ORGANISM: Artificial Sequence
<220> FEATURE:
<223> OTHER INFORMATION: Forward primer of mouse MG53 S255R mutant

<400> SEQUENCE: 73
tgcagaagat cctgtcagag cgaccaccac cgg                                     33

<210> SEQ ID NO 74
<211> LENGTH: 33
<212> TYPE: DNA
<213> ORGANISM: Artificial Sequence
<220> FEATURE:
<223> OTHER INFORMATION: Reverse primer of mouse MG53 S255R mutant
```

<400> SEQUENCE: 74
tctagccttg ccggtggtgg tcgctctgac agg                                         33

<210> SEQ ID NO 75
<211> LENGTH: 33
<212> TYPE: DNA
<213> ORGANISM: Artificial Sequence
<220> FEATURE:
<223> OTHER INFORMATION: Forward primer of rat MG53 S255A mutant

<400> SEQUENCE: 75
tgcagaagat tctgtcagag gcaccacccc cag                                         33

<210> SEQ ID NO 76
<211> LENGTH: 33
<212> TYPE: DNA
<213> ORGANISM: Artificial Sequence
<220> FEATURE:
<223> OTHER INFORMATION: Reverse primer of rat MG53 S255A mutant

<400> SEQUENCE: 76
tctagccttg ctgggggtgg tgcctctgac aga                                         33

<210> SEQ ID NO 77
<211> LENGTH: 33
<212> TYPE: DNA
<213> ORGANISM: Artificial Sequence
<220> FEATURE:
<223> OTHER INFORMATION: Forward primer of rat MG53 S255G mutant

<400> SEQUENCE: 77
tgcagaagat tctgtcagag ggaccacccc cag                                         33

<210> SEQ ID NO 78
<211> LENGTH: 33
<212> TYPE: DNA
<213> ORGANISM: Artificial Sequence
<220> FEATURE:
<223> OTHER INFORMATION: Reverse primer of rat MG53 S255G mutant

<400> SEQUENCE: 78
tctagccttg ctgggggtgg tccctctgac aga                                         33

<210> SEQ ID NO 79
<211> LENGTH: 33
<212> TYPE: DNA
<213> ORGANISM: Artificial Sequence
<220> FEATURE:
<223> OTHER INFORMATION: Forward primer of rat MG53 S255L mutant

<400> SEQUENCE: 79
tgcagaagat tctgtcagag ttaccacccc cag                                         33

<210> SEQ ID NO 80
<211> LENGTH: 33
<212> TYPE: DNA
<213> ORGANISM: Artificial Sequence
<220> FEATURE:
<223> OTHER INFORMATION: Reverse primer of rat MG53 S255L mutant

<400> SEQUENCE: 80
tctagccttg ctgggggtgg taactctgac aga                                         33

<210> SEQ ID NO 81

```
<211> LENGTH: 33
<212> TYPE: DNA
<213> ORGANISM: Artificial Sequence
<220> FEATURE:
<223> OTHER INFORMATION: Forward primer of rat MG53 S255W mutant

<400> SEQUENCE: 81
tgcagaagat tctgtcagag tggccacccc cag                                   33

<210> SEQ ID NO 82
<211> LENGTH: 33
<212> TYPE: DNA
<213> ORGANISM: Artificial Sequence
<220> FEATURE:
<223> OTHER INFORMATION: Reverse primer of rat MG53 S255W mutant

<400> SEQUENCE: 82
tctagccttg ctgggggtgg ccactctgac aga                                   33

<210> SEQ ID NO 83
<211> LENGTH: 33
<212> TYPE: DNA
<213> ORGANISM: Artificial Sequence
<220> FEATURE:
<223> OTHER INFORMATION: Forward primer of rat MG53 S255Q mutant

<400> SEQUENCE: 83
tgcagaagat tctgtcagag caaccacccc cag                                   33

<210> SEQ ID NO 84
<211> LENGTH: 33
<212> TYPE: DNA
<213> ORGANISM: Artificial Sequence
<220> FEATURE:
<223> OTHER INFORMATION: Reverse primer of rat MG53 S255Q mutant

<400> SEQUENCE: 84
tctagccttg ctgggggtgg ttgctctgac aga                                   33

<210> SEQ ID NO 85
<211> LENGTH: 33
<212> TYPE: DNA
<213> ORGANISM: Artificial Sequence
<220> FEATURE:
<223> OTHER INFORMATION: Forward primer of rat MG53 S255Y mutant

<400> SEQUENCE: 85
tgcagaagat tctgtcagag tatccacccc cag                                   33

<210> SEQ ID NO 86
<211> LENGTH: 33
<212> TYPE: DNA
<213> ORGANISM: Artificial Sequence
<220> FEATURE:
<223> OTHER INFORMATION: Reverse primer of rat MG53 S255Y mutant

<400> SEQUENCE: 86
tctagccttg ctgggggtgg atactctgac aga                                   33

<210> SEQ ID NO 87
<211> LENGTH: 33
<212> TYPE: DNA
<213> ORGANISM: Artificial Sequence
<220> FEATURE:
<223> OTHER INFORMATION: Forward primer of rat MG53 S255D mutant

<400> SEQUENCE: 87
```
tgcagaagat tctgtcagag gatccacccc cag                                    33

<210> SEQ ID NO 88
<211> LENGTH: 33
<212> TYPE: DNA
<213> ORGANISM: Artificial Sequence
<220> FEATURE:
<223> OTHER INFORMATION: Reverse primer of rat MG53 S255D mutant

<400> SEQUENCE: 88
tctagccttg ctgggggtgg atcctctgac aga                                    33

<210> SEQ ID NO 89
<211> LENGTH: 33
<212> TYPE: DNA
<213> ORGANISM: Artificial Sequence
<220> FEATURE:
<223> OTHER INFORMATION: Forward primer of rat MG53 S255R mutant

<400> SEQUENCE: 89
tgcagaagat tctgtcagag cgaccacccc cag                                    33

<210> SEQ ID NO 90
<211> LENGTH: 33
<212> TYPE: DNA
<213> ORGANISM: Artificial Sequence
<220> FEATURE:
<223> OTHER INFORMATION: Reverse primer of rat MG53 S255R mutant

<400> SEQUENCE: 90
tctagccttg ctgggggtgg tcgctctgac aga                                    33

<210> SEQ ID NO 91
<211> LENGTH: 36
<212> TYPE: DNA
<213> ORGANISM: Artificial Sequence
<220> FEATURE:
<223> OTHER INFORMATION: Forward primer of monkey MG53 S255A mutant

<400> SEQUENCE: 91
aagatcctgg cagaggctcc cccacccgcc cgtctg                                 36

<210> SEQ ID NO 92
<211> LENGTH: 36
<212> TYPE: DNA
<213> ORGANISM: Artificial Sequence
<220> FEATURE:
<223> OTHER INFORMATION: Reverse primer of monkey MG53 S255A mutant

<400> SEQUENCE: 92
cagacgggcg ggtgggggag cctctgccag gatctt                                 36

<210> SEQ ID NO 93
<211> LENGTH: 37
<212> TYPE: DNA
<213> ORGANISM: Artificial Sequence
<220> FEATURE:
<223> OTHER INFORMATION: Forward primer of monkey MG53 S255G mutant

<400> SEQUENCE: 93
aagatcctgg cagagggtcc cccacccgcc cgtctgg                                37

<210> SEQ ID NO 94
<211> LENGTH: 37
<212> TYPE: DNA

```
<213> ORGANISM: Artificial Sequence
<220> FEATURE:
<223> OTHER INFORMATION: Reverse primer of monkey MG53 S255G mutant

<400> SEQUENCE: 94
ccagacgggc gggtgggGga ccctctgcca ggatctt                              37

<210> SEQ ID NO 95
<211> LENGTH: 37
<212> TYPE: DNA
<213> ORGANISM: Artificial Sequence
<220> FEATURE:
<223> OTHER INFORMATION: Forward primer of monkey MG53 S255L mutant

<400> SEQUENCE: 95
agatcctggc agagttaccc ccacccgccc gtctgga                              37

<210> SEQ ID NO 96
<211> LENGTH: 37
<212> TYPE: DNA
<213> ORGANISM: Artificial Sequence
<220> FEATURE:
<223> OTHER INFORMATION: Reverse primer of monkey MG53 S255L mutant

<400> SEQUENCE: 96
tccagacggg cgggtggggg taactctgcc aggatct                              37

<210> SEQ ID NO 97
<211> LENGTH: 37
<212> TYPE: DNA
<213> ORGANISM: Artificial Sequence
<220> FEATURE:
<223> OTHER INFORMATION: Forward primer of monkey MG53 S255W mutant

<400> SEQUENCE: 97
agatcctggc agagtggccc ccacccgccc gtctgga                              37

<210> SEQ ID NO 98
<211> LENGTH: 37
<212> TYPE: DNA
<213> ORGANISM: Artificial Sequence
<220> FEATURE:
<223> OTHER INFORMATION: Reverse primer of monkey MG53 S255W mutant

<400> SEQUENCE: 98
tccagacggg cgggtggggg ccactctgcc aggatct                              37

<210> SEQ ID NO 99
<211> LENGTH: 38
<212> TYPE: DNA
<213> ORGANISM: Artificial Sequence
<220> FEATURE:
<223> OTHER INFORMATION: Forward primer of monkey MG53 S255Q mutant

<400> SEQUENCE: 99
aagatcctgg cagagcaacc cccacccgcc cgtctgga                             38

<210> SEQ ID NO 100
<211> LENGTH: 38
<212> TYPE: DNA
<213> ORGANISM: Artificial Sequence
<220> FEATURE:
<223> OTHER INFORMATION: Reverse primer of monkey MG53 S255Q mutant

<400> SEQUENCE: 100
tccagacggg cgggtggggg ttgctctgcc aggatctt                             38
```

<210> SEQ ID NO 101
<211> LENGTH: 36
<212> TYPE: DNA
<213> ORGANISM: Artificial Sequence
<220> FEATURE:
<223> OTHER INFORMATION: Forward primer of monkey MG53 S255Y mutant

<400> SEQUENCE: 101
agatcctggc agagtatccc cacccgccc gtctgg                                36

<210> SEQ ID NO 102
<211> LENGTH: 36
<212> TYPE: DNA
<213> ORGANISM: Artificial Sequence
<220> FEATURE:
<223> OTHER INFORMATION: Reverse primer of monkey MG53 S255Y mutant

<400> SEQUENCE: 102
ccagacgggc gggtgggggga tactctgcca ggatct                              36

<210> SEQ ID NO 103
<211> LENGTH: 37
<212> TYPE: DNA
<213> ORGANISM: Artificial Sequence
<220> FEATURE:
<223> OTHER INFORMATION: Forward primer of monkey MG53 S255D mutant

<400> SEQUENCE: 103
aagatcctgg cagaggatcc cccacccgcc cgtctgg                              37

<210> SEQ ID NO 104
<211> LENGTH: 37
<212> TYPE: DNA
<213> ORGANISM: Artificial Sequence
<220> FEATURE:
<223> OTHER INFORMATION: Reverse primer of monkey MG53 S255D mutant

<400> SEQUENCE: 104
ccagacgggc gggtggggga tcctctgcca ggatctt                              37

<210> SEQ ID NO 105
<211> LENGTH: 37
<212> TYPE: DNA
<213> ORGANISM: Artificial Sequence
<220> FEATURE:
<223> OTHER INFORMATION: Forward primer of monkey MG53 S255R mutant

<400> SEQUENCE: 105
aagatcctgg cagagcgtcc cccacccgcc cgtctgg                              37

<210> SEQ ID NO 106
<211> LENGTH: 37
<212> TYPE: DNA
<213> ORGANISM: Artificial Sequence
<220> FEATURE:
<223> OTHER INFORMATION: Reverse primer of monkey MG53 S255R mutant

<400> SEQUENCE: 106
ccagacgggc gggtggggga cgctctgcca ggatctt                              37

<210> SEQ ID NO 107
<211> LENGTH: 36
<212> TYPE: DNA
<213> ORGANISM: Artificial Sequence
<220> FEATURE:

<223> OTHER INFORMATION: Forward primer of swine MG53 S255A mutant

<400> SEQUENCE: 107
aagatcctgg cagaggcgcc cccacctgcc cgcctg    36

<210> SEQ ID NO 108
<211> LENGTH: 36
<212> TYPE: DNA
<213> ORGANISM: Artificial Sequence
<220> FEATURE:
<223> OTHER INFORMATION: Reverse primer of swine MG53 S255A mutant

<400> SEQUENCE: 108
caggcgggca ggtgggggcg cctctgccag gatctt    36

<210> SEQ ID NO 109
<211> LENGTH: 37
<212> TYPE: DNA
<213> ORGANISM: Artificial Sequence
<220> FEATURE:
<223> OTHER INFORMATION: Forward primer of swine MG53 S255G mutant

<400> SEQUENCE: 109
aagatcctgg cagaggggcc cccacctgcc cgcctgg    37

<210> SEQ ID NO 110
<211> LENGTH: 37
<212> TYPE: DNA
<213> ORGANISM: Artificial Sequence
<220> FEATURE:
<223> OTHER INFORMATION: Reverse primer of swine MG53 S255G mutant

<400> SEQUENCE: 110
ccaggcgggc aggtgggggc ccctctgcca ggatctt    37

<210> SEQ ID NO 111
<211> LENGTH: 36
<212> TYPE: DNA
<213> ORGANISM: Artificial Sequence
<220> FEATURE:
<223> OTHER INFORMATION: Forward primer of swine MG53 S255L mutant

<400> SEQUENCE: 111
agatcctggc agagttgccc ccacctgccc gcctgg    36

<210> SEQ ID NO 112
<211> LENGTH: 36
<212> TYPE: DNA
<213> ORGANISM: Artificial Sequence
<220> FEATURE:
<223> OTHER INFORMATION: Reverse primer of swine MG53 S255L mutant

<400> SEQUENCE: 112
ccaggcgggc aggtgggggc aactctgcca ggatct    36

<210> SEQ ID NO 113
<211> LENGTH: 36
<212> TYPE: DNA
<213> ORGANISM: Artificial Sequence
<220> FEATURE:
<223> OTHER INFORMATION: Forward primer of swine MG53 S255W mutant

<400> SEQUENCE: 113
agatcctggc agagtggccc ccacctgccc gcctgg    36

```
<210> SEQ ID NO 114
<211> LENGTH: 36
<212> TYPE: DNA
<213> ORGANISM: Artificial Sequence
<220> FEATURE:
<223> OTHER INFORMATION: Reverse primer of swine MG53 S255W mutant

<400> SEQUENCE: 114
ccaggcgggc aggtgggggc cactctgcca ggatct                              36

<210> SEQ ID NO 115
<211> LENGTH: 37
<212> TYPE: DNA
<213> ORGANISM: Artificial Sequence
<220> FEATURE:
<223> OTHER INFORMATION: Forward primer of swine MG53 S255Q mutant

<400> SEQUENCE: 115
aagatcctgg cagagcagcc cccacctgcc cgcctgg                             37

<210> SEQ ID NO 116
<211> LENGTH: 37
<212> TYPE: DNA
<213> ORGANISM: Artificial Sequence
<220> FEATURE:
<223> OTHER INFORMATION: Reverse primer of swine MG53 S255Q mutant

<400> SEQUENCE: 116
ccaggcgggc aggtgggggc tgctctgcca ggatctt                             37

<210> SEQ ID NO 117
<211> LENGTH: 37
<212> TYPE: DNA
<213> ORGANISM: Artificial Sequence
<220> FEATURE:
<223> OTHER INFORMATION: Forward primer of swine MG53 S255Y mutant

<400> SEQUENCE: 117
agatcctggc agagtatccc ccacctgccc gcctgga                             37

<210> SEQ ID NO 118
<211> LENGTH: 37
<212> TYPE: DNA
<213> ORGANISM: Artificial Sequence
<220> FEATURE:
<223> OTHER INFORMATION: Reverse primer of swine MG53 S255Y mutant

<400> SEQUENCE: 118
tccaggcggg caggtggggg atactctgcc aggatct                             37

<210> SEQ ID NO 119
<211> LENGTH: 38
<212> TYPE: DNA
<213> ORGANISM: Artificial Sequence
<220> FEATURE:
<223> OTHER INFORMATION: Forward primer of swine MG53 S255D mutant

<400> SEQUENCE: 119
aagatcctgg cagaggatcc cccacctgcc cgcctgga                            38

<210> SEQ ID NO 120
<211> LENGTH: 38
<212> TYPE: DNA
<213> ORGANISM: Artificial Sequence
<220> FEATURE:
<223> OTHER INFORMATION: Reverse primer of swine MG53 S255D mutant
```

<400> SEQUENCE: 120
tccaggcggg caggtggggg atcctctgcc aggatctt         38

<210> SEQ ID NO 121
<211> LENGTH: 37
<212> TYPE: DNA
<213> ORGANISM: Artificial Sequence
<220> FEATURE:
<223> OTHER INFORMATION: Forward primer of swine MG53 S255R mutant

<400> SEQUENCE: 121
aagatcctgg cagagcggcc cccacctgcc cgcctgg         37

<210> SEQ ID NO 122
<211> LENGTH: 37
<212> TYPE: DNA
<213> ORGANISM: Artificial Sequence
<220> FEATURE:
<223> OTHER INFORMATION: Reverse primer of swine MG53 S255R mutant

<400> SEQUENCE: 122
ccaggcgggc aggtgggggc cgctctgcca ggatctt         37

<210> SEQ ID NO 123
<211> LENGTH: 36
<212> TYPE: DNA
<213> ORGANISM: Artificial Sequence
<220> FEATURE:
<223> OTHER INFORMATION: Forward primer of dog MG53 S255A mutant

<400> SEQUENCE: 123
aagatcctgg cagaagcacc accgcctgcc cgtttg         36

<210> SEQ ID NO 124
<211> LENGTH: 36
<212> TYPE: DNA
<213> ORGANISM: Artificial Sequence
<220> FEATURE:
<223> OTHER INFORMATION: Reverse primer of dog MG53 S255A mutant

<400> SEQUENCE: 124
caaacgggca ggcggtggtg cttctgccag gatctt         36

<210> SEQ ID NO 125
<211> LENGTH: 37
<212> TYPE: DNA
<213> ORGANISM: Artificial Sequence
<220> FEATURE:
<223> OTHER INFORMATION: Forward primer of dog MG53 S255G mutant

<400> SEQUENCE: 125
aagatcctgg cagaaggacc accgcctgcc cgtttgg         37

<210> SEQ ID NO 126
<211> LENGTH: 37
<212> TYPE: DNA
<213> ORGANISM: Artificial Sequence
<220> FEATURE:
<223> OTHER INFORMATION: Reverse primer of dog MG53 S255G mutant

<400> SEQUENCE: 126
ccaaacgggc aggcggtggt ccttctgcca ggatctt         37

<210> SEQ ID NO 127
<211> LENGTH: 36

-continued

<212> TYPE: DNA
<213> ORGANISM: Artificial Sequence
<220> FEATURE:
<223> OTHER INFORMATION: Forward primer of dog MG53 S255L mutant

<400> SEQUENCE: 127
agatcctggc agaattacca ccgcctgccc gtttgg                                36

<210> SEQ ID NO 128
<211> LENGTH: 36
<212> TYPE: DNA
<213> ORGANISM: Artificial Sequence
<220> FEATURE:
<223> OTHER INFORMATION: Reverse primer of dog MG53 S255L mutant

<400> SEQUENCE: 128
ccaaacgggc aggcggtggt aattctgcca ggatct                                36

<210> SEQ ID NO 129
<211> LENGTH: 37
<212> TYPE: DNA
<213> ORGANISM: Artificial Sequence
<220> FEATURE:
<223> OTHER INFORMATION: Forward primer of dog MG53 S255W mutant

<400> SEQUENCE: 129
agatcctggc agaatggcca ccgcctgccc gtttgga                               37

<210> SEQ ID NO 130
<211> LENGTH: 37
<212> TYPE: DNA
<213> ORGANISM: Artificial Sequence
<220> FEATURE:
<223> OTHER INFORMATION: Reverse primer of dog MG53 S255W mutant

<400> SEQUENCE: 130
tccaaacggg caggcggtgg ccattctgcc aggatct                               37

<210> SEQ ID NO 131
<211> LENGTH: 37
<212> TYPE: DNA
<213> ORGANISM: Artificial Sequence
<220> FEATURE:
<223> OTHER INFORMATION: Forward primer of dog MG53 S255Q mutant

<400> SEQUENCE: 131
aagatcctgg cagaacaacc accgcctgcc cgtttgg                               37

<210> SEQ ID NO 132
<211> LENGTH: 37
<212> TYPE: DNA
<213> ORGANISM: Artificial Sequence
<220> FEATURE:
<223> OTHER INFORMATION: Reverse primer of dog MG53 S255Q mutant

<400> SEQUENCE: 132
ccaaacgggc aggcggtggt tgttctgcca ggatctt                               37

<210> SEQ ID NO 133
<211> LENGTH: 37
<212> TYPE: DNA
<213> ORGANISM: Artificial Sequence
<220> FEATURE:
<223> OTHER INFORMATION: Forward primer of dog MG53 S255Y mutant

<400> SEQUENCE: 133

```
agatcctggc agaatatcca ccgcctgccc gtttgga                                   37

<210> SEQ ID NO 134
<211> LENGTH: 37
<212> TYPE: DNA
<213> ORGANISM: Artificial Sequence
<220> FEATURE:
<223> OTHER INFORMATION: Reverse primer of dog MG53 S255Y mutant

<400> SEQUENCE: 134
tccaaacggg caggcggtgg atattctgcc aggatct                                   37

<210> SEQ ID NO 135
<211> LENGTH: 38
<212> TYPE: DNA
<213> ORGANISM: Artificial Sequence
<220> FEATURE:
<223> OTHER INFORMATION: Forward primer of dog MG53 S255D mutant

<400> SEQUENCE: 135
aagatcctgg cagaagatcc accgcctgcc cgtttgga                                  38

<210> SEQ ID NO 136
<211> LENGTH: 38
<212> TYPE: DNA
<213> ORGANISM: Artificial Sequence
<220> FEATURE:
<223> OTHER INFORMATION: Reverse primer of dog MG53 S255D mutant

<400> SEQUENCE: 136
tccaaacggg caggcggtgg atcttctgcc aggatctt                                  38

<210> SEQ ID NO 137
<211> LENGTH: 37
<212> TYPE: DNA
<213> ORGANISM: Artificial Sequence
<220> FEATURE:
<223> OTHER INFORMATION: Forward primer of dog MG53 S255R mutant

<400> SEQUENCE: 137
aagatcctgg cagaacgacc accgcctgcc cgtttgg                                   37

<210> SEQ ID NO 138
<211> LENGTH: 37
<212> TYPE: DNA
<213> ORGANISM: Artificial Sequence
<220> FEATURE:
<223> OTHER INFORMATION: Reverse primer of dog MG53 S255R mutant

<400> SEQUENCE: 138
ccaaacgggc aggcggtggt cgttctgcca ggatctt                                   37

<210> SEQ ID NO 139
<211> LENGTH: 477
<212> TYPE: PRT
<213> ORGANISM: Homo sapiens

<400> SEQUENCE: 139

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45
```

```
Gly Thr Val Leu Cys Pro Cys Cys Gln Ala Pro Thr Arg Pro Gln Ala
     50                  55                  60

Leu Ser Thr Asn Leu Gln Leu Ala Arg Leu Val Glu Gly Leu Ala Gln
 65                  70                  75                  80

Val Pro Gln Gly His Cys Glu His Leu Asp Pro Leu Ser Ile Tyr
                 85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Leu Gln Leu Gln Glu Ala Cys
130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Cys
            180                 185                 190

Glu Ala Glu Arg Val Arg Gly Glu Ala Gly Val Ala Leu Arg Arg Glu
            195                 200                 205

Leu Gly Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
            290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Arg Pro
        435                 440                 445

Val Tyr Pro Phe Phe Asp Val Cys Trp His Asp Lys Gly Lys Asn Ala
    450                 455                 460

Gln Pro Leu Leu Leu Val Gly Pro Glu Gly Ala Glu Ala
```

<210> SEQ ID NO 140
<211> LENGTH: 333
<212> TYPE: PRT
<213> ORGANISM: Homo sapiens

<400> SEQUENCE: 140

Met Arg Lys Glu Lys Ser Val Ala Val Leu Glu His Gln Leu Val Glu
1               5                   10                  15

Val Glu Glu Thr Val Arg Gln Phe Arg Gly Ala Val Gly Glu Gln Leu
            20                  25                  30

Gly Lys Met Arg Val Phe Leu Ala Ala Leu Glu Gly Ser Leu Asp Arg
        35                  40                  45

Glu Ala Glu Arg Val Arg Gly Glu Ala Gly Val Ala Leu Arg Arg Glu
    50                  55                  60

Leu Gly Ser Leu Asn Ser Tyr Leu Glu Gln Leu Arg Gln Met Glu Lys
65                  70                  75                  80

Val Leu Glu Glu Val Ala Asp Lys Pro Gln Thr Glu Phe Leu Met Lys
                85                  90                  95

Tyr Cys Leu Val Thr Ser Arg Leu Gln Lys Ile Leu Ala Glu Ser Pro
            100                 105                 110

Pro Pro Ala Arg Leu Asp Ile Gln Leu Pro Ile Ile Ser Asp Asp Phe
        115                 120                 125

Lys Phe Gln Val Trp Arg Lys Met Phe Arg Ala Leu Met Pro Ala Leu
    130                 135                 140

Glu Glu Leu Thr Phe Asp Pro Ser Ser Ala His Pro Ser Leu Val Val
145                 150                 155                 160

Ser Ser Ser Gly Arg Arg Val Glu Cys Ser Glu Gln Lys Ala Pro Pro
                165                 170                 175

Ala Gly Glu Asp Pro Arg Gln Phe Asp Lys Ala Val Ala Val Val Ala
            180                 185                 190

His Gln Gln Leu Ser Glu Gly Glu His Tyr Trp Glu Val Asp Val Gly
        195                 200                 205

Asp Lys Pro Arg Trp Ala Leu Gly Val Ile Ala Ala Glu Ala Pro Arg
    210                 215                 220

Arg Gly Arg Leu His Ala Val Pro Ser Gln Gly Leu Trp Leu Leu Gly
225                 230                 235                 240

Leu Arg Glu Gly Lys Ile Leu Glu Ala His Val Glu Ala Lys Glu Pro
                245                 250                 255

Arg Ala Leu Arg Ser Pro Glu Arg Arg Pro Thr Arg Ile Gly Leu Tyr
            260                 265                 270

Leu Ser Phe Gly Asp Gly Val Leu Ser Phe Tyr Asp Ala Ser Asp Ala
        275                 280                 285

Asp Ala Leu Val Pro Leu Phe Ala Phe His Glu Arg Leu Pro Arg Pro
    290                 295                 300

Val Tyr Pro Phe Phe Asp Val Cys Trp His Asp Lys Gly Lys Asn Ala
305                 310                 315                 320

Gln Pro Leu Leu Leu Val Gly Pro Glu Gly Ala Glu Ala
                325                 330

<210> SEQ ID NO 141
<211> LENGTH: 333
<212> TYPE: PRT
<213> ORGANISM: Homo sapiens -continued

```
<400> SEQUENCE: 141

Met Arg Lys Glu Lys Ser Val Ala Val Leu Glu His Gln Leu Val Glu
1               5                   10                  15

Val Glu Glu Thr Val Arg Gln Phe Arg Gly Ala Val Gly Glu Gln Leu
            20                  25                  30

Gly Lys Met Arg Val Phe Leu Ala Ala Leu Glu Gly Ser Leu Asp Arg
        35                  40                  45

Glu Ala Glu Arg Val Arg Gly Glu Ala Gly Val Ala Leu Arg Arg Glu
    50                  55                  60

Leu Gly Ser Leu Asn Ser Tyr Leu Glu Gln Leu Arg Gln Met Glu Lys
65                  70                  75                  80

Val Leu Glu Glu Val Ala Asp Lys Pro Gln Thr Glu Phe Leu Met Lys
                85                  90                  95

Tyr Cys Leu Val Thr Ser Arg Leu Gln Lys Ile Leu Ala Glu Ser Pro
            100                 105                 110

Pro Pro Ala Arg Leu Asp Ile Gln Leu Pro Ile Ile Ser Asp Asp Phe
        115                 120                 125

Lys Phe Gln Val Trp Arg Lys Met Phe Arg Ala Leu Met Pro Ala Leu
130                 135                 140

Glu Glu Leu Thr Phe Asp Pro Ser Ser Ala His Pro Ser Leu Val Val
145                 150                 155                 160

Ser Ser Ser Gly Arg Arg Val Glu Cys Ser Gly Gln Lys Ala Pro Pro
                165                 170                 175

Ala Gly Glu Asp Pro Arg Gln Phe Asp Lys Ala Val Ala Val Val Ala
            180                 185                 190

His Gln Gln Leu Ser Glu Gly Glu His Tyr Trp Glu Val Asp Val Gly
        195                 200                 205

Asp Lys Pro Arg Trp Ala Leu Gly Val Ile Ala Ala Glu Ala Pro Arg
    210                 215                 220

Arg Gly Arg Leu His Ala Val Pro Ser Gln Gly Leu Trp Leu Leu Gly
225                 230                 235                 240

Leu Arg Glu Gly Lys Ile Leu Glu Ala His Val Glu Ala Lys Glu Pro
                245                 250                 255

Arg Ala Leu Arg Ser Pro Glu Arg Arg Pro Thr Arg Ile Gly Leu Tyr
            260                 265                 270

Leu Ser Phe Gly Asp Gly Val Leu Ser Phe Tyr Asp Ala Ser Asp Ala
        275                 280                 285

Asp Ala Leu Val Pro Leu Phe Ala Phe His Glu Arg Leu Pro Arg Pro
    290                 295                 300

Val Tyr Pro Phe Phe Asp Val Cys Trp His Asp Lys Gly Lys Asn Ala
305                 310                 315                 320

Gln Pro Leu Leu Leu Val Gly Pro Glu Gly Ala Glu Ala
                325                 330

<210> SEQ ID NO 142
<211> LENGTH: 269
<212> TYPE: PRT
<213> ORGANISM: Homo sapiens

<400> SEQUENCE: 142

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30
```

```
Phe Cys Arg Ala Cys Leu Gly Arg Val Ala Gly Glu Pro Ala Ala Asp
             35                  40                  45

Gly Thr Val Leu Cys Pro Cys Gln Ala Pro Thr Arg Pro Gln Ala
 50                  55                  60

Leu Ser Thr Asn Leu Gln Leu Ala Arg Leu Val Glu Gly Leu Ala Gln
 65                  70                  75                  80

Val Pro Gln Gly His Cys Glu His Leu Asp Pro Leu Ser Ile Tyr
                 85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
                115                 120                 125

Leu Lys Thr Gln Leu Pro Gln Gln Lys Leu Gln Leu Gln Glu Ala Cys
130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
                180                 185                 190

Glu Ala Glu Arg Val Arg Gly Glu Ala Gly Val Ala Leu Arg Arg Glu
                195                 200                 205

Leu Gly Ser Leu Asn Ser Tyr Leu Glu Gln Leu Arg Gln Met Glu Lys
                210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser
                260                 265

<210> SEQ ID NO 143
<211> LENGTH: 1434
<212> TYPE: DNA
<213> ORGANISM: Homo sapiens

<400> SEQUENCE: 143
atgtcggctg cgcccggcct cctgcaccag gagctgtcct gcccgctgtg cctgcagctg      60
ttcgacgcgc ccgtgacagc cgagtgcggc cacagtttct gccgcgcctg cctaggccgc     120
gtggccgggg agccggcggc ggatggcacc gttctctgcc cctgctgcca ggcccccacg     180
cggccgcagg cactcagcac caacctgcag ctggcgcgcc tggtggaggg ctggcccag     240 gtgccgcagg gccactgcga ggagcacctg gacccgctga gcatctactg cgagcaggac     300
cgcgcgctgg tgtgcggagt gtgcgcctca ctcggctcgc accgcggtca tcgcctcctg     360
cctgccgccg aggcccacgc acgcctcaag acacagctgc cacagcagaa actgcagctg     420
caggaggcat gcatgcgtaa ggagaagagt gtggctgtgc tggagcatca gctggtggag     480
gtggaggaga cagtgcgtca gttccgggg gccgtggggg agcagctggg caagatgcgg     540
gtgttcctgg ctgcactgga gggctccttg gactgcgagg cagagcgtgt acggggtgag     600 gcagggggtcg ccttgcgccg ggagctgggg agcctgaact cttacctgga gcagctgcgg     660
cagatggaga aggtcctgga ggaggtggcg gacaagccgc agactgagtt cctcatgaaa     720
tactgcctgg tgaccagcag gctgcagaag atcctggcag agtctccccc acccgcccgt     780
```

```
ctggacatcc agctgccaat tatctcagat gacttcaaat tccaggtgtg gaggaagatg    840
ttccgggctc tgatgccagc gctggaggag ctgacctttg acccgagctc tgcgcacccg    900
agcctggtgg tgtcttcctc tggccgccgc gtggagtgct cggagcagaa ggcgccgccg    960
gccggggagg acccgcgcca gttcgacaag gcggtggcgg tggtgcgcca ccagcagctc   1020
tccgagggcg agcactactg ggaggtggat gttggcgaca agccgcgctg ggcgctgggc   1080
gtgatcgcgg ccgaggcccc ccgccgcggg cgcctgcacg cggtgccctc gcagggcctg   1140
tggctgctgg ggctgcgcga gggcaagatc ctggaggcac acgtggaggc caaggagccg   1200
cgcgctctgc gcagccccga gaggcggccc acgcgcattg cctttacct gagcttcggc    1260 gacggcgtcc tctccttcta cgatgccagc gacgccgacg cgctcgtgcc gcttttt gcc   1320 ttccacgagc gcctgcccag gcccgtgtac cccttcttcg acgtgtgctg gcacgacaag   1380
ggcaagaatg cccagccgct gctgctcgtg ggtcccgaag gcgccgaggc ctga           1434

<210> SEQ ID NO 144
<211> LENGTH: 1002
<212> TYPE: DNA
<213> ORGANISM: Homo sapiens

<400> SEQUENCE: 144
atgcgcaagg agaagagtgt ggctgtgctg gagcatcagc tggtggaggt ggaggagaca     60
gtgcgtcagt tccgggggc cgtggggag cagctgggca agatgcgggt gttcctggct      120
gcactggagg gctccttgga ccgcgaggca gagcgtgtac ggggtgaggc aggggtcgcc    180
ttgcgccggg agctggggag cctgaactct tacctggagc agctgcggca gatggagaag    240
gtcctggagg aggtggcgga caagccgcag actgagttcc tcatgaaata ctgcctggtg    300
accagcaggc tgcagaagat cctggcagag tctcccccac ccgcccgtct ggacatccag    360
ctgccaatta tctcagatga cttcaaattc caggtgtgga ggaagatgtt ccgggctctg    420
atgccagcgc tggaggagct gacctttgac ccgagctctg cgcacccgag cctggtggtg    480
tcttcctctg gccgccgcgt ggagtgctcg agcagaagg cgccgccggc cggggaggac    540
ccgcgccagt tcgacaaggc ggtggcgtg gtggcgcacc agcagctctc cgagggcgag    600
cactactggg aggtggatgt tggcgacaag ccgcgctggg cgctgggcgt gatcgcggcc    660
gaggcccccc gccgcgggcg cctgcacgcg gtgccctcgc agggcctgtg ctgctgggg    720 ctgcgcgagg gcaagatcct ggaggcacac gtggaggcca aggagccgcg cgctctgcgc    780
agccccgaga ggcggccac gcgcattggc ctttacctga gcttcggcga cggcgtcctc    840
tccttctacg atgccagcga cgccgacgcg ctcgtgccgc ttttt gcctt ccacgagcgc    900 ctgcccaggc ccgtgtaccc cttcttcgac gtgtgctggc acgacaaggg caagaatgcc    960
cagccgctgc tgctcgtggg tcccgaaggc gccgaggcct ga                       1002

<210> SEQ ID NO 145
<211> LENGTH: 1002
<212> TYPE: DNA
<213> ORGANISM: Homo sapiens

<400> SEQUENCE: 145
atgcgtaagg agaagagtgt ggctgtgctg gagcatcagc tggtggaggt ggaggagaca     60
gtgcgtcagt tccgggggc cgtggggag cagctgggca agatgcgggt gttcctggct      120
gcactggagg gctccttgga ccgcgaggca gagcgtgtac ggggtgaggc aggggtcgcc    180
ttgcgccggg agctggggag cctgaactct tacctggagc agctgcggca gatggagaag    240
```

```
gtcctggagg aggtggcgga caagccgcag actgagttcc tcatgaaata ctgcctggtg    300
accagcaggc tgcagaagat cctggcagag tctcccccac ccgcccgtct ggacatccag    360
ctgccaatta tctcagatga cttcaaattc caggtgtgga ggaagatgtt ccgggctctg    420
atgccagcgc tggaggagct gacctttgac ccgagctctg cgcacccgag cctggtggtg    480
tcttcctctg gccgccgcgt ggagtgctcg gggcagaagg cgccgccggc cggggaggac    540
ccgcgccagt tcgacaaggc ggtggcggtg gtggcgcacc agcagctctc cgagggcgag    600
cactactggg aggtggatgt tggcgacaag ccgcgctggg cgctgggcgt gatcgcggcc    660
gaggcccccc gccgcgggcg cctgcacgcg gtgccctcgc agggcctgtg gctgctgggg    720
ctgcgcgagg gcaagatcct ggaggcacac gtggaggcca aggagccgcg cgctctgcgc    780
agccccgaga ggcggcccac gcgcattggc ctttacctga gcttcggcga cggcgtcctc    840
tccttctacg atgccagcga cgccgacgcg ctcgtgccgc ttttgccttc ccacgagcgc    900
ctgcccaggc ccgtgtaccc cttcttcgac gtgtgctggc acgacaaggg caagaatgcc    960
cagccgctgc tgctcgtggg tcccgaaggc gccgaggcct ga                      1002

<210> SEQ ID NO 146
<211> LENGTH: 810
<212> TYPE: DNA
<213> ORGANISM: Homo sapiens

<400> SEQUENCE: 146
atgtcggctg cgcccggcct cctgcaccag gagctgtcct gcccgctgtg cctgcagctg     60
ttcgacgcgc ccgtgacagc cgagtgcggc cacagtttct gccgcgcctg cctaggccgc    120
gtggccgggg agccggcggc ggatggcacc gttctctgcc cctgctgcca ggcccccacg    180
cggccgcagg cactcagcac caacctgcag ctggcgcgcc tggtggaggg gctggcccag    240
gtgccgcagg gccactgcga ggagcacctg acccgctga gcatctactg cgagcaggac    300
cgcgcgctgg tgtgcggagt gtgcgcctca ctcggctcgc accgcggtca tcgcctcctg    360
cctgccgccg aggcccacgc acgcctcaag acacagctgc cacagcagaa actgcagctg    420
caggaggcat gcatgcgtaa ggagaagagt gtggctgtgc tggagcatca gctggtggag    480
gtggaggaga cagtgcgtca gttccggggg gccgtggggg agcagctggg caagatgcgg    540
gtgttcctgg ctgcactgga gggctccttg gaccgcgagg cagagcgtgt acggggtgag    600
gcaggggtcg ccttgcgccg ggagctgggg agcctgaact cttacctgga gcagctgcgg    660
cagatggaga aggtcctgga ggaggtggcg acaagccgc agactgagtt cctcatgaaa    720
tactgcctgg tgaccagcag gctgcagaag atcctggcag agtctccccc acccgcccgt    780
ctggacatcc agctgccaat tatctcctga                                    810

<210> SEQ ID NO 147
<211> LENGTH: 477
<212> TYPE: PRT
<213> ORGANISM: Artificial Sequence
<220> FEATURE:
<223> OTHER INFORMATION: Amino acid sequence of a human MG53 subtype
      S255A mutant

<400> SEQUENCE: 147

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30
```

-continued

```
Phe Cys Arg Ala Cys Leu Gly Arg Val Ala Gly Pro Ala Ala Asp
    35                  40                  45

Gly Thr Val Leu Cys Pro Cys Cys Gln Ala Pro Thr Arg Pro Gln Ala
        50                  55                  60

Leu Ser Thr Asn Leu Gln Leu Ala Arg Leu Val Glu Gly Leu Ala Gln
65                  70                  75                  80

Val Pro Gln Gly His Cys Glu His Leu Asp Pro Leu Ser Ile Tyr
                85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Cys
                180                 185                 190

Glu Ala Glu Arg Val Arg Gly Glu Ala Gly Val Ala Leu Arg Arg Glu
                195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ala Pro
                245                 250                 255

Pro Pro Ala Arg Leu Asp Ile Gln Leu Pro Ile Ile Ser Asp Asp Phe
                260                 265                 270

Lys Phe Gln Val Trp Arg Lys Met Phe Arg Ala Leu Met Pro Ala Leu
    275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
    355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
                420                 425                 430

Asp Ala Leu Val Pro Leu Phe Ala Phe His Glu Arg Leu Pro Arg Pro
            435                 440                 445
```

```
Val Tyr Pro Phe Phe Asp Val Cys Trp His Asp Lys Gly Lys Asn Ala
    450                 455                 460

Gln Pro Leu Leu Leu Val Gly Pro Glu Gly Ala Glu Ala
465                 470                 475

<210> SEQ ID NO 148
<211> LENGTH: 333
<212> TYPE: PRT
<213> ORGANISM: Artificial Sequence
<220> FEATURE:
<223> OTHER INFORMATION: Amino acid sequence of a human MG53 subtype
      S255A mutant

<400> SEQUENCE: 148

Met Arg Lys Glu Lys Ser Val Ala Val Leu Glu His Gln Leu Val Glu
1               5                   10                  15

Val Glu Glu Thr Val Arg Gln Phe Arg Gly Ala Val Gly Glu Gln Leu
            20                  25                  30

Gly Lys Met Arg Val Phe Leu Ala Ala Leu Glu Gly Ser Leu Asp Arg
        35                  40                  45

Glu Ala Glu Arg Val Arg Gly Glu Ala Gly Val Ala Leu Arg Arg Glu
    50                  55                  60

Leu Gly Ser Leu Asn Ser Tyr Leu Glu Gln Leu Arg Gln Met Glu Lys
65                  70                  75                  80

Val Leu Glu Glu Val Ala Asp Lys Pro Gln Thr Glu Phe Leu Met Lys
                85                  90                  95

Tyr Cys Leu Val Thr Ser Arg Leu Gln Lys Ile Leu Ala Glu Ala Pro
            100                 105                 110

Pro Pro Ala Arg Leu Asp Ile Gln Leu Pro Ile Ile Ser Asp Asp Phe
        115                 120                 125

Lys Phe Gln Val Trp Arg Lys Met Phe Arg Ala Leu Met Pro Ala Leu
130                 135                 140

Glu Glu Leu Thr Phe Asp Pro Ser Ser Ala His Pro Ser Leu Val Val
145                 150                 155                 160

Ser Ser Ser Gly Arg Arg Val Glu Cys Ser Glu Gln Lys Ala Pro Pro
                165                 170                 175

Ala Gly Glu Asp Pro Arg Gln Phe Asp Lys Ala Val Ala Val Val Ala
            180                 185                 190

His Gln Gln Leu Ser Glu Gly Glu His Tyr Trp Glu Val Asp Val Gly
        195                 200                 205

Asp Lys Pro Arg Trp Ala Leu Gly Val Ile Ala Ala Glu Ala Pro Arg
    210                 215                 220

Arg Gly Arg Leu His Ala Val Pro Ser Gln Gly Leu Trp Leu Leu Gly
225                 230                 235                 240

Leu Arg Glu Gly Lys Ile Leu Glu Ala His Val Glu Ala Lys Glu Pro
                245                 250                 255

Arg Ala Leu Arg Ser Pro Glu Arg Arg Pro Thr Arg Ile Gly Leu Tyr
            260                 265                 270

Leu Ser Phe Gly Asp Gly Val Leu Ser Phe Tyr Asp Ala Ser Asp Ala
        275                 280                 285

Asp Ala Leu Val Pro Leu Phe Ala Phe His Glu Arg Leu Pro Arg Pro
    290                 295                 300

Val Tyr Pro Phe Phe Asp Val Cys Trp His Asp Lys Gly Lys Asn Ala
305                 310                 315                 320

Gln Pro Leu Leu Leu Val Gly Pro Glu Gly Ala Glu Ala
                325                 330
```

<210> SEQ ID NO 149
<211> LENGTH: 333
<212> TYPE: PRT
<213> ORGANISM: Artificial Sequence
<220> FEATURE:
<223> OTHER INFORMATION: Amino acid sequence of a human MG53 subtype S255A mutant

<400> SEQUENCE: 149

Met Arg Lys Glu Lys Ser Val Ala Val Leu Glu His Gln Leu Val Glu
1               5                   10                  15

Val Glu Thr Val Arg Gln Phe Arg Gly Ala Val Gly Glu Gln Leu
            20                  25                  30

Gly Lys Met Arg Val Phe Leu Ala Ala Leu Glu Gly Ser Leu Asp Arg
        35                  40                  45

Glu Ala Glu Arg Val Arg Gly Glu Ala Gly Val Ala Leu Arg Arg Glu
    50                  55                  60

Leu Gly Ser Leu Asn Ser Tyr Leu Glu Gln Leu Arg Gln Met Glu Lys
65                  70                  75                  80

Val Leu Glu Glu Val Ala Asp Lys Pro Gln Thr Glu Phe Leu Met Lys
                85                  90                  95

Tyr Cys Leu Val Thr Ser Arg Leu Gln Lys Ile Leu Ala Glu Ala Pro
            100                 105                 110

Pro Pro Ala Arg Leu Asp Ile Gln Leu Pro Ile Ile Ser Asp Asp Phe
        115                 120                 125

Lys Phe Gln Val Trp Arg Lys Met Phe Arg Ala Leu Met Pro Ala Leu
130                 135                 140

Glu Glu Leu Thr Phe Asp Pro Ser Ser Ala His Pro Ser Leu Val Val
145                 150                 155                 160

Ser Ser Ser Gly Arg Arg Val Glu Cys Ser Gly Gln Lys Ala Pro Pro
                165                 170                 175

Ala Gly Glu Asp Pro Arg Gln Phe Asp Lys Ala Val Ala Val Val Ala
            180                 185                 190

His Gln Gln Leu Ser Glu Gly Glu His Tyr Trp Glu Val Asp Val Gly
        195                 200                 205

Asp Lys Pro Arg Trp Ala Leu Gly Val Ile Ala Ala Glu Ala Pro Arg
    210                 215                 220

Arg Gly Arg Leu His Ala Val Pro Ser Gln Gly Leu Trp Leu Leu Gly
225                 230                 235                 240

Leu Arg Glu Gly Lys Ile Leu Glu Ala His Val Glu Ala Lys Glu Pro
                245                 250                 255

Arg Ala Leu Arg Ser Pro Glu Arg Arg Pro Thr Arg Ile Gly Leu Tyr
            260                 265                 270

Leu Ser Phe Gly Asp Gly Val Leu Ser Phe Tyr Asp Ala Ser Asp Ala
        275                 280                 285

Asp Ala Leu Val Pro Leu Phe Ala Phe His Glu Arg Leu Pro Arg Pro
    290                 295                 300

Val Tyr Pro Phe Phe Asp Val Cys Trp His Asp Lys Gly Lys Asn Ala
305                 310                 315                 320

Gln Pro Leu Leu Leu Val Gly Pro Glu Gly Ala Glu Ala
                325                 330

<210> SEQ ID NO 150
<211> LENGTH: 269
<212> TYPE: PRT

<213> ORGANISM: Artificial Sequence
<220> FEATURE:
<223> OTHER INFORMATION: Amino acid sequence of a human MG53 subtype S255A mutant

<400> SEQUENCE: 150

```
Met Ser Ala Ala Pro Gly Leu Leu His Gln Glu Leu Ser Cys Pro Leu
1               5                   10                  15
Cys Leu Gln Leu Phe Asp Ala Pro Val Thr Ala Glu Cys Gly His Ser
            20                  25                  30
Phe Cys Arg Ala Cys Leu Gly Arg Val Ala Gly Glu Pro Ala Ala Asp
        35                  40                  45
Gly Thr Val Leu Cys Pro Cys Cys Gln Ala Pro Thr Arg Pro Gln Ala
    50                  55                  60
Leu Ser Thr Asn Leu Gln Leu Ala Arg Leu Val Glu Gly Leu Ala Gln
65                  70                  75                  80
Val Pro Gln Gly His Cys Glu Glu His Leu Asp Pro Leu Ser Ile Tyr
                85                  90                  95
Cys Glu Gln Asp Arg Ala Leu Val Cys Gly Val Cys Ala Ser Leu Gly
            100                 105                 110
Ser His Arg Gly His Arg Leu Leu Pro Ala Ala Glu Ala His Ala Arg
        115                 120                 125
Leu Lys Thr Gln Leu Pro Gln Gln Lys Leu Gln Leu Gln Glu Ala Cys
    130                 135                 140
Met Arg Lys Glu Lys Ser Val Ala Val Leu Glu His Gln Leu Val Glu
145                 150                 155                 160
Val Glu Thr Val Arg Gln Phe Arg Gly Ala Val Gly Glu Gln Leu
                165                 170                 175
Gly Lys Met Arg Val Phe Leu Ala Ala Leu Glu Gly Ser Leu Asp Arg
            180                 185                 190
Glu Ala Glu Arg Val Arg Gly Glu Ala Gly Val Ala Leu Arg Arg Glu
        195                 200                 205
Leu Gly Ser Leu Asn Ser Tyr Leu Glu Gln Leu Arg Gln Met Glu Lys
    210                 215                 220
Val Leu Glu Glu Val Ala Asp Lys Pro Gln Thr Glu Phe Leu Met Lys
225                 230                 235                 240
Tyr Cys Leu Val Thr Ser Arg Leu Gln Lys Ile Leu Ala Glu Ala Pro
                245                 250                 255
Pro Pro Ala Arg Leu Asp Ile Gln Leu Pro Ile Ile Ser
            260                 265
```

<210> SEQ ID NO 151
<211> LENGTH: 1434
<212> TYPE: DNA
<213> ORGANISM: Artificial Sequence
<220> FEATURE:
<223> OTHER INFORMATION: Encoding nucleic acid sequence of a human MG53 subtype S255A mutant

<400> SEQUENCE: 151

```
atgtcggctg cgcccggcct cctgcaccag gagctgtcct gcccgctgtg cctgcagctg      60
ttcgacgcgc ccgtgacagc cgagtgcggc cacagtttct gccgcgcctg cctaggccgc     120
gtggccgggg agccggcggc ggatggcacc gttctctgcc cctgctgcca ggccccacg      180
cggccgcagg cactcagcac caacctgcag ctggcgcgcc tggtggaggg gctggcccag     240
gtgccgcagg gccactgcga ggagcacctg gacccgctga gcatctactg cgagcaggac     300
```

| | |
|---|---|
| cgcgcgctgg tgtgcggagt gtgcgcctca ctcggctcgc accgcggtca tcgcctcctg | 360 |
| cctgccgccg aggcccacgc acgcctcaag acacagctgc cacagcagaa actgcagctg | 420 |
| caggaggcat gcatgcgtaa ggagaagagt gtggctgtgc tggagcatca gctggtggag | 480 |
| gtggaggaga cagtgcgtca gttccggggg gccgtggggg agcagctggg caagatgcgg | 540 |
| gtgttcctgg ctgcactgga gggctccttg gactgcgagg cagagcgtgt acggggtgag | 600 |
| gcaggggtcg ccttgcgccg ggagctgggg agcctgaact cttacctgga gcagctgcgg | 660 |
| cagatggaga aggtcctgga ggaggtggcg gacaagccgc agactgagtt cctcatgaaa | 720 |
| tactgcctgg tgaccagcag gctgcagaag atcctggcag aggctccccc acccgcccgt | 780 |
| ctggacatcc agctgccaat tatctcagat gacttcaaat ccaggtgtgt gaggaagatg | 840 |
| ttccgggctc tgatgccagc gctggaggag ctgacctttg acccgagctc tgcgcacccg | 900 |
| agcctggtgg tgtcttcctc tggccgccgc gtggagtgct cggagcagaa ggcgccgccg | 960 |
| gccggggagg acccgcgcca gttcgacaag gcggtggcgg tggtggcgca ccagcagctc | 1020 |
| tccgagggcg agcactactg ggaggtggat gttggcgaca agccgcgctg ggcgctgggc | 1080 |
| gtgatcgcgg ccgaggcccc ccgccgcggg cgcctgcacg cggtgccctc gcagggcctg | 1140 |
| tggctgctgg ggctgcgcga gggcaagatc ctggaggcac acgtggaggc caaggagccg | 1200 |
| cgcgctctgc gcagccccga gaggcggccc acgcgcattg cctttacct gagcttcggc | 1260 |
| gacggcgtcc tctccttcta cgatgccagc gacgccgacg cgctcgtgcc gcttttgcc | 1320 |
| ttccacgagc gcctgcccag gcccgtgtac cccttcttcg acgtgtgctg cacgacaag | 1380 |
| ggcaagaatg cccagccgct gctgctcgtg ggtcccgaag cgccgaggc ctga | 1434 |

<210> SEQ ID NO 152
<211> LENGTH: 1002
<212> TYPE: DNA
<213> ORGANISM: Artificial Sequence
<220> FEATURE:
<223> OTHER INFORMATION: Encoding nucleic acid sequence of a human MG53
    subtype S255A mutant

<400> SEQUENCE: 152

| | |
|---|---|
| atgcgcaagg agaagagtgt ggctgtgctg gagcatcagc tggtggaggt ggaggagaca | 60 |
| gtgcgtcagt tccgggggc cgtgggggag cagctgggca agatgcgggt gttcctggct | 120 |
| gcactggagg gctccttgga ccgcgaggca gagcgtgtac ggggtgaggc aggggtcgcc | 180 |
| ttgcgccggg agctggggag cctgaactct tacctggagc agctgcggca gatggagaag | 240 |
| gtcctggagg aggtggcgga caagccgcag actgagttcc tcatgaaata ctgcctggtg | 300 |
| accagcaggc tgcagaagat cctggcagag gctcccccac ccgcccgtct ggacatccag | 360 |
| ctgccaatta tctcagatga cttcaaattc aggtgtggag gaagatgtt ccgggctctg | 420 |
| atgccagcgc tggaggagct gacctttgac ccgagctctg cgcacccgag cctggtggtg | 480 |
| tcttcctctg gccgccgcgt ggagtgctcg gagcagaagg cgccgccggc cggggaggac | 540 |
| ccgcgccagt tcgacaaggc ggtggcggtg gtggcgcacc agcagctctc cgagggcgag | 600 |
| cactactggg aggtggatgt tggcgacaag ccgcgctggg cgctgggcgt gatcgcggcc | 660 |
| gaggccccc cgccgcgggc gcctgcacgc gtgccctcgc agggcctgtg ctgctgggg | 720 |
| ctgcgcgagg gcaagatcct ggaggcacac gtggaggcca aggagccgcg cgctctgcgc | 780 |
| agccccgaga ggcggcccac gcgcattggc ctttacctga gcttcggcga cggcgtcctc | 840 |
| tccttctacg atgccagcga cgccgacgcg ctcgtgccgc ttttgccttc cacgagcgc | 900 | ctgcccaggc cgtgtaccc cttcttcgac gtgtgctggc acgacaaggg caagaatgcc    960 cagccgctgc tgctcgtggg tcccgaaggc gccgaggcct ga    1002

<210> SEQ ID NO 153
<211> LENGTH: 1002
<212> TYPE: DNA
<213> ORGANISM: Artificial Sequence
<220> FEATURE:
<223> OTHER INFORMATION: Encoding nucleic acid sequence of a human MG53
      subtype S255A mutant

<400> SEQUENCE: 153
atgcgtaagg agaagagtgt ggctgtgctg gagcatcagc tggtggaggt ggaggagaca    60
gtgcgtcagt tccgggggc cgtggggag cagctgggca agatgcgggt gttcctggct    120
gcactggagg ctccttgga ccgcgaggca gagcgtgtac ggggtgaggc aggggtcgcc    180
ttgcgccggg agctggggag cctgaactct tacctggagc agctgcggca gatggagaag    240
gtcctggagg aggtggcgga caagccgcag actgagttcc tcatgaaata ctgcctggtg    300
accagcaggc tgcagaagat cctggcagag gctcccccac ccgcccgtct ggacatccag    360
ctgccaatta tctcagatga cttcaaattc caggtgtgga ggaagatgtt ccgggctctg    420
atgccagcgc tggaggagct gaccttgac ccgagctctg cgcacccgag cctggtggtg    480
tcttcctctg gccgccgcgt ggagtgctcg gggcagaagg cgccgccggc cggggaggac    540
ccgcgccagt cgacaaggc ggtggcggtg gtggcgcacc agcagctctc cgagggcgag    600
cactactggg aggtggatgt tggcgacaag ccgcgctggg cgctgggcgt gatcgcggcc    660 gaggccccc gccgcgggcg cctgcacgcg gtgccctcgc agggcctgtg gctgctgggg    720
ctgcgcgagg gcaagatcct ggaggcacac gtggaggcca aggagccgcg cgctctgcgc    780
agccccgaga ggcggcccac gcgcattggc ctttacctga gcttcggcga cggcgtcctc    840
tccttctacg atgccagcga cgccgacgcg ctcgtgccgc tttttgcctt ccacgagcgc    900
ctgcccaggc ccgtgtaccc cttcttcgac gtgtgctggc acgacaaggg caagaatgcc    960
cagccgctgc tgctcgtggg tcccgaaggc gccgaggcct ga    1002

<210> SEQ ID NO 154
<211> LENGTH: 810
<212> TYPE: DNA
<213> ORGANISM: Artificial Sequence
<220> FEATURE:
<223> OTHER INFORMATION: Encoding nucleic acid sequence of a human MG53
      subtype S255A mutant

<400> SEQUENCE: 154
atgtcggctg cgcccggcct cctgcaccag gagctgtcct gcccgctgtg cctgcagctg    60
ttcgacgcgc ccgtgacagc cgagtgcggc cacagtttct gccgcgcctg cctaggccgc    120
gtggccgggg agccggcggc ggatggcacc gttctctgcc cctgctgcca ggcccccacg    180
cggccgcagg cactcagcac caacctgcag ctggcgcgcc tggtggaggg gctggcccag    240
gtgccgcagg gccactgcga ggagcacctg gacccgctga gcatctactg cgagcaggac    300
cgcgcgctgt tgtgcggagt gtgcgcctca ctcggctcgc accgcggtca tgcctcctg    360 cctgccgccg aggcccacgc acgcctcaag acacagctgc acagcagaa actgcagctg    420 caggaggcat gcatgcgtaa ggagaagagt gtggctgtgc tggagcatca gctggtggag    480
gtggaggaga cagtgcgtca gttccggggg gccgtgggg agcagctggg caagatgcgg    540
gtgttcctgg ctgcactgga gggctccttg gaccgcgagg cagagcgtgt acggggtgag    600

```
gcaggggtcg ccttgcgccg ggagctgggg agcctgaact cttacctgga gcagctgcgg      660
cagatggaga aggtcctgga ggaggtggcg gacaagccgc agactgagtt cctcatgaaa      720
tactgcctgg tgaccagcag gctgcagaag atcctggcag aggctccccc acccgcccgt      780
ctggacatcc agctgccaat tatctcctga                                       810
```